(12) United States Patent
Buswell et al.

(10) Patent No.: US 10,589,050 B2
(45) Date of Patent: Mar. 17, 2020

(54) ZONE HEATING FOR RESPIRATORY CIRCUITS

(71) Applicant: Fisher & Paykel Healthcare Limited, Auckland (NZ)

(72) Inventors: Matthew Liam Buswell, Auckland (NZ); Helen Cuddy, Auckland (NZ); Thomas James Edwards, Auckland (NZ); Gavin Walsh Millar, Auckland (NZ); Helgard Oosthuysen, Auckland (NZ); Andre van Schalkwyk, Auckland (NZ); Ian Lee Wai Kwan, Auckland (NZ); Ping Si, Auckland (NZ); Sinaa Alnashi, Auckland (NZ); Kieran Michael Orchard, Hawera (NZ); Ibrahim Al-Tiay, Auckland (NZ); Elmo Benson Stoks, Auckland (NZ); Charles Christopher North, Auckland (NZ); Matthew Robert Wilson, Auckland (NZ); Paul James Tonkin, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 394 days.

(21) Appl. No.: 14/442,688

(22) PCT Filed: Nov. 14, 2013

(86) PCT No.: PCT/NZ2013/000208
§ 371 (c)(1),
(2) Date: May 13, 2015

(87) PCT Pub. No.: WO2014/077706
PCT Pub. Date: May 22, 2014

(65) Prior Publication Data
US 2016/0354573 A1    Dec. 8, 2016

Related U.S. Application Data

(60) Provisional application No. 61/726,532, filed on Nov. 14, 2012, provisional application No. 61/786,141, (Continued)

(51) Int. Cl.
*A61M 16/00* (2006.01)
*A61M 16/08* (2006.01)
(Continued)

(52) U.S. Cl.
CPC ......... *A61M 16/1095* (2014.02); *A61G 11/00* (2013.01); *A61M 16/024* (2017.08);
(Continued)

(58) Field of Classification Search
CPC .......... A61M 16/1095; A61M 16/1075; A61M 16/0816; A61M 16/0866; A61M 16/161;
(Continued)

(56) References Cited

U.S. PATENT DOCUMENTS

| 485,127 A | 10/1892 | Lynch |
| 2,073,335 A | 3/1937 | Connell |

(Continued)

FOREIGN PATENT DOCUMENTS

| AU | 1448473 | 9/1976 |
| AU | 2007317198 | 5/2008 |

(Continued)

OTHER PUBLICATIONS

International Preliminary Report on Patentability in corresponding International Patent Application No. PCT/NZ2013/000208, dated May 19, 2015, in 8 pages.

(Continued)

*Primary Examiner* — Colin W Stuart
*Assistant Examiner* — Douglas Y Sul
(74) *Attorney, Agent, or Firm* — Knobbe, Martens, Olson & Bear, LLP

(57) ABSTRACT

Some embodiments provide for an inspiratory limb for a breathing circuit that includes a first segment that comprises a first heater wire circuit and a second segment that comprises a second heater wire circuit. The inspiratory limb can include an intermediate connector that includes a connection circuit that electrically couples the first heater wire circuit to the second heater wire circuit. The inspiratory limb can be configured to operate in two modes wherein, in a first mode, electrical power passes through the first electrical connection to provide power to the first heater wire circuit without providing power to the second heater wire circuit, and in a second mode, electrical power pass through the first electrical connection to provide power to both the first heater wire circuit and the second heater wire circuit.

23 Claims, 31 Drawing Sheets

Related U.S. Application Data filed on Mar. 14, 2013, provisional application No. 61/877,736, filed on Sep. 13, 2013, provisional application No. 61/877,784, filed on Sep. 13, 2013, provisional application No. 61/877,622, filed on Sep. 13, 2013, provisional application No. 61/877,566, filed on Sep. 13, 2013.

(51) Int. Cl.
  A61M 16/10 (2006.01)
  A61G 11/00 (2006.01)
  A61M 16/16 (2006.01)

(52) U.S. Cl.
  CPC .... *A61M 16/0816* (2013.01); *A61M 16/0866* (2014.02); *A61M 16/0875* (2013.01); *A61M 16/16* (2013.01); *A61M 16/161* (2014.02); *A61G 2210/70* (2013.01); *A61G 2210/90* (2013.01); *A61M 2016/0033* (2013.01); *A61M 2016/1025* (2013.01); *A61M 2205/3368* (2013.01); *A61M 2205/3653* (2013.01); *A61M 2205/50* (2013.01); *A61M 2209/082* (2013.01)

(58) Field of Classification Search
  CPC .. A61M 2205/3368; A61M 2205/3653; A61M 16/0875; A61M 16/08; F16L 11/15; F16L 11/16; F16L 11/1185
  USPC ............................. 138/122, 127, 133, 138
  See application file for complete search history.

(56) References Cited

U.S. PATENT DOCUMENTS

| | | |
|---|---|---|
| 2,516,864 A | 8/1950 | Gilmore et al. |
| 2,788,936 A | 4/1957 | Kemnitz |
| 2,874,722 A | 2/1959 | Hamblin |
| 3,117,596 A | 1/1964 | Khan |
| 3,163,707 A | 12/1964 | Darling |
| 3,283,580 A | 11/1966 | Jacob et al. |
| 3,394,954 A | 7/1968 | Sarns |
| 3,495,628 A | 2/1970 | Boender |
| 3,582,968 A | 6/1971 | Buiting |
| 3,584,193 A | 6/1971 | Badertscher |
| 3,638,926 A | 2/1972 | Melville et al. |
| 3,695,267 A | 10/1972 | Hirtz et al. |
| 3,766,914 A | 10/1973 | Jacobs |
| 3,914,349 A | 10/1975 | Stipanuk |
| 3,926,223 A | 12/1975 | Petzetakis |
| 3,963,856 A | 6/1976 | Carlson et al. |
| 3,990,727 A | 11/1976 | Gallagher |
| 4,013,122 A | 3/1977 | Long |
| 4,013,742 A | 3/1977 | Lang |
| 4,033,808 A | 7/1977 | Petzetakis |
| 4,038,519 A | 7/1977 | Foucras |
| 4,038,980 A | 8/1977 | Fodor |
| 4,051,205 A | 9/1977 | Grant |
| 4,060,576 A | 11/1977 | Grant |
| 4,110,419 A | 8/1978 | Miller |
| 4,111,197 A | 9/1978 | Warncke et al. |
| 4,160,466 A | 7/1979 | Jousson |
| 4,172,105 A | 10/1979 | Miller et al. |
| 4,301,200 A | 11/1981 | Langenfeld |
| 4,333,451 A | 6/1982 | Paluch |
| 4,428,403 A | 1/1984 | Lee et al. |
| 4,430,994 A | 2/1984 | Clawson et al. |
| 4,487,232 A | 12/1984 | Kanao |
| 4,490,575 A | 12/1984 | Kutnyak |
| 4,500,480 A | 2/1985 | Cambio, Jr. |
| 4,529,867 A | 7/1985 | Velnosky et al. |
| 4,531,551 A | 7/1985 | Eichelberger et al. |
| 4,553,023 A | 11/1985 | Jameson et al. |
| 4,574,188 A | 3/1986 | Midgley et al. |
| 4,597,917 A | 7/1986 | Lunsford |
| 4,621,632 A | 11/1986 | Bartels et al. |
| 4,640,804 A | 2/1987 | Mizoguchi |
| 4,676,237 A | 6/1987 | Wood et al. |
| 4,684,786 A | 8/1987 | Mann et al. |
| 4,686,354 A | 8/1987 | Makin |
| 4,695,955 A | 9/1987 | Faisandier |
| 4,708,831 A | 11/1987 | Elsworth et al. |
| 4,710,887 A | 12/1987 | Ho |
| 4,722,334 A | 2/1988 | Blackmer et al. |
| 4,753,758 A | 6/1988 | Miller |
| 4,780,247 A | 10/1988 | Yasuda |
| 4,829,781 A | 5/1989 | Hitzler |
| 4,829,997 A | 5/1989 | Douwens et al. |
| 4,829,998 A | 5/1989 | Jackson |
| 4,844,512 A | 7/1989 | Gahwiler |
| 4,861,523 A | 8/1989 | Beran |
| 4,903,736 A | 2/1990 | Baston et al. |
| 4,911,157 A | 3/1990 | Miller |
| 4,911,357 A | 3/1990 | Kitamura |
| 4,921,642 A | 5/1990 | LaTorraca |
| 4,941,469 A | 7/1990 | Adahan |
| 4,967,744 A | 11/1990 | Chua |
| 5,031,612 A | 7/1991 | Clementi |
| 5,062,145 A | 10/1991 | Zwaan et al. |
| 5,092,326 A | 3/1992 | Winn et al. |
| 5,101,820 A | 4/1992 | Christopher |
| 5,127,442 A | 7/1992 | Blomqvist |
| 5,148,801 A | 9/1992 | Douwens et al. |
| 5,164,652 A | 11/1992 | Johnson et al. |
| 5,213,376 A | 5/1993 | Szabo |
| 5,224,923 A | 7/1993 | Moffett et al. |
| 5,230,331 A | 7/1993 | Rusz et al. |
| 5,231,979 A | 8/1993 | Rose et al. |
| 5,336,156 A | 8/1994 | Miller et al. |
| 5,346,128 A | 9/1994 | Wacker |
| 5,347,211 A | 9/1994 | Jakubowski |
| 5,367,604 A | 11/1994 | Murray |
| 5,388,443 A | 2/1995 | Manaka |
| 5,392,770 A | 2/1995 | Clawson et al. |
| 5,404,729 A | 4/1995 | Matsuoka et al. |
| 5,405,269 A | 4/1995 | Stupecky |
| 5,428,752 A | 6/1995 | Goren et al. |
| 5,449,234 A | 9/1995 | Gipp et al. |
| 5,454,061 A | 9/1995 | Carlson |
| 5,482,031 A | 1/1996 | Lambert |
| 5,516,466 A | 5/1996 | Schlesch et al. |
| 5,529,060 A | 6/1996 | Salmon et al. |
| 5,537,996 A | 7/1996 | McPhee |
| 5,551,731 A | 9/1996 | Gray et al. |
| 5,558,084 A | 9/1996 | Daniell et al. |
| 5,564,415 A | 10/1996 | Dobson et al. |
| 5,588,423 A | 12/1996 | Smith |
| 5,591,292 A | 1/1997 | Blomqvist |
| 5,600,752 A | 2/1997 | Lopatinsky |
| 5,630,806 A | 5/1997 | Inagaki |

(56) References Cited

U.S. PATENT DOCUMENTS

| | | | |
|---|---|---|---|
| 5,637,168 A | 6/1997 | Carlson | |
| 5,640,951 A * | 6/1997 | Huddart | A61M 16/08 |
| | | | 128/204.17 |
| 5,673,687 A | 10/1997 | Dobson et al. | |
| 5,759,149 A | 6/1998 | Goldberg et al. | |
| 5,769,071 A | 6/1998 | Turnbull | |
| 5,778,872 A | 7/1998 | Fukunaga et al. | |
| 5,848,223 A | 12/1998 | Carlson | |
| 5,906,201 A | 5/1999 | Nilson | |
| 5,943,473 A | 8/1999 | Levine | |
| 5,988,164 A | 11/1999 | Paluch | |
| 5,991,507 A | 11/1999 | Bencsits | |
| 6,010,118 A | 1/2000 | Milewicz | |
| 6,024,694 A | 2/2000 | Goldberg et al. | |
| 6,038,457 A | 3/2000 | Barkat | |
| 6,050,260 A | 4/2000 | Daniell et al. | |
| 6,078,730 A | 6/2000 | Huddart et al. | |
| 6,095,505 A | 8/2000 | Miller | |
| 6,105,649 A | 8/2000 | Levingston et al. | |
| 6,109,782 A | 8/2000 | Fukura et al. | |
| 6,125,847 A | 10/2000 | Lin | |
| 6,138,674 A | 10/2000 | Gull et al. | |
| 6,142,974 A * | 11/2000 | Kistner | A61M 5/44 |
| | | | 392/479 |
| 6,158,431 A | 12/2000 | Poole | |
| 6,167,883 B1 | 1/2001 | Beran et al. | |
| 6,189,870 B1 | 2/2001 | Withall | |
| 6,190,480 B1 | 2/2001 | Carlson | |
| 6,219,490 B1 | 4/2001 | Gibertoni et al. | |
| 6,272,933 B1 | 8/2001 | Gradon et al. | |
| 6,311,958 B1 | 11/2001 | Stanek | |
| 6,347,646 B2 | 2/2002 | Fukui et al. | |
| 6,349,722 B1 | 2/2002 | Gradon et al. | |
| 6,367,472 B1 | 4/2002 | Koch | |
| 6,367,510 B1 | 4/2002 | Carlson | |
| 6,374,864 B1 | 4/2002 | Philip | |
| 6,384,755 B1 | 5/2002 | Hayden | |
| 6,394,084 B1 | 5/2002 | Nitta | |
| 6,394,145 B1 | 5/2002 | Bailly | |
| 6,397,841 B1 | 6/2002 | Kenyon et al. | |
| 6,397,846 B1 | 6/2002 | Skog et al. | |
| 6,398,197 B1 | 6/2002 | Dickinson et al. | |
| 6,463,925 B2 | 10/2002 | Nuckols et al. | |
| 6,474,335 B1 | 11/2002 | Lammers | |
| 6,537,405 B1 | 3/2003 | Henderson et al. | |
| 6,540,734 B1 | 4/2003 | Chiu et al. | |
| 6,543,412 B2 | 4/2003 | Amou et al. | |
| 6,564,011 B1 | 5/2003 | Janoff et al. | |
| 6,584,972 B2 | 7/2003 | McPhee | |
| 6,594,366 B1 | 7/2003 | Adams | |
| 6,668,828 B1 | 12/2003 | Figley et al. | |
| 6,691,707 B1 | 2/2004 | Gunaratnam et al. | |
| 6,694,974 B1 | 2/2004 | George-Gradon et al. | |
| 6,718,974 B1 | 4/2004 | Moberg | |
| 6,827,109 B2 | 12/2004 | Mccaughtry | |
| 6,918,389 B2 | 7/2005 | Seakins et al. | |
| 6,932,119 B2 | 8/2005 | Carlson | |
| 6,953,354 B2 | 10/2005 | Edirisuriya et al. | |
| 7,086,422 B2 | 8/2006 | Huber et al. | |
| 7,096,864 B1 | 8/2006 | Mayer et al. | |
| 7,120,354 B2 | 10/2006 | Mackie et al. | |
| 7,156,127 B2 | 1/2007 | Moulton et al. | |
| 7,157,035 B2 | 1/2007 | Edirisuriya et al. | |
| 7,291,240 B2 | 11/2007 | Smith et al. | |
| 7,468,116 B2 | 12/2008 | Smith et al. | |
| 7,588,029 B2 | 9/2009 | Smith et al. | |
| 7,588,186 B2 | 9/2009 | Steffen et al. | |
| 7,637,288 B2 | 12/2009 | Huber et al. | |
| 7,647,926 B2 | 1/2010 | Gerder et al. | |
| 7,766,050 B2 | 8/2010 | Patel | |
| 7,814,907 B2 | 10/2010 | Bremner et al. | |
| 7,965,930 B2 | 6/2011 | Carlson et al. | |
| 7,997,267 B2 | 8/2011 | Ging et al. | |
| 8,091,547 B2 | 1/2012 | Thudor et al. | |
| 8,122,882 B2 | 2/2012 | McGhin et al. | |
| 8,186,345 B2 | 5/2012 | Payton et al. | |
| 8,235,041 B2 | 8/2012 | Seakins et al. | |
| 8,333,194 B2 | 12/2012 | Lewis et al. | |
| 8,333,199 B2 | 12/2012 | Landis et al. | |
| 8,360,059 B2 | 1/2013 | Koulechov et al. | |
| 8,453,641 B2 | 6/2013 | Payton et al. | |
| 8,459,259 B2 | 6/2013 | Klasek et al. | |
| 8,469,025 B2 | 6/2013 | Mayer et al. | |
| 8,522,782 B2 | 9/2013 | Lewis et al. | |
| 8,563,863 B2 | 10/2013 | Carlson | |
| 8,563,864 B2 | 10/2013 | Carlson | |
| 8,631,789 B2 | 1/2014 | Virr et al. | |
| 8,709,187 B2 | 4/2014 | Smith et al. | |
| 8,733,349 B2 | 5/2014 | Bath et al. | |
| 8,844,522 B2 | 9/2014 | Huby et al. | |
| 9,119,933 B2 | 9/2015 | Bedford et al. | |
| 9,440,040 B2 | 9/2016 | Klasek et al. | |
| 9,517,321 B2 | 12/2016 | Buechi et al. | |
| 9,555,210 B2 | 1/2017 | Seakins et al. | |
| 9,572,949 B2 | 2/2017 | Vos et al. | |
| 9,855,398 B2 | 1/2018 | Klasek et al. | |
| 10,080,866 B2 | 9/2018 | Stoks et al. | |
| 2001/0017134 A1 * | 8/2001 | Bahr | A61M 16/0816 |
| | | | 128/204.18 |
| 2001/0050080 A1 | 12/2001 | Seakins et al. | |
| 2002/0038392 A1 | 3/2002 | De La Huerga | |
| 2002/0120236 A1 * | 8/2002 | Diaz | A61M 5/14216 |
| | | | 604/151 |
| 2002/0124847 A1 | 9/2002 | Smith et al. | |
| 2002/0173717 A1 | 11/2002 | Rohling et al. | |
| 2002/0186966 A1 | 12/2002 | Zimmer et al. | |
| 2003/0059213 A1 | 3/2003 | Mackie et al. | |
| 2003/0183294 A1 | 10/2003 | Carlson | |
| 2003/0236015 A1 | 12/2003 | Edirisuriya et al. | |
| 2004/0074493 A1 | 4/2004 | Seakins et al. | |
| 2004/0074495 A1 | 4/2004 | Wickham et al. | |
| 2004/0079371 A1 | 4/2004 | Gray | |
| 2004/0081784 A1 | 4/2004 | Smith et al. | |
| 2004/0099268 A1 | 5/2004 | Smith et al. | |
| 2004/0101026 A1 | 5/2004 | Nitta et al. | |
| 2004/0149284 A1 | 8/2004 | Smith et al. | |
| 2004/0182392 A1 * | 9/2004 | Gerder | A61M 16/08 |
| | | | 128/204.22 |
| 2004/0244858 A1 | 12/2004 | Jeong | |
| 2005/0059957 A1 | 6/2005 | Byerly et al. | |
| 2005/0152733 A1 | 7/2005 | Patel | |
| 2006/0165829 A1 | 7/2006 | Smith et al. | |
| 2006/0283447 A1 * | 12/2006 | Dhuper | A61M 16/08 |
| | | | 128/203.12 |
| 2007/0047733 A1 | 3/2007 | Bremer et al. | |
| 2007/0051368 A1 | 3/2007 | Seakins et al. | |
| 2007/0079982 A1 | 4/2007 | Laurent et al. | |
| 2007/0107737 A1 | 5/2007 | Landis et al. | |
| 2007/0277828 A1 | 12/2007 | Ho et al. | |
| 2008/0078259 A1 | 4/2008 | Duff | |
| 2008/0105257 A1 * | 5/2008 | Klasek | A61M 16/0633 |
| | | | 128/203.27 |
| 2008/0173305 A1 | 7/2008 | Frater | |
| 2008/0202512 A1 | 8/2008 | Kressierer/Huber et al. | |
| 2008/0251073 A1 | 10/2008 | Jassell et al. | |
| 2008/0264413 A1 | 10/2008 | Doherty et al. | |
| 2009/0078259 A1 | 3/2009 | Kooij et al. | |
| 2009/0078440 A1 | 3/2009 | Carlson et al. | |
| 2009/0110379 A1 | 4/2009 | McGhin et al. | |
| 2009/0126817 A1 | 5/2009 | Gray | |
| 2009/0149696 A1 | 6/2009 | Chilton, III | |
| 2009/0320840 A1 | 12/2009 | Klasek et al. | |
| 2010/0083965 A1 * | 4/2010 | Virr | A61M 16/0875 |
| | | | 128/203.26 |
| 2010/0116272 A1 | 5/2010 | Row et al. | |
| 2010/0224276 A1 | 9/2010 | Forrester et al. | |
| 2011/0046494 A1 | 2/2011 | Balji et al. | |
| 2011/0155132 A1 | 6/2011 | Virr et al. | |
| 2011/0168287 A1 | 7/2011 | Carlson | |
| 2012/0125333 A1 * | 5/2012 | Bedford | A61M 16/06 |
| | | | 128/203.25 |
| 2012/0255758 A1 | 10/2012 | Lee | |
| 2013/0104888 A1 | 5/2013 | Landis et al. | |
| 2013/0104901 A1 | 5/2013 | Landis et al. | |

(56) References Cited

U.S. PATENT DOCUMENTS

| | | |
|---|---|---|
| 2013/0174839 A1 | 7/2013 | Ging et al. |
| 2013/0239966 A1 | 9/2013 | Klasek et al. |
| 2013/0255677 A1 | 10/2013 | Varga |
| 2013/0280055 A1 | 10/2013 | Daly et al. |
| 2013/0340752 A1 | 12/2013 | Landis et al. |
| 2014/0037276 A1 | 2/2014 | Carlson |
| 2014/0130802 A1 | 5/2014 | Virr et al. |
| 2014/0202460 A1 | 7/2014 | Bath et al. |
| 2014/0216459 A1 | 8/2014 | Vos et al. |
| 2014/0246021 A1 | 9/2014 | Buechi et al. |
| 2014/0311487 A1 | 10/2014 | Buechi et al. |
| 2014/0318536 A1 | 10/2014 | Landis et al. |
| 2014/0366876 A1 | 12/2014 | Huby et al. |
| 2015/0090260 A1 | 4/2015 | Seakins et al. |
| 2015/0306333 A1 | 10/2015 | Amadio et al. |
| 2016/0256657 A1 | 9/2016 | Klasek et al. |
| 2016/0271356 A1 | 9/2016 | Robertson et al. |
| 2016/0354573 A1 | 12/2016 | Buswell et al. |
| 2017/0100556 A1 | 4/2017 | Munkelt et al. |
| 2018/0280651 A1 | 10/2018 | Liu et al. |
| 2019/0076620 A1 | 3/2019 | Stoks et al. |

FOREIGN PATENT DOCUMENTS

| | | | |
|---|---|---|---|
| DE | 36 29 353 | 1/1988 | |
| DE | 4020522 A1 | 1/1992 | |
| DE | 40 34 611 | 5/1992 | |
| DE | 4102223 A1 | 7/1992 | |
| DE | 33 11 811 | 10/1994 | |
| DE | 94 09 231.1 | 12/1994 | |
| DE | 19647548 A1 | 5/1998 | |
| DE | 20202906 U1 | 5/2002 | |
| DE | 202006007397 U1 * | 9/2007 | ............ A61M 16/08 |
| DE | 102007003454 | 7/2008 | |
| DE | 102007003454 A1 * | 7/2008 | ............ A61M 16/08 |
| DE | 102007003455 A1 | 8/2008 | |
| DE | 202007018764 U1 | 6/2009 | |
| DE | 102011055439 A1 | 5/2013 | |
| EP | 0201985 | 11/1986 | |
| EP | 0232864 A2 | 8/1987 | |
| EP | 0 258 928 | 9/1988 | |
| EP | 0342802 | 11/1989 | |
| EP | 0 481 459 | 4/1992 | |
| EP | 0 556 561 | 8/1993 | |
| EP | 616 166 | 9/1994 | |
| EP | 0621050 A2 | 10/1994 | |
| EP | 0 672 430 | 9/1995 | |
| EP | 0 885 623 | 12/1998 | |
| EP | 1078645 | 2/2001 | |
| EP | 1127583 | 8/2001 | |
| EP | 1 138 341 | 10/2001 | |
| EP | 1147004 B1 | 2/2003 | |
| EP | 1380276 A1 | 1/2004 | |
| EP | 1396277 A2 | 3/2004 | |
| EP | 1535722 A2 | 6/2005 | |
| EP | 1579984 A2 | 9/2005 | |
| EP | 2075026 A1 | 7/2009 | |
| EP | 2269680 A1 | 1/2011 | |
| EP | 2133611 B1 | 9/2011 | |
| EP | 2269680 | 9/2012 | |
| EP | 2514478 | 7/2013 | |
| GB | 1 167 551 | 10/1969 | |
| GB | 2056611 | 3/1981 | |
| GB | 2173274 A | 10/1986 | |
| GB | 2 277 689 | 11/1994 | |
| JP | S56-109189 U | 8/1981 | |
| JP | 05-317428 | 12/1993 | |
| JP | 08-061731 | 3/1996 | |
| JP | H08-109984 A | 4/1996 | |
| JP | H09-234247 | 9/1997 | |
| JP | H09-276408 | 10/1997 | |
| JP | H11-33119 A | 2/1999 | |
| JP | 2001-129091 | 5/2001 | |
| JP | 4422293 B2 | 2/2010 | |
| NZ | 579384 | 5/2011 | |
| NZ | 587113 | 12/2011 | |
| NZ | 589766 | 5/2012 | |
| NZ | 575837 | 7/2012 | |
| NZ | 583968 | 10/2012 | |
| NZ | 597827 | 6/2013 | |
| NZ | 590924 | 8/2013 | |
| NZ | 600986 | 8/2013 | |
| NZ | 597179 | 9/2013 | |
| NZ | 605324 | 6/2014 | |
| NZ | 605326 | 7/2014 | |
| NZ | 607629 | 7/2014 | |
| NZ | 610299 | 11/2014 | |
| NZ | 701541 | 5/2015 | |
| NZ | 625795 | 6/2015 | |
| NZ | 620739 | 8/2015 | |
| NZ | 625605 | 4/2016 | |
| NZ | 710351 | 1/2017 | |
| NZ | 631008 | 7/2017 | |
| SU | 379270 | 4/1973 | |
| WO | WO 92/21163 A1 | 11/1992 | |
| WO | WO 1996/020748 A1 | 7/1996 | |
| WO | WO 97/18001 | 5/1997 | |
| WO | WO 97/18001 A1 | 5/1997 | |
| WO | WO 98/26826 | 6/1998 | |
| WO | WO 01/10489 | 2/2001 | |
| WO | WO 02/32486 | 4/2002 | |
| WO | WO 2003/022342 | 3/2003 | |
| WO | WO 2003/026721 A2 | 4/2003 | |
| WO | WO 2004/024429 A1 | 3/2004 | |
| WO | WO 2004/039444 A1 | 5/2004 | |
| WO | WO 2004/105847 | 12/2004 | |
| WO | WO 2004/105848 A1 | 12/2004 | |
| WO | WO 2005/021076 A2 | 3/2005 | |
| WO | WO 2006/092001 A1 | 9/2006 | |
| WO | WO 2006/095151 | 9/2006 | |
| WO | WO 2007/051230 A1 | 5/2007 | |
| WO | WO 2008/055308 A1 | 5/2008 | |
| WO | WO 2008/060046 A1 | 5/2008 | |
| WO | WO 2008/060295 | 5/2008 | |
| WO | WO 2008/076230 | 6/2008 | |
| WO | WO 2009/015410 | 2/2009 | |
| WO | WO 2009/015410 A1 | 2/2009 | |
| WO | WO 2009/022004 A2 | 2/2009 | |
| WO | WO 2010/084183 A2 | 7/2010 | |
| WO | WO 2011/051837 | 5/2011 | |
| WO | WO 2011/051837 A1 | 5/2011 | |
| WO | WO 2011/051870 A1 | 5/2011 | |
| WO | WO 2011/136665 A1 | 11/2011 | |
| WO | WO 2011/162622 A1 | 12/2011 | |
| WO | WO 2012/053910 A1 | 4/2012 | |
| WO | WO 2012/164407 A1 | 12/2012 | |
| WO | WO 2013/045575 | 4/2013 | |
| WO | WO 2013/127474 | 9/2013 | |
| WO | WO 2013/137753 A1 | 9/2013 | |
| WO | WO 2013/147623 A1 | 10/2013 | |
| WO | WO 2013/165263 A1 | 11/2013 | |
| WO | WO 2014/025266 | 2/2014 | |
| WO | WO 2014/077706 A1 | 5/2014 | |
| WO | WO 2014/088430 A1 | 6/2014 | |
| WO | WO 2014/205513 | 12/2014 | |
| WO | WO 2015/038013 A1 | 3/2015 | |
| WO | WO 2015/142192 | 9/2015 | |
| WO | WO 2017/043981 A1 | 3/2017 | |
| WO | WO 2018/116187 | 6/2018 | |

OTHER PUBLICATIONS

MR810 Respiratory Humidifier Technical Manual, Revision C.
Fisher & Paykel Healthcare, Annual Report 2003.
Fisher & Paykel Healthcare, FY04 Full Year Ovierview & Update, May 24, 2004.
Fisher & Paykel Healthcare, Full Year Analyst Briefing, Jun. 5, 2002.
MR850 Respiratory Humidifier Instruction Sheet, Rev. G, Feb. 2004.

* cited by examiner

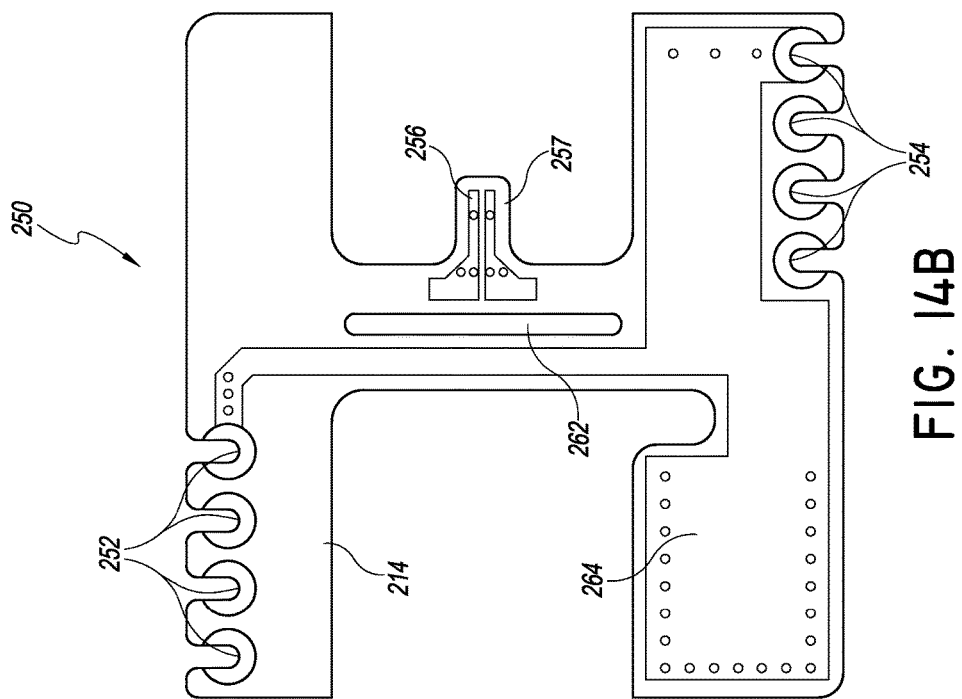
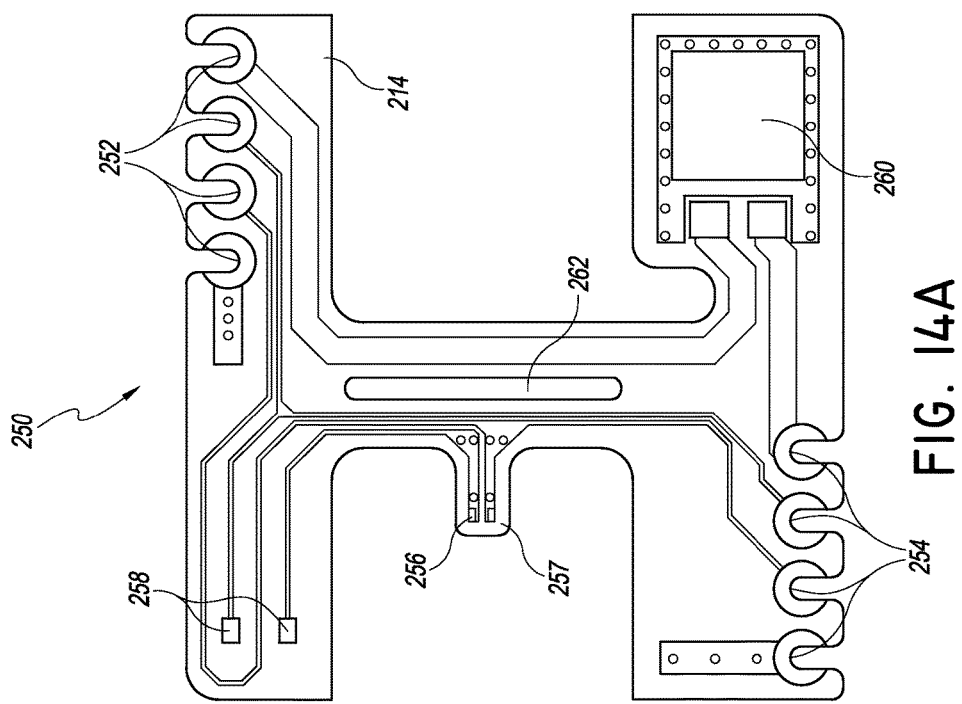

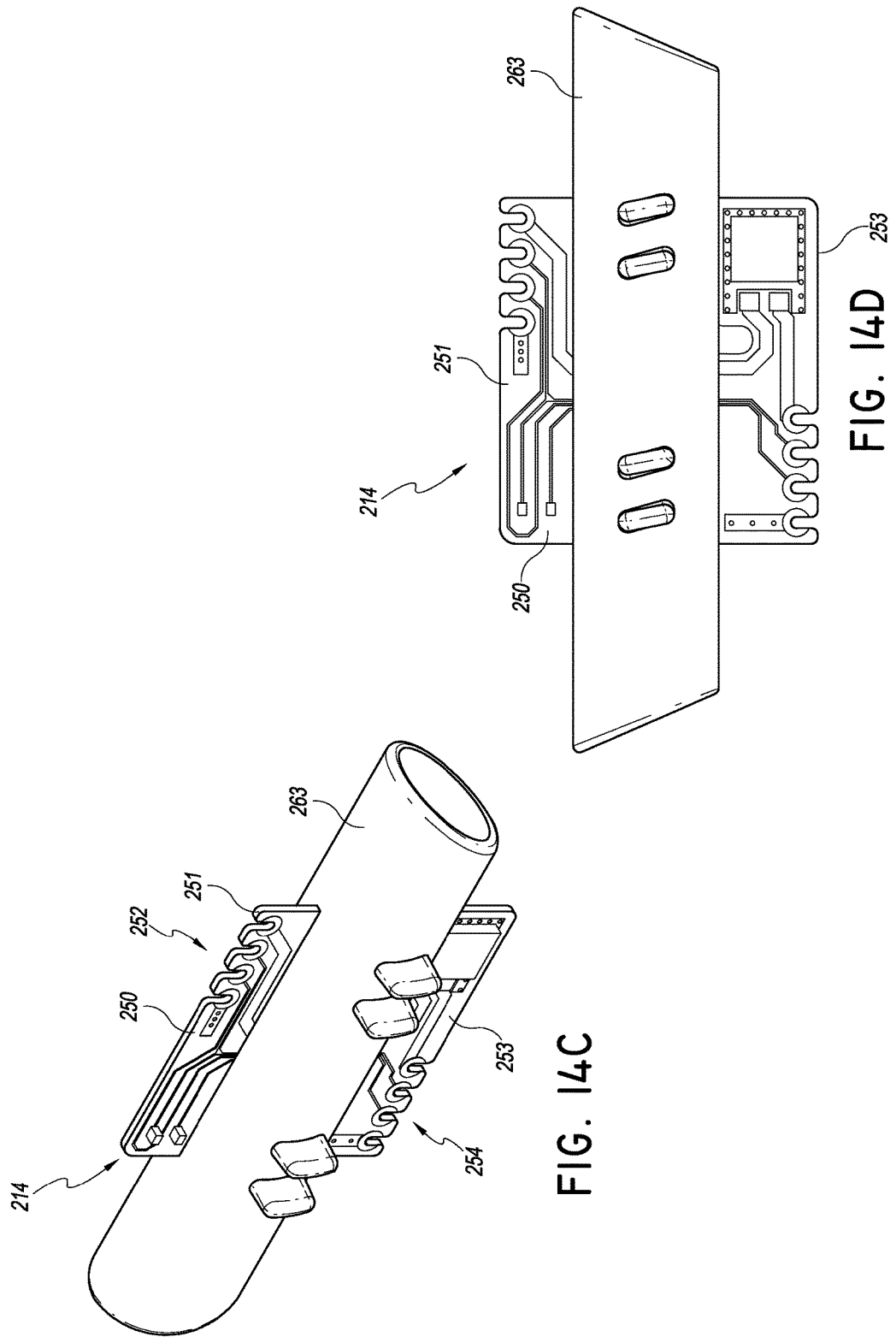

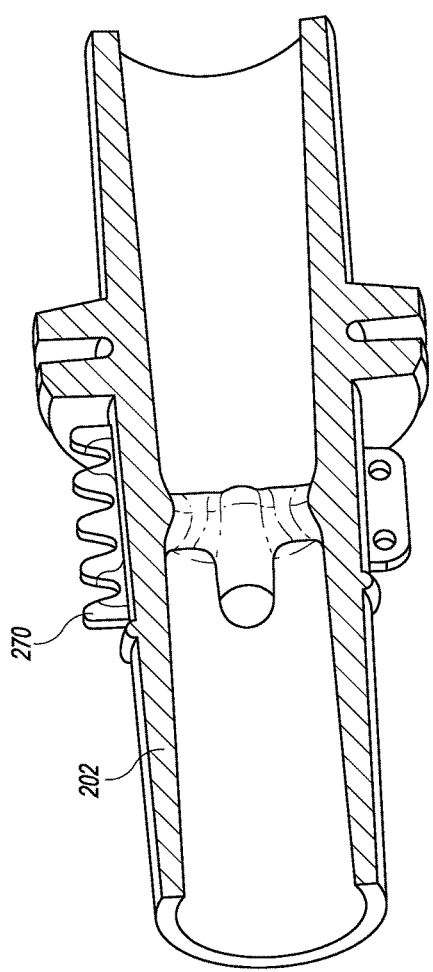
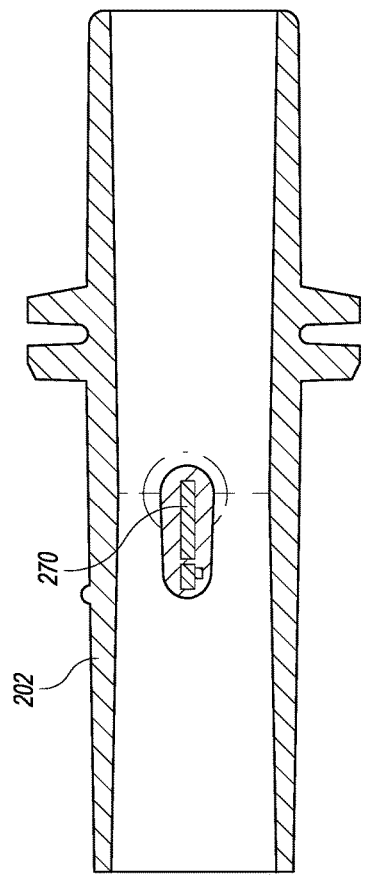
FIG. 15D
FIG. 15E

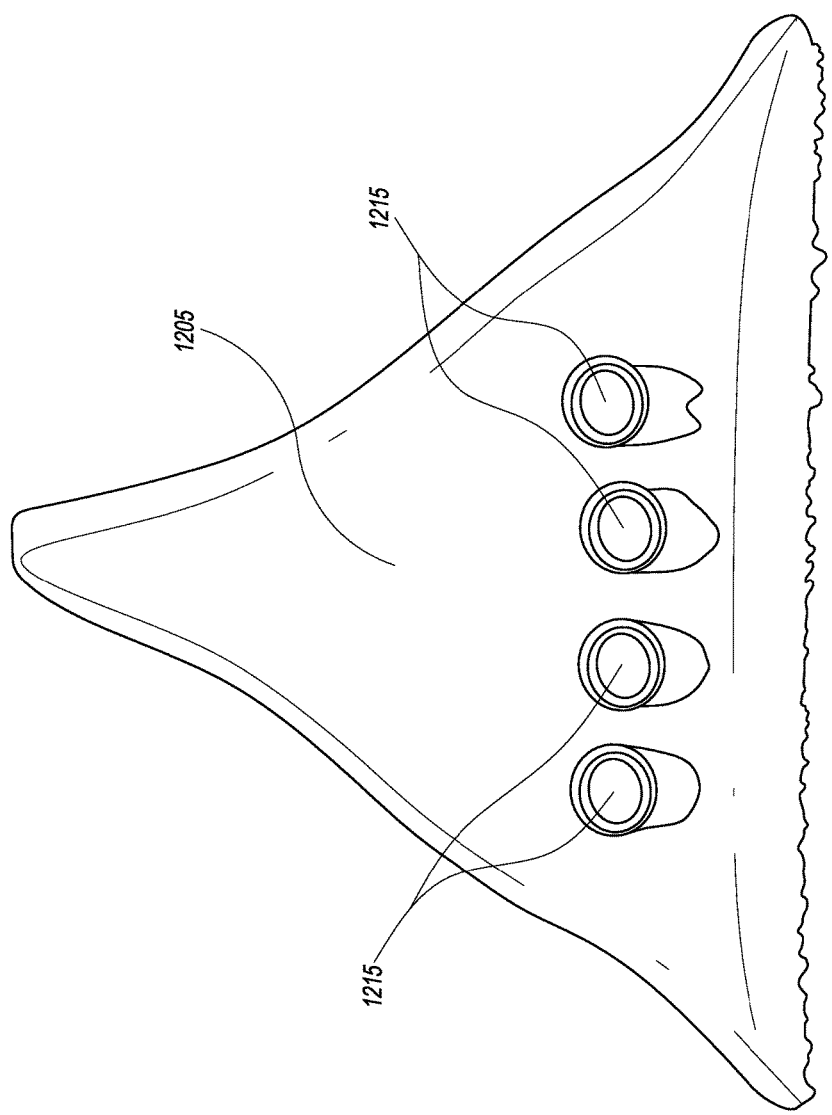

ZONE HEATING FOR RESPIRATORY CIRCUITS

INCORPORATION BY REFERENCE

This application claims the benefit of priority under 35 U.S.C. § 119(e) to U.S. Provisional Application No. 61/726,532 entitled "ZONE HEATING FOR RESPIRATORY CIRCUITS," filed Nov. 14, 2012; U.S. Provisional Application No. 61/786,141 entitled "ZONE HEATING FOR RESPIRATORY CIRCUITS," filed Mar. 14, 2013; U.S. Provisional Application No. 61/877,736 entitled "ZONE HEATING FOR RESPIRATORY CIRCUITS," filed Sep. 13, 2013; U.S. Provisional Application No. 61/877,784 entitled "CONNECTIONS FOR HUMIDICATION SYSTEM," filed Sep. 13, 2013; U.S. Provisional Application No. 61/877,622 entitled "MEDICAL TUBES AND METHODS OF MANUFACTURE," filed Sep. 13, 2013; and U.S. Provisional Application No. 61/877,566 entitled "HUMIDIFICATION SYSTEM," filed Sep. 13, 2013, each of which is incorporated herein by reference in its entirety.

In addition, PCT Application No. PCT/IB2012/001786 entitled "MEDICAL TUBES AND METHODS OF MANUFACTURE," filed May 30, 2012 is also incorporated herein by reference in its entirety.

BACKGROUND

Field

The present disclosure generally relates to humidification systems for providing humidified gases to users, and more particularly to heating gases in respiratory circuits used with humidification systems.

Description of Related Art

Many gas humidification systems deliver heated and humidified gases for various medical procedures, including respiratory treatment, laparoscopy, and the like. These systems can be configured to control temperature, humidity and flow rates using feedback from sensors. To maintain desirable properties upon delivery to a user, a breathing circuit can have heaters associated with gas conduits where the heaters provide heat to the gas as it flows to and/or from the user. The conduit heaters can be controlled to provide heat to the gas so that the gas arrives to the user having desirable properties such as temperature and/or humidity. A humidification system can include a temperature sensor to provide feedback to a humidification controller which can adjust and/or modify power delivered to the conduit heaters to achieve a target temperature at a location along an associated conduit.

SUMMARY

The systems, methods and devices described herein have innovative aspects, no single one of which is indispensable or solely responsible for their desirable attributes. Without limiting the scope of the claims, some of the advantageous features will now be summarized.

Some embodiments provide for an inspiratory limb for a breathing circuit. The inspiratory limb described herein is particularly useful in situations where heated and humidified gasses must pass through two distinct environments. This can be a problem, for example, in infant incubators where the temperature is significantly higher than the surrounding environment or where a portion of the conduit delivering the gasses to the patient is under a blanket. The embodiments disclosed herein, however, can be used in any environment where heated and/or humidified gas is delivered to a patient and are not limited to uses where the inspiratory limb passes through two distinct environments.

The inspiratory limb can include a first segment of the inspiratory limb that comprises a first structure forming a conduit, the conduit configured to transport a humidified gas, and wherein the first segment of the inspiratory limb includes a first heater wire circuit. The inspiratory limb can include a second segment of the inspiratory limb that comprises a second structure forming a conduit configured to transport the humidified gas, wherein the second structure is configured to mechanically couple to the first structure of the first segment to form an extended conduit for the humidified gas and wherein the second segment of the inspiratory limb includes a second heater wire circuit. The inspiratory limb can include an intermediate connector that includes a connection circuit that electrically couples the first heater wire circuit to the second heater wire circuit, wherein the intermediate connector can be coupled to a patient-end of the first segment of the inspiratory limb and a chamber-end of the second segment of the inspiratory limb to form a single conduit for the humidified gases. The intermediate connector can be covered by a portion of the first segment of the inspiratory limb, a portion of the second segment of the inspiratory limb, or a portion of both the first and second segments of the inspiratory limb such that the intermediate connector is internal to the inspiratory limb.

The inspiratory limb can be configured to operate in two heating modes. In a first heating mode, electrical power passes through the intermediate connector to provide power to the first heater wire circuit without providing power to the second heater wire circuit. In a second heating mode, electrical power passes through the intermediate connector to provide power to both the first heater wire circuit and the second heater wire circuit. For example, the intermediate connector can include electrical components configured to direct electrical power along different paths based at least in part on a direction of current flow and/or a polarity of voltage. The intermediate connector can include conductive tracks which can provide a short (e.g., a direct electrical connection with no intervening electrical components) between one or more wires in the first heater wire circuit and one or more wires in the second heater wire circuit. The intermediate connector can include conductive tracks which electrically couple one or more wires in the first heater wire circuit to one or more wires in the second heater wire circuit, where the conductive tracks include electrical components such as, for example and without limitation, diodes, transistors, capacitors, resistors, logic gates, integrated circuits, or the like. In certain embodiments, the intermediate connector includes a diode electrically coupled to both the first heater wire circuit and the second heater wire circuit. In certain embodiments, the inspiratory limb can further comprise a first sensor circuit having a first sensor positioned at the intermediate connector. In certain embodiments, the inspiratory limb further comprises a second sensor circuit having a second sensor positioned at a patient-end connector, the patient-end connector being positioned at a patient-end of the second segment of the inspiratory limb. The inspiratory limb can be configured to operate in two sensing modes. In a first sensing mode, signals from the first sensor are received without receiving signals from the second sensor. In a second sensing mode, signals from the second sensor are received without receiving signals from the first sensor. In some embodiments, sensing includes receiving signals from both the first and second sensors in parallel. In such embodiments, an algorithm can determine a parameter measured by the first sensor based at least in part on the signals received in parallel from both the first and second sensors. In certain embodiments, the intermediate connector includes a diode electrically coupled to both the first sensor circuit and the second sensor circuit. The patient-end connector can be configured to provide electrical connections for the second sensor circuit. Similarly, the patient-end connector can be configured to provide electrical connections for the second heater wire circuit. The sensors can be temperature sensors, humidity sensors, flow sensors, or the like. The first and second sensors can be sensors configured to measure one or more parameters, such as temperature, humidity, flow rate, oxygen percentage, or the like. In some embodiments, the first and second sensors are configured to measure at least one like parameter (e.g., temperature, humidity, flow rate, etc.). In some embodiments, more than two sensors can be included and can be positioned at the intermediate connector and/or the patient-end connector.

Some embodiments provide for a respiratory humidification system with an inspiratory limb and a controller. The inspiratory limb can include a first segment having a first heater wire circuit, a second segment having a second heater wire circuit, an intermediate connector having a connector circuit configured to electrically couple the first heater wire circuit to the second heater wire circuit, a first sensor positioned at a patient-end of the first segment, and a second sensor positioned at a patient-end of the second segment. The controller can be adapted to selectively switch between a first mode and a second mode wherein in the first mode the controller provides electrical power to the first heater wire circuit through the connector circuit and in a second mode the controller provides electrical power to the first and second heater wire circuits. In certain embodiments, the respiratory humidification system switches between modes based at least in part on input from one or both sensors. In certain embodiments, the switching is done based at least in part on parameters including one or more of temperature, flow, humidity, power, or any combination of these. The parameters can be derived or obtained directly from the first sensor, the second sensor, or a combination of both sensors. In certain embodiments, the first and second modes are defined by a direction of current flow or a polarity of voltage provided by a power source. In some embodiments, the respiratory humidification system can include more than two sensors which provide input used to control heating of the inspiratory limb.

Some embodiments provide for a dual limb circuit that can include an inspiratory limb. Such an inspiratory limb can include a first segment having a first heater wire circuit, a second segment of the inspiratory limb having a second heater wire circuit, an intermediate connector having a connector circuit configured to electrically couple the first heater wire circuit to the second heater wire circuit, a first sensor positioned at a patient-end of the first segment, and a second sensor positioned at a patient-end of the second segment. The dual limb circuit can also include an expiratory limb with an expiratory heater wire circuit. The dual limb system can further include an interface connected to the inspiratory limb and the expiratory limb. The dual limb system can further include a controller adapted to selectively switch between a first mode and a second mode wherein in the first mode the controller provides electrical power to the first heater wire circuit through the connector circuit and in a second mode the controller provides electrical power to the first and second heater wire circuits. In certain embodiments, heating of the expiratory limb is performed using the expiratory heater wire circuit independent of the heating of the inspiratory limb using the first and second heater wire circuits. In certain embodiments, the expiratory limb is powered in parallel with the first heater wire circuit in the first segment of the inspiratory limb and/or in parallel with the first and second heater wire circuits. In certain embodiments, the expiratory limb can be designed to be powered in only the first mode, only the second mode, or in both the first mode and in the second mode. In certain embodiments, the interface is connected via a wye-piece. Any suitable patient interface can be incorporated. Patient interface is a broad term and is to be given its ordinary and customary meaning to a person of ordinary skill in the art (that is, it is not to be limited to a special or customized meaning) and includes, without limitation, masks (such as tracheal mask, face masks and nasal masks), cannulas, and nasal pillows.

In some embodiments, a segmented inspiratory limb is provided, wherein the structure of the segments comprise an elongate tube. The elongate tubes can include a first elongate member comprising a hollow body spirally wound to form at least in part a conduit having a longitudinal axis, a lumen extending along the longitudinal axis, and a hollow wall surrounding the lumen. The elongate tubes can include a second elongate member spirally wound and joined between adjacent turns of the first elongate member, the second elongate member forming at least a portion of the lumen of the elongate tube. In certain implementations, the first elongate member forms in longitudinal cross-section a plurality of bubbles with a flattened surface at the lumen. In certain implementations, adjacent bubbles are separated by a gap above the second elongate member. In certain implementations, adjacent bubbles are not directly connected to each other. In certain implementations, the plurality of bubbles has perforations.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIGS. 14A and 14B illustrate an example printed circuit board ("PCB") of an intermediate connector.

FIGS. 14C and 141) illustrate example embodiments of intermediate connectors.

FIGS. 15B-15E illustrate example embodiments of patient-end connectors.

FIG. 18G shows another example second elongate member.

DETAILED DESCRIPTION

Figure 1:
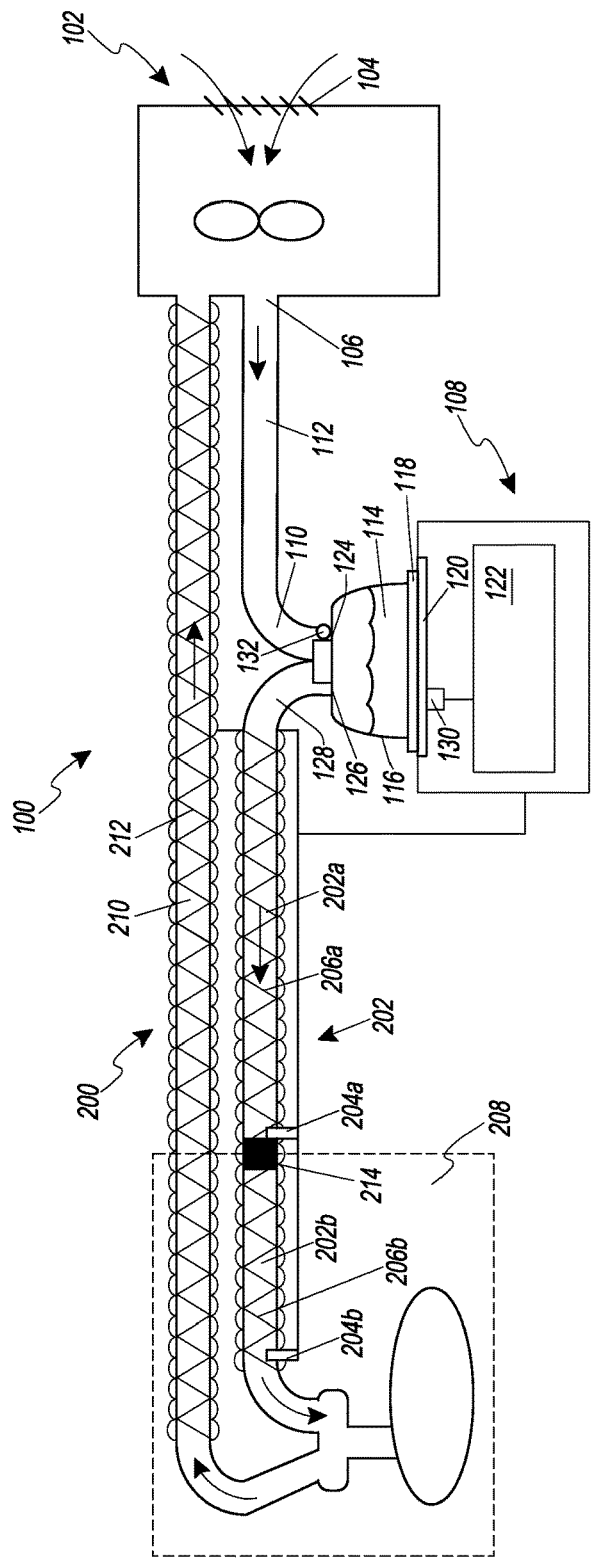
FIG. 1 illustrates an example respiratory humidification system for delivering humidified gas to a user, the respiratory humidification system having a breathing circuit that includes a segmented inspiratory limb with sensors in each segment.

Certain embodiments and examples of segmented inspiratory limbs and multiple-zone heating are described herein. Those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described herein.

Described herein are systems and methods for providing heat to a segmented inspiratory limb in a breathing circuit of a respiratory humidification system. It will be understood that although much of the description herein is in the context of segmented inspiratory limbs in breathing circuits, one or more features of the present disclosure can also be implemented in other scenarios where it is desirable to provide differential heating in segmented gas delivery conduits such as in respiratory, surgical, or other applications.

The disclosure references heater wires, heating elements, and/or heaters in the context of providing heat to a conduit. Heater wire, for example, is a broad term and is to be given its ordinary and customary meaning to a person of ordinary skill in the art (that is, it is not to be limited to a special or customized meaning) and includes, without limitation, heater strips and/or conductive elements that produce heat when electrical power is provided. Examples of such heating elements include wires made of a conductive metal (e.g., copper), conductive polymers, conductive inks printed on a surface of a conduit, conductive materials used to create a track on a conduit, and the like. Furthermore, the disclosure references conduits, limbs, and medical tubes in the context of gas delivery. Tube, for example, is a broad term and is to be given its ordinary and customary meaning to a person of ordinary skill in the art and includes, without limitation, passageways having a variety of cross-sections such as cylindrical and non-cylindrical passageways. Certain embodiments may incorporate a composite tube, which may generally be defined as a tube comprising two or more portions, or, specifically, in some embodiments, two or more components, as described in greater detail below. The segmented limbs comprising the disclosed medical tubes can also be used in breathing circuits such as a continuous, variable, or bi-level positive airway pressure (PAP) system or other form of respiratory therapy. The terms conduit and limb should be construed in a manner that is similar to tube.

When a heated, humidified breathing tube is used for an incubator (or any region where there is a temperature change, such as around radiant warmers used for burn victims, or under a blanket used by a patient), the breathing tube will pass through at least two distinct zones: a lower temperature zone (such as the one outside the incubator) and a higher temperature zone (such as the one inside the incubator). If the tube is heated along its full length, one of the zones will tend to be at an undesirable, unsuitable, or non-optimal temperature, depending on which zone is sensed (e.g., which zone contains a temperature sensor). If the heater wire is controlled to a sensor inside the incubator (such as to a patient-end temperature sensor), the section outside the incubator will tend to be too cool, which can lead to condensation. Conversely, if the heater wire is controlled to a sensor outside the incubator, the section inside the incubator will tend to be too hot, which can lead to overheated gas being provided to the patient. Accordingly, the present disclosure describes systems and methods that provide for control over heat in a segmented breathing tube wherein each segment has an associated sensor providing feedback to a control module. Although several embodiments are described herein with respect to two zones, such a system could also be extended to apply to uses with additional zones, segments, or regions. For example, in an embodiment comprising three temperature zones, segments of the breathing tube may be heated based at least in part on three different temperature sensors in the zones. Furthermore, the embodiments disclosed herein can control the heat delivered to a breathing tube based on a parameter at the patient-end, bypassing or ignoring one or more of the sensors at intermediate points along the tube. Moreover, the embodiments disclosed herein can control the heat delivered to a breathing tube using parameters provided by sensors including, for example and without limitation, temperature sensors, humidity sensors, flow sensors, oxygen sensors, and the like.

A control module can monitor and control the heating temperatures in multiple zones or sections. The control module can be configured to provide heat to a first section of the breathing tube in a first mode and to the entire breathing tube in a second mode using embodiments of connector assemblies described herein. The embodiments described herein can be used without flying leads, exposed connectors, and/or patient-end electrical connections. Flying leads as used herein include electrical connections that extend externally of the breathing tubes, internally through the breathing tubes, and incorporated, molded, or otherwise formed or included as part of the breathing tubes. The control module can be located within the humidifier or externally to it. In some embodiments, the controller is located within the humidifier to control the heater wires associated with a first segment of an inspiratory limb, a second segment of an inspiratory limb, and an expiratory limb as well as read parameters from sensors associated with the first and second segments of the inspiratory limb and/or the expiratory limb.

The control module can also adaptively change the temperature for the segments. For example, the control module can monitor temperature sensors associated with one or more segments. The monitoring can be continuous, based on intervals, or other schemes such as interrupt or event-based monitoring. For example, the monitoring of temperature sensors can be based on reading values from an analog to digital converter, determining a voltage or current, sensing a logic condition, reading thermostatic devices, measuring thermistor values, measuring resistance temperature detectors, measuring the voltage of a thermocouple, or other methods for sensing temperature, including, but not limited to the use of semiconductor junction sensor, infrared or thermal radiation sensors, thermometers, indicators, or the like. In some embodiments, the temperature sensors are thermistors.

In some embodiments, the ratio of the power delivered to the first segment of the inspiratory limb and the second segment of the inspiratory limb can change during use based at least in part on feedback from sensors associated with each segment. For example, the ratio of power can be changed in a manner such that each segment is heated to a temperature to reduce or eliminate condensation. As a further example, the ratio of power can be changed so that overheated gas is not provided to the patient. In some embodiments, the ratio of power can be continuously changed based on feedback from sensors (e.g., temperature sensors, humidity sensors, oxygen sensors, flow sensors, etc.). The ratio of power can be changed in different ways. For example, the ratio of power can be changed by altering the amplitude of a power signal (including, without limitation, the voltage and/or current), the duration of the power signal, the duty cycle of the power signal, or other suitable changes to the power signal. In an embodiment, the ratio of power is changed by altering the magnitude of the current provided.

Some embodiments provide for an inspiratory limb comprising heater wires that are not within the gas path, but are contained within a material that separates them from the gas path and that also insulates them from an external environment. In some embodiments, the circuitry used to provide power to heater wires in the segments and to read the sensors is internal to the inspiratory limb such that it is not exposed to the external environment. In some embodiments, the heater wire is molded into the inspiratory or expiratory tube such that the ends of the heater wires in complementary segments of the tube contact an intermediate connector such that the heater wires electrically couple to the intermediate connector, wherein the intermediate connector can be configured to provide circuitry for heater wire control and/or sensor readings. In some embodiments, a duty cycle of a power source applied to a heater wire can be modified or varied to alter an amount of heat delivered to a gas as it flows along the associated segment.

Some embodiments described herein provide for a respiratory humidification system that is configured to deliver warm, humidified gas to a patient or other user. The gas is passed through a liquid chamber which is filled with a liquid (e.g., water) that is heated using a heater plate. The liquid evaporates in the chamber and combines with the gas which flows over it, thereby heating and/or humidifying the gas. The humidified gas can be directed to an inspiratory limb having one or more heater wires associated therewith. The heater wires can be selectively powered to provide a defined, desired, appropriate, or selected amount of heat to the humidified gas. In some embodiments, the respiratory humidification system can be used in conjunction with an incubator or radiant warmer. The inspiratory limb can be segmented such that a first segment is outside the incubator and a second segment is inside the incubator. Furthermore, a first set of heater wires can be associated with the first segment and a second set of heater wires can be associated with the second segment. The humidification system can be configured to provide power to the first set of heater wires in a first mode and to the first set and second set of heater wires in a second mode. In some embodiments, the humidification system can be configured to provide power to the first set of heater wires in a first mode and to the second set of heater wires in a second mode. The inspiratory limb can include sensors at the end of each segment to provide feedback to the humidification system for use in selecting a power to deliver to the sets of heater wires in the segments. In some embodiments, the humidification system can include an expiratory limb having associated heater wires which are also selectively controlled by the humidification system. In this application, the segmented limb is described with reference to an inspiratory limb. However, the described features can be applied to an expiratory limb as well.

Respiratory Humidification Systems

FIG. 1 illustrates an example respiratory humidification system 100 for delivering humidified gas to a user, the respiratory humidification system 100 having a breathing circuit 200 that includes a segmented inspiratory limb 202 with sensors 204a, 204b in each segment. The segmented inspiratory limb 202 can be used in conjunction with an incubator 208, as illustrated, or with another system where there are different temperatures along different segments of the inspiratory limb 202, such as in conjunction with a radiant warmer. The segmented inspiratory limb 202 can be used to provide different levels of heat to different segments of the inspiratory limb 202a, 202b to reduce or prevent condensation and/or to control a temperature of gas delivered to a user.

The illustrated respiratory humidification system 100 comprises a pressurized gas source 102. In some implementations, the pressurized gas source 102 comprises a fan, blower, or the like. In some implementations, the pressurized gas source 102 comprises a ventilator or other positive pressure generating device. The pressurized gas source 102 comprises an inlet 104 and an outlet 106.

The pressurized gas source 102 provides a flow of fluid (e.g., oxygen, anesthetic gases, air or the like) to a humidification unit 108. The fluid flow passes from the outlet 106 of the pressurized gas source 102 to an inlet 110 of the humidification unit 108. In the illustrated configuration, the humidification unit 108 is shown separate of the pressurized gas source 102 with the inlet 110 of the humidification unit 108 connected to the outlet 106 of the pressurized gas source 102 with a conduit 112. In some implementations, the pressurized gas source 102 and the humidification unit 108 can be integrated into a single housing.

While other types of humidification units can be used with certain features, aspects, and advantages described in the present disclosure, the illustrated humidification unit 108 is a pass-over humidifier that comprises a humidification chamber 114 and an inlet 110 to the humidification chamber 114. In some implementations, the humidification chamber 114 comprises a body 116 having a base 118 attached thereto. A compartment can be defined within the humidification chamber 116 that is adapted to hold a volume of liquid that can be heated by heat conducted or provided through the base 118. In some implementations, the base 118 is adapted to contact a heater plate 120. The heater plate 120 can be controlled through a controller 122 or other suitable component such that the heat transferred into the liquid can be varied and controlled.

The controller 122 of the humidification unit 108 can control operation of various components of the respiratory humidification system 100. While the illustrated system is illustrated as using a single controller 122, multiple controllers can be used in other configurations. The multiple controllers can communicate or can provide separate functions and, therefore, the controllers need not communicate. In some implementations, the controller 122 may comprise a microprocessor, a processor, or logic circuitry with associated memory or storage that contains software code for a computer program. In such implementations, the controller 122 can control operation of the respiratory humidification system 100 in accordance with instructions, such as contained within the computer program, and also in response to internal or external inputs. The controller 122, or at least one of the multiple controllers, can be located with the breathing circuit, either attached to the breathing circuit or integrated as part of the breathing circuit.

The body 116 of the humidification chamber 114 comprises a port 124 that defines the inlet 110, and a port 126 that defines an outlet 128 of the humidification chamber 114. As liquid contained within the humidification chamber 114 is heated, liquid vapor is mixed with gases introduced into the humidification chamber 114 through the inlet port 124. The mixture of gases and vapor exits the humidification chamber 114 through the outlet port 126.

The respiratory humidification system 100 includes a breathing circuit 200 comprising the inspiratory limb 202 connected to the outlet 128 that defines the outlet port 126 of the humidification unit 108. The inspiratory limb 202 conveys toward a user the mixture of gases and water vapor that exits the humidification chamber 114. The inspiratory limb 202 can include a heating element 206 positioned along the inspiratory limb 202, wherein the heating element 206 is configured to reduce condensation along the inspiratory limb 202, to control a temperature of gas arriving at the user, to maintain humidity of the gas, or any combination of these. The heating element 206 can raise or maintain the temperature of the gases and water vapor mixture being conveyed by the inspiratory limb 202. In some implementations, the heating element 206 can be a wire that defines a resistance heater. By increasing or maintaining the temperature of the gases and water vapor mixture leaving the humidification chamber 114, the water vapor is less likely to condensate out of the mixture.

The respiratory humidification system 100 can be used in conjunction with an incubator 208. The incubator 208 can be configured to maintain a desired environment for a user within the incubator 208, such as a selected, defined, or desired temperature. Within the incubator 208, therefore, an interior ambient temperature may be different than a temperature outside the incubator 208. Thus, the incubator 208 causes, defines, creates, or maintains different temperature zones along the inspiratory limb 202, where the interior temperature is typically hotter than the exterior temperature. Having at least two different temperature zones along the inspiratory limb 202 can create problems during delivery of gas to a user such as condensation along the inspiratory limb 202, delivering a gas that has a temperature that is too high, or both.

The respiratory humidification system 100 can include an expiratory limb 210 with associated heating element 212. In some embodiments, the expiratory limb 210 and the inspiratory limb 202 can be connected using a suitable fitting (e.g., a wye-piece). In some embodiments, the respiratory humidification system 100 can be used in conjunction with a radiant warmer, under a blanket, or in other systems or situations that create two or more temperature zones. The systems and methods described herein can be used with such systems and are not limited to implementations incorporating incubators.

The inspiratory limb 202 can be divided into segments 202a and 202b where a first segment 202a can be a portion of the inspiratory limb 202 that is outside the incubator 208 and a second segment 202b (e.g., an incubator extension), can be a portion of the inspiratory limb 202 that is inside the incubator 208. The first and second segments 202a, 202b can be different lengths or the same length. In some embodiments, the second segment 202b can be shorter than the first segment 202a, and, in certain implementations, the second segment 202b can be about half as long as the first segment 202a. The first segment 202a, for example, can have a length that is at least about 0.5 m and/or less than or equal to about 2 m, at least about 03 m and/or less than or equal to about 1.8 m, at least about 0.9 m and/or less than or equal to about 1.5 m, or at least about 1 m and/or less than or equal to about 1.2 m. The second segment 202b, for example, can have a length that is at least about 0.2 m and/or less than or equal to about 1.5 m, at least about 0.3 m and/or less than or equal to about 1 m, at least about 0.4 m and/or less than or equal to about 0.8 m, or at least about 0.5 m and/or less than or equal to about 0.7 m.

The segments of the inspiratory limb 202a, 202b can be coupled to one another to form a single conduit for gas delivery. In some embodiments, the first segment 202a can include one or more first heater wires 206a and one or more first sensors 204a and can be used without the second segment 202b. The controller 122 can be configured to control the first heater wires 206a and read the first sensor 204a without the second segment 202b being coupled to the first segment 202a. Furthermore, when the second segment 202b is coupled to the first segment 202a, the controller 122 can be configured to control the first and second heater wires 206a, 206b and read the first and second sensors 204a, 204b in their respective segments. In some embodiments, the controller 122 can be configured to control the respective first and second heater wires 206a, 206b and to read the respective first and second sensors 204a, 204b when the second segment 202b is attached; and to control the first heater wires 206a and to read the first sensor 204a when the second segment 202b is not attached, without modification to the controller 122 or humidification unit 108. Thus, the same controller 122 and/or humidification unit 108 can be used whether the inspiratory limb 202 includes both the first and second segments 202a, 202b or only the first segment 202a. In some embodiments, the controller 122 can be further configured to control the heater wires 212 in the expiratory limb 210 without modification to the controller 122 or humidification unit 108. Accordingly, the respiratory humidification system 100 can function with or without the second segment 202b attached and/or with or without the expiratory limb 210 attached.

In some embodiments, the first and second segments 202a, 202b are permanently joined together to form a single conduit for gas delivery. As used here, permanently joined can mean that the segments 202a, 202b are joined together in a manner that makes it difficult to separate the segments, such as through the use of adhesives, friction fits, overmolding, mechanical connectors, and the like. In some embodiments, the first and second segments 202a, 202b are configured to be releasably coupled. For example, the first segment 202a can be used for gas delivery without the second segment 202b, or the first and second segments 202a, 202b can be coupled together to form a single conduit for gas delivery. In some embodiments, the first and second segments 202a, 202b can be configured such that they can be coupled together in only one configuration. For example, the first segment 202a can have a defined chamber-end (e.g., an end closest to the chamber 114 or humidification unit 108 along a direction of the flow of the humidified gas to the patient) and a defined patient-end (e.g., an end closest to the patient along a direction of the flow of the humidified gas to the patient) wherein the chamber-end is configured to couple to components at the chamber 114 and/or humidification unit 108. The second segment 202b can have a defined chamber-end and a defined-patient end wherein the chamber-end is configured to only couple to the patient-end of the first segment 202a. The chamber-end of the first segment 202a can be configured to not couple with either end of the second segment 202b. Similarly, the patient-end of the first segment 202a can be configured to not couple with the patient-end of the second segment 202b. Similarly, the patient-end of the second segment 202b can be configured to not couple with either end of the first segment 202a. Accordingly, the first and second segments 202a, 202b can be configured to be coupled in only one way to form a single conduit for gas delivery. In some embodiments, the first and second segments 202a, 202b can be configured to be coupled in a variety of configurations. For example, the first and second segments 202a, 202b can be configured to not include a defined patient-end and/or a defined chamber-end. As another example, the first and second segments 202a, 202b can be configured such that the patient-end and/or the chamber-end of the first segment 202a can couple to either the chamber-end or the patient-end of the second segment 202b. Similarly, the first and second segments 202a, 202b can be configured such that the chamber-end and/or the patient-end of the second segment 202a can couple to either the chamber-end or the patient-end of the second segment 202b.

The respiratory humidification system 100 can include an intermediate connector 214 that can be configured to electrically couple elements of the first and second segments 202a, 202b of the inspiratory limb 202. The intermediate connector 214 can be configured to electrically couple the heater wires 206a in the first segment 202a to the heater wires 206b in the second segment 202b to enable control of the heater wires 206a, 206b using the controller 122. The intermediate connector 214 can be configured to electrically couple the second sensor 204b in the second segment 202b to the first sensor 204a in the first segment to enable the controller 122 to acquire their respective outputs. The intermediate connector 214 can include electrical components that enable selective control of the heater wires 206a, 206b and/or selective reading of the sensors 204a, 204b. For example, the intermediate connector 214 can include electrical components that direct power through the first heater wires 206a in a first mode and through the first and second heater wires 206a, 206b in a second mode. The electrical components included on the intermediate connector 214 can include, for example and without limitation, resistors, diodes, transistors, relays, rectifiers, switches, capacitors, inductors, integrated circuits, micro-controllers, micro-processors, RFID chips, wireless communication sensors, and the like. In some embodiments, the intermediate connector 214 can be configured to be internal to the inspiratory limb 202 such that it is substantially shielded from external elements (e.g., less than 1% of the water, particulates, contaminates, etc. from an environment external to the inspiratory limb 202 contacts the intermediate connector 214). In some embodiments, some of the electrical components on the intermediate connector 214 can be configured to be physically isolated from the humidified gas within the inspiratory limb 202 to reduce or prevent damage that may result from exposure to humidity. In some embodiments, the intermediate connector 214 can include relatively inexpensive passive electrical components to reduce cost and/or increase reliability.

The inspiratory limb 202 can include sensors 204a, 204b in respective segments of the inspiratory limb 202a, 202b. The first sensor 204a can be positioned near an end of the first segment 202a, close to the incubator 208 so that the parameter derived from the first sensor 204a corresponds to a parameter of the humidified gas entering the second segment 202b. The second sensor 204b can be positioned near an end of the second segment 202b so that the parameter derived from the second sensor 204b corresponds to a parameter of the humidified gas delivered to the patient or user. The output of the sensors 204a, 204b can be sent to the controller 122 as feedback for use in controlling power delivered to the heating elements 206a, 206b of the segments of the inspiratory limb 202a, 202b. In some embodiments, one or both of the sensors 204a, 204b can be temperature sensors, humidity sensors, oxygen sensors, flow sensors, or the like. A temperature sensor can be any suitable type of temperature sensor including, for example and without limitation, a thermistor, thermocouple, digital temperature sensor, transistor, and the like. The parameters provided by or derived from the sensors can include, for example and without limitation, temperature, humidity, oxygen content, flow rate, or any combination of these or the like.

The controller 122 can be configured to control the heater wires 206a and 206b, to receive feedback from the sensors 204a and 204b, to provide logic to control power to the heater wires 206a and 206b, to adjust control of the heater wires 206a and 206b in response to readings from the sensors 204a and 204b, to detect a presence of a second segment 202b of the inspiratory limb 202, to derive parameters from the readings from the sensors 204a and 204b, and the like. In some embodiments, the controller 122 includes a power source configured to deliver electrical power to the heater wires. The power source can be a source of alternating current or direct current. In some embodiments, the controller 122 can receive input from a heater plate sensor 130. The heater plate sensor 130 can provide the controller 122 with information regarding a temperature and/or power usage of the heater plate 120. In some embodiments, the controller 122 can receive input from a flow sensor 132. Any suitable flow sensor 132 can be used and the flow sensor 132 can be positioned between ambient air and the humidification chamber 114 or between the pressurized gas source 102 and the humidification chamber 114. In the illustrated system, the flow sensor 132 is positioned on the inlet port 124 of the humidification chamber 114.

Segmented Inspiratory Limbs

Figure 2:
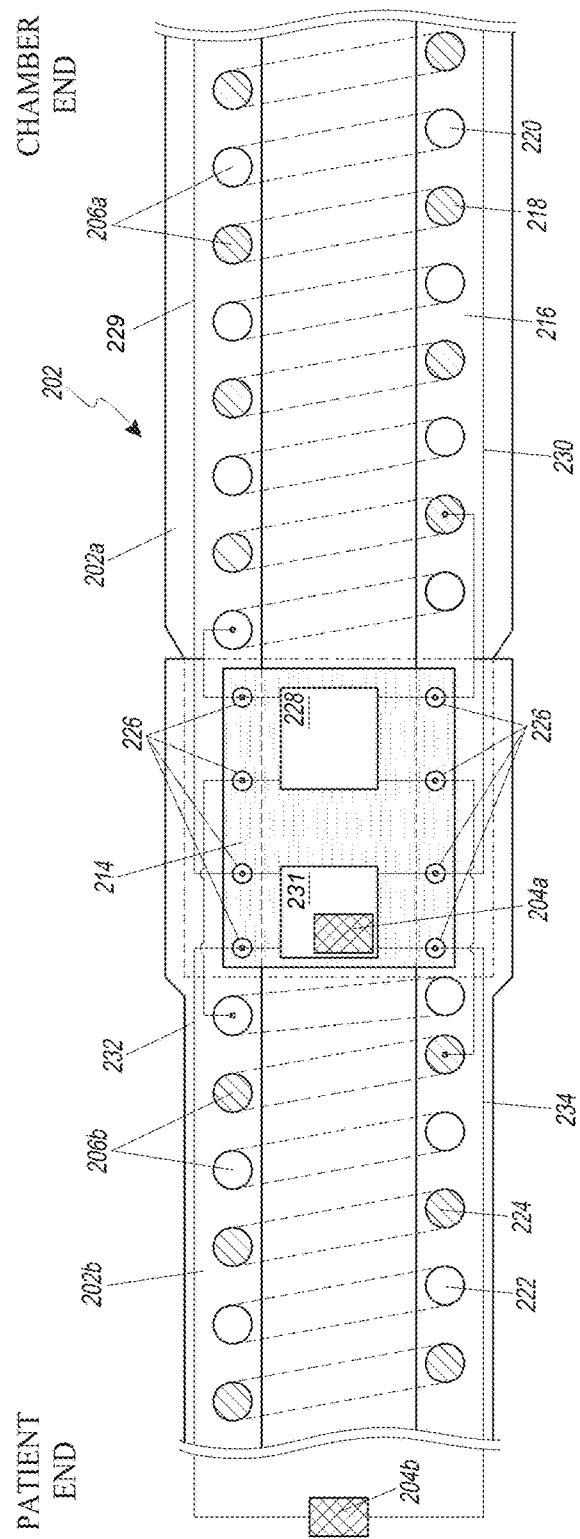
FIG. 2 illustrates a segmented inspiratory limb for use with a humidification system, the segmented inspiratory limb having an intermediate connector configured to couple heater wires and sensors in the two segments.

FIG. 2 illustrates a portion of a segmented inspiratory limb 202 for use with a respiratory humidification system 100, the segmented inspiratory limb 202 comprising a first segment 202a and a second segment 202b and having an intermediate connector 214 configured to couple first heater wires 206a to second heater wires 206b and a first sensor 204a to a second sensor 204b in the respective segments 202a and 202b. Coupling the two segments 202a and 202b can comprise mechanically coupling the segments to form a single conduit through which humidified gases can be delivered to a user wherein mechanically coupling the segments 202a and 202b can result in electrically coupling the respective heater wires 206a, 206b and the respective sensors 204a, 204b through the intermediate connector 214.

The segmented inspiratory limb 202 can comprise a structure 216 forming a lumen through which humidified gases can pass. The structure 216 can include paths formed within walls of the structure 216 configured to house heater wires 206a or 206b such that the heater wires 206a or 206b are shielded from the humidified gases travelling through the lumen and/or are covered by an external surface of the structure 216 so that they are not exposed. For example, the structure 216 can be a spiral bubble tube wherein the heater wire paths are coils molded into the tube. The structure 216 can comprise any type of suitable material and can include insulating material and/or flexible material. In some embodiments, the structure 216 and the intermediate connector 214 can be configured such that, when the first and second segments 202a and 202b are mechanically coupled, the heater wires 206a and 206b wrap over the intermediate connector 214 in such a way as to be electrically coupled to the intermediate connector 214. In some embodiments, the first segment 202a and/or the intermediate connector 214 can exclude any flying leads for connecting to the second segment 202b, thereby facilitating connection of the second segment 202b to the first segment 202a.

The structure 216 at complementary ends of the first and second segments 202a and 202b can be configured to house the intermediate connector 214. Thus, the intermediate connector 214 can be internal to the inspiratory limb 202. In some embodiments, the complementary ends of the first and second segments 202a and 202b can be configured to shield the intermediate connector 214 from humidified gases travelling through the inspiratory limb 202. In some embodiments, the intermediate connector 214 is both internal to the inspiratory limb 202 and shielded from humidified gases in the conduit, thereby reducing or eliminating exposure of electrical connections on the intermediate connector 214.

In some embodiments, the first heater wires 206a can comprise two wires 218 and 220 and the second heater wires 206b can comprise two wires 222 and 224. The two wires 218 and 220 in the first segment 202a can be electrically coupled to one another through electrical components 228 wherein the electrical coupling creates an electrical path through the wire 218, at least a portion of the electrical components 228, and the wire 220. Similarly, the two wires 222 and 224 in the second segment 202b can be electrically coupled to one another through electrical components 228 and/or electrically shorted together at an end of the segment 202b opposite the intermediate connector 202b, such as through a patient-end connector (not shown) as described in greater detail herein with reference to FIGS. 3A, 3B, 8A, 8B, 9, and 13. By coupling the wires 222 and 224 of the second segment 202b at the intermediate connector 214, electrical connections at the patient-end of the inspiratory limb 202 are reduced or eliminated which can reduce cost, system complexity, and/or risk to the patient.

The intermediate connector 214 can be configured to allow a single controller to control power to the heater wires 206a, 206b, wherein the controller can be the humidifier controller 122 as described herein with reference to FIG. 1. In some embodiments, the humidifier controller 122 controls the heater wires without any additional control functionality located on the intermediate connector 214. For example, the intermediate connector 214 can include passive components without any logic circuitry wherein the passive components direct power to heater wires 206a and/or 206b as selected by the controller 122. This can allow the intermediate connector 214 to be designed using relatively inexpensive components and can reduce the complexity of the design.

In some embodiments, heating of the two segments 202a and 202b can be accomplished using a maximum of four wires in each segment 202a, 202b. For example, in the first segment 202a the four wires can include a first heater wire 218, a second heater wire 220, a signal sensor wire 229, and a return sensor wire 230. In the second segment 202b the four wires can include a first heater wire 222, a second heater wire 224, a second signal sensor wire 232, and a second return sensor wire 234. By coupling the second heater wires 222, 224 to the first heater wires 218, 220 at connection points 226, and by coupling the second sensor signal wire 232 and the second return sensor wire 234 and to the sensor signal wire 229 and the return sensor wire 230 at connection points 226, a controller can be configured to provide power independently to the first heater wires 206a and the second heater wires 206b and to read sensor data independently from the sensors 204a and 204b without including more than four wires in either segment 202a or 202b. In some embodiments, control of the heater wires 206a and 206b and reading of the sensors 204a and 204b can be accomplished using less than four wires in each segment (e.g., using 3 wires or using 2 wires) or using more than four wires in each segment (e.g., using 5 wires, using 6 wires, using 7 wires, using 8 wires, or using more than 8 wires).

The intermediate connector 214 can include electrical components 228 configured to allow a controller 122 to selectively control heater wires 206a, 206b. The controller 122 can be configured to control heating of the inspiratory limb 202 using two modes wherein a first control mode comprises providing power to the heater wires 206a in the first segment, and a second control mode comprises providing power to the heater wires 206a and 206b in the first and second segments 202a and 202b. Thus, the controller 122 can be configured to independently control heater wire sections. This ability allows for the controller 122 to control heating of the inspiratory limb 202 when the second segment 202b is not present by solely controlling the heating of the inspiratory limb according to the first control mode, thereby allowing for the respiratory humidification system 100 to be used in a variety of circumstances without modifying the controller 122 or humidification unit 108. In some embodiments, the control modes can include a mode where power is delivered only to the heater wires 206b in the second segment 202b. In some embodiments, the controller 122 includes an electrical power source that provides electrical current. The first and second control modes can be based at least in part on the voltage supplied by the power source wherein a positive voltage or positive current can trigger the first control mode and a negative voltage or a negative current can trigger the second control mode. In some embodiments, the power source provides rectified AC or DC power to the heater wires 206a, 206b and a change in the rectification or polarity triggers a change in the control mode. By switching control modes, control of heating in the breathing circuit 200 can be accomplished with any power supply that can switch the polarity of the output signal. In some embodiments, the amount of power provided to the heater wires 206a, 206b can be adjusted by adjusting a duty cycle of power applied to the heater wires 206a, 206b. For example, pulse-width modulation (PWM) can be used to power the heater wires 206a, 206b and the duty cycle of the PWM signal can be adjusted to control the power delivered. In another example, the amount of power provided to the heater wires 206a, 206b can be adjusted by controlling the amplitude of the power signal.

The intermediate connector 214 can include electrical components 231 configured to allow a controller 122 to selectively read sensors 204a, 204b. Selective reading can be accomplished through the use of a source of electrical current wherein applying a positive current across the sensor signal and return sensor wires 229 and 230 can result in the controller 122 measuring a signal from the first sensor 204a and applying a negative current across the sensor signal and return sensor wires 229 and 230 can result in the controller 122 measuring a signal from the second sensor 204b or from both the first and second sensors 204a, 204b, as described herein with reference to FIGS. 6A, 6B, and 7. The controller 122 can use the readings from the sensors 204a, 204b to adjust power to the heater wires 206a, 206b, using, for example pulse-width modulation. The first sensor 204a can be positioned near the connection or intersection of the first and second segments 202a and 202b to provide to the controller 122 a parameter of gases entering the second segment 202b, which can correspond to entering an incubator or other such region having a different ambient temperature. The second sensor 204b can be positioned at a patient-end of the second segment 202b to provide to the controller 122 a parameter of gases delivered to the patient or a parameter of gases prior to the final piece before the patient, such as a wye-piece. The controller 122 can use these readings to adjust power to the heater wires 206a, 206b to maintain the temperature of the gas at the patient-end of the inspiratory limb 202 at a targeted or suitable temperature. The targeted or suitable temperature can vary depending at least in part on the application and environment it is being used in, and can be about 37° C., about 40° C., at least about 37° C. and/or less than or equal to about 38° C., at least about 36.5° C. and/or less than or equal to about 38.5° C., at least about 36° C. and/or less than or equal to about 39° C., at least about 35° C. and/or less than or equal to about 40° C., at least about 37° C. and/or less than or equal to about 41° C., or at least about 39.5° C. and/or less than or equal to about 40.5° C. In some embodiments, the second sensor 204b can be positioned inside the incubator but not attached to the breathing circuit. By measuring parameters inside the incubator, the temperature of the second segment 202b can be calculated, for example.

The controller 122 can independently control the amount of power delivered in the first and second control modes, as described herein. Based at least in part on feedback from the sensors 204a and/or 204b, the controller 122 can independently adjust power delivered in the first and second control modes, thereby resulting in varying heater power ratios between the first and second segments 202a and 202b.

In some embodiments, the first sensor 204a is positioned within the flow of gas within the inspiratory limb 202. In some embodiments, the intermediate connector 214 or the first segment 202a can include a mechanical component that decreases turbulence in the flow of the gas across the first temperature sensor 204a which can increase accuracy in the readings of the sensor 204a. For example, the mechanical connector can have an aerodynamic cross section, examples of which are described for patient-end connectors with reference to FIGS. 15B-15E. In some embodiments, the mechanical component (e.g., a cross-member feature within the inspiratory conduit) that decreases turbulence also secures the sensor 204a within the flow of the gases. In some embodiments, the intermediate connector 214 and the mechanical component are configured to thermally isolate the sensor 204a from the electrical components on the intermediate connector 214, which may be advantageous where the sensor 204a is a temperature sensor, for example.

In some embodiments, the intermediate connector 214 includes additional connection points in addition to the connection points 26 illustrated in FIG. 2. The additional connection points can be used to incorporate further functionality into the breathing circuit such as, for example, incorporating a memory device (PROM), a micro-controller, additional circuits, and the like.

Intermediate Connector Circuits

Figure 3A:
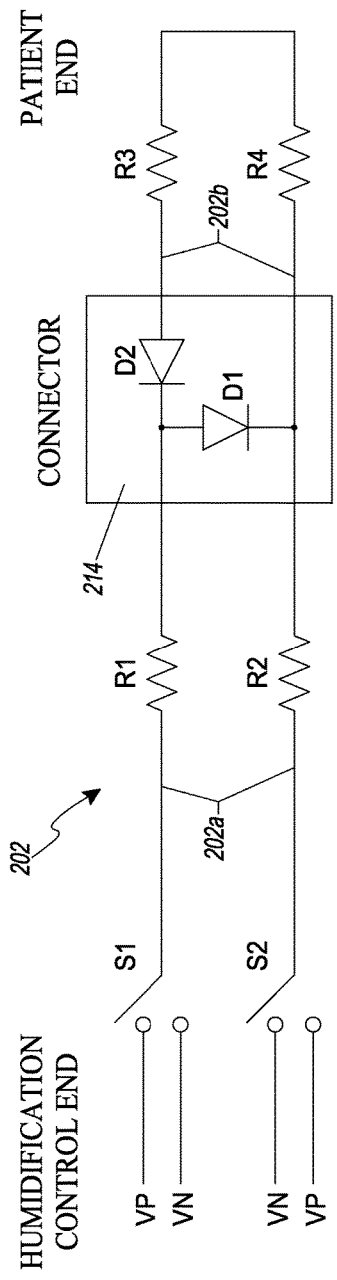
FIGS. 3A and 3B illustrate example circuit diagrams including an active rectified power source for providing power to heater wires in a segmented inspiratory limb of a breathing circuit, wherein the circuit is configured to power heater wires in a first segment of the inspiratory limb in a first mode and to power heater wires in both segments in a second mode.

FIG. 3A illustrates a circuit diagram of an example intermediate connector 214 including an active rectified power source for providing power to heater wires in a segmented inspiratory limb of a breathing circuit, wherein the circuit is configured to power heater wires R1 and R2 in a first segment of the inspiratory limb in a first mode and to power heater wires R1, R2, R3, and R4 in both segments in a second mode. By providing diodes D1 and D2 on the intermediate connector 214 and switches S1 and S2, power can be alternatively applied through heater wires R1 and R2, where the resistors represent the heater wires, or through heater wires R1, R2, R3, and R4.

The power source is represented in the figure using VP and VN which correspond to terminals of a power supply. In an embodiment, the voltage supply is an alternating current (AC) power supply. Alternatively, the power source can be a direct current (DC) power supply. Although described in this embodiment as diodes, D1 and D2 can include any of a plurality of different types of flow control devices such as, for example and without limitation, rectifiers, transistors, relays, switches, triacs, mosfets, thyristors (SCR), thermostats, and the like.

The switches S1 and S2 switch between the VP and VN terminals of the power source. In an embodiment, switches S1 and S2 are switched every half-cycle of an AC power cycle so that approximately equal current is drawn from the power source during every half cycle. The circuit illustrated in FIG. 3A can be used to control the heaters R1, R2, R3, and R4 in two control modes, wherein a first control mode corresponds to providing power only to R1 and R2, and a second control mode corresponds to providing power to R1, R2, R3 and R4. To provide power only to the heaters R1 and R2 in the first segment 202a (corresponding to the first control mode), switch S1 connects to VP and switch S2 connects to VN during a positive cycle from the power source, and switch S1 connects to VN and switch S2 connects to VP during a negative cycle from the power source. In the first control mode, current flows through R1, R2, and D1 while D2 prevents current from flowing through R3 and R4. To provide power to the heaters R1, R2, R3, and R4 in the first and second segments 202a, 202b (corresponding to the second control mode), switch S1 connects to VN and switch S2 connects to VP during a positive cycle from the power source, and switch S1 connects to VP and switch S2 connects to VN during a negative cycle from the power source. In the second control mode, current flows through R1, R2, R3, R4 and D2 while D1 prevents current from shorting across the wires to bypass heaters R3 and R4. Switching of switches S1 and S2 can be accomplished through hardware or software that adds logic to the system, as described herein with reference to FIG. 5. In some embodiments, switching of switches S1 and S2 is performed at the zero crossing of an AC power cycle. In some embodiments, the falling and rising edges of zero crossing circuitry are not delayed by the same amount and the circuit is not active near the zero crossing. Thus, the switching of switches S1 and S2 can be performed with or without zero-crossing switching detection and/or logic.

The diodes D1 and D2 can dissipate power in the circuit, and therefore generate heat. In some embodiments, Schottky diodes can be used where it is desirable to reduce power dissipation in relatively high-temperature environments. Schottky diodes can be operated near a maximum junction temperature to reduce or minimize power dissipation, which may be desirable in certain implementations of the respiratory humidification system described herein. In some embodiments, the heat generated by the diode can influence temperature readings of the sensor 204a. To reduce this influence, the diodes can be thermally connected to an airflow path of the circuit. To reduce this influence and to dissipate the heat generated by the diodes, a heat sink or pad can be included on the intermediate connector 214 that is thermally coupled to the ambient environment. To reduce this influence, and the influence of other components on the intermediate connector 214, the sensor 204a (e.g., a thermistor or other temperature sensor) can be thermally insulated from the components and physically located relatively far from the other components, as described with reference to FIGS. 14A-B, and 15.

Figure 3B:
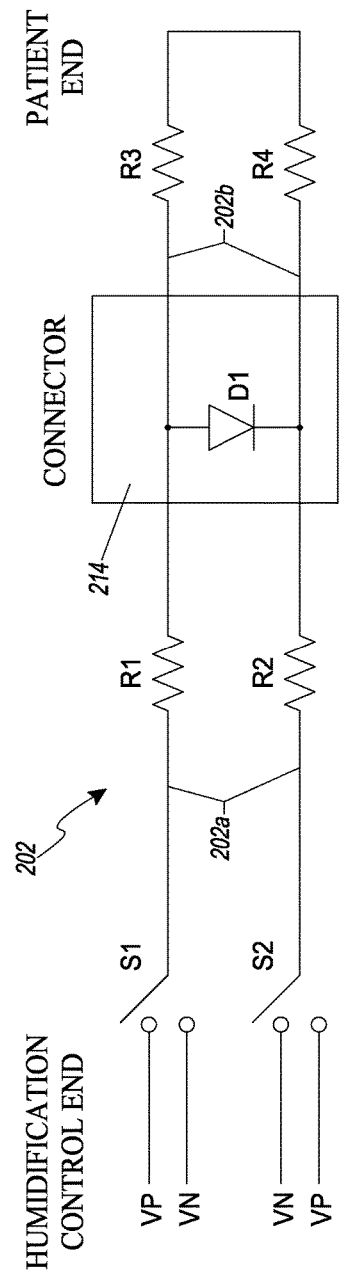

FIG. 3B illustrates another circuit diagram of an example intermediate connector 214 including an active rectified power source for providing power to heater wires in a segmented inspiratory limb of a breathing circuit, wherein the circuit is configured to power heater wires R1 and R2 in a first segment of the inspiratory limb in a first mode and to power heater wires R1, R2, R3, and R4 in both segments in a second mode. As shown in FIG. 3B, only diode D1 may be provided and the path of power through heater wires R1 and R2 or through heater wires R1 through R4 can still be controlled, as previously described with respect to FIG. 3A. The diode D2 that was shown in the circuit of FIG. 3A is eliminated. The circuit shown in FIG. 3B, having only one diode D1, can result in less heat generated by the circuit, reduced parts costs, and a smaller circuit board. The remaining portions of the circuit shown in FIG. 3B operate in a manner that is similar to the description of FIG. 3A. In embodiments without D2, as illustrated in FIG. 3B, most of the current flows through R1, R2 and D1 with only residual current flowing through R3 and R4. The residual current through R3 and R4 can be negligible such that it does not affect the performance of the humidification system.

In addition to the AC operation described with respect to FIGS. 3A and 3B, similar circuits can be operated with a DC supply. Switches S1 and S2 can be switched based at least in part on, for example, time, an output current of the supply, feedback from sensors, or other control inputs. In such an embodiment, the circuits illustrated in FIG. 3A or 3B also can be used to control the heaters R1, R2, R3, and R4 in two control modes, wherein a first control mode corresponds to providing power only to R1 and R2, and a second control mode corresponds to providing power to R1 through R4. To provide power only to the heaters R1 and R2 in the first segment 202a (corresponding to the first control mode), switch S1 connects to VP and switch S2 connects to VN. In the first control mode, current flows through R1, R2, and D1. D2 prevents current from flowing through R3 and R4 in the circuit shown in FIG. 3A. However, D2 is an optional component as shown in FIG. 3B. To provide power to the heaters R1, R2, R3, and R4 in the first and second segments 202a, 202b (corresponding to the second control mode), switch S1 connects to VN and switch S2 connects to VP. In the second control mode, current flows through R1, R2, R3, R4, while D1 prevents current from shorting across the wires to bypass heaters R3 and R4. As previously described, switching can be accomplished through hardware or software that adds logic to the system, as described herein with reference to FIG. 5.

Control of Inspiratory and Expiratory Limb Heaters

FIG. 1 also illustrates an example respiratory humidification system 100 having an inspiratory limb 202 and an expiratory limb 210, wherein the humidification system 100 is configured to control heater wires 206, 212 in both limbs. In some embodiments, heater wires 212 in the expiratory limb 210 can be electrically coupled to the inspiratory heater wires 206 outside the humidification unit 108 and controller 122 so that control of the expiratory heater wires 212 can be implemented without affecting other control modes and without additional switching transistors. Similarly, the expiratory heater wires 212 can be electrically coupled to the inspiratory heater wires 206 within the humidification unit 108. Connection of the expiratory heater wires 212 to the inspiratory heater wires 206 can be done in the humidification system 108, on the intermediate connector 214, in a sensor cartridge at the humidification system 108, or the like. Thus, the controller 122 can control the expiratory heater wires 212 with no additional electrical connections at the patient end, the presence of which may increase risk, system complexity, and cost. Examples of electrical coupling of the expiratory heater wires 212 and the inspiratory heater wires 206 inside the humidification unit 108 are shown in FIGS. 4A-4D, 8A, and 8B.

Figure 4A:
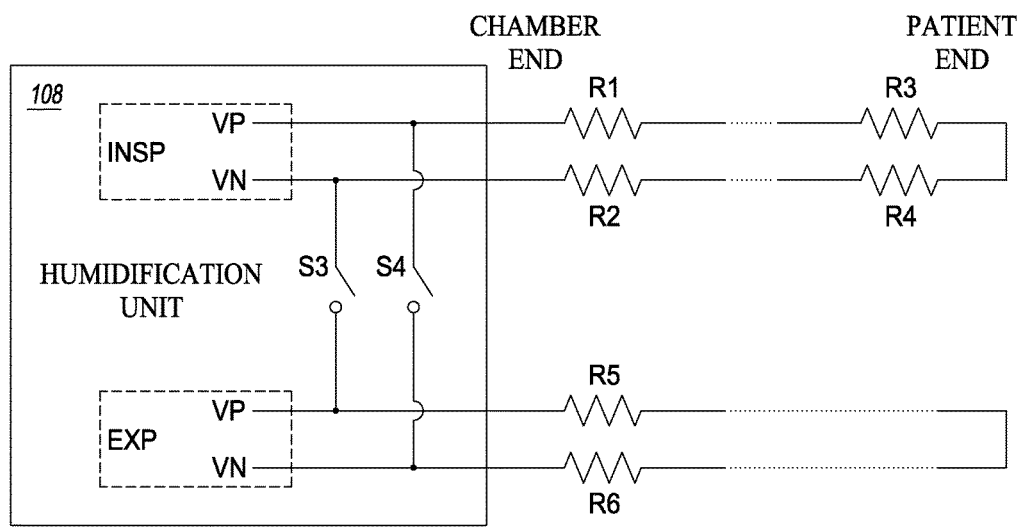
FIGS. 4A-4D illustrate example humidification systems having an inspiratory limb and an expiratory limb, wherein the humidification systems are configured to control heater wires in both limbs.

With reference to FIG. 4A, the humidification unit 108 can incorporate switches or relays S3 and S4 to select between independent and dependent control of the inspiratory heater wires and the expiratory heater wires. In some embodiments, the switches or relays are activated when a tube (e.g., an inspiratory limb or an expiratory limb) with an appropriate identification is connected to the humidification unit 108, such as through an identification resistor detected and/or measured by the humidification unit 108. For example, when the switches are not activated (e.g., both switches S3, S4 are open), the heater wires in the inspiratory limb and/or the heater wires in the expiratory limb can be individually and/or independently controlled.

When an appropriate tube is connected or the system otherwise determines it is appropriate, the switches S3 and S4 can be closed to simultaneously control the inspiratory limb and the expiratory limb. The humidification unit 108 can include an inspiratory power source INSP and an expiratory power source EXP, wherein the system can implement switching in each power source as described herein with reference to FIGS. 3A and 3B. For example, with reference to FIG. 3A, the inspiratory power source can have switches S1 and S2 configured to selectively direct positive and negative cycles to the heaters R1 through R4. Similarly, with reference to FIG. 4A, the expiratory power source EXP can include switches configured to selectively direct power to the expiratory limb having heaters R5 and R6. In some embodiments, when switches S3 and S4 are closed, both switches in expiratory power source EXP can be opened such that power is provided to the inspiratory heater wires and the expiratory heater wires by the inspiratory power source INSP. In some embodiments, the humidification unit 108 does not include an expiratory power source EXP. In such embodiments, the inspiratory power source INSP is used to provide power to the inspiratory heater wires when the switches S3 and S4 are open and to provide power to both the inspiratory and expiratory heater wires when the switches S3 and S4 are closed. Thus, the inspiratory limb heater wires 206 can be controlled in the same way as before, but now the system can use the switches S3, S4 to simultaneously control power to the expiratory heater wires 212 and the inspiratory heater wires 206 using a unified electrical circuit and/or control system. By way of example, the humidification unit 108 can operate in two modes relative to the inspiratory limb 202 (e.g., the first mode being where the humidification unit 108 provides power to the heaters R1 and R2 and the second mode being where it provides power to the heaters R1 to R4) while selectively controlling power to the heaters R5 and R6 in the expiratory limb such that the humidification unit 108 can provide no power to the heaters R5 and R6, or provide power to the heaters R5 and R6 while operating in the first mode, in the second mode, or in both modes. As previously described, a connection between the inspiratory limb 202 and expiratory limb 210 can be made internal or external to the humidification unit 108. In an embodiment, the connection is made in a sensor cartridge, the intermediate connector 214, or in another location.

In some embodiments, an expiratory circuit configured to connect the expiratory heater wires 212 to the controller 122 can be implemented at the intermediate connector 214 shown on FIG. 1. The expiratory circuit can be connected in one or more of several ways. For example, the expiratory circuit can be connected in parallel with the heater wires 206a in the first segment 202a or with the heater wires 206b in the second segment 202b. In some embodiments, the intermediate connector 214 can include an internal fly lead making the expiratory circuit available on the intermediate connector 214. In some embodiments, the intermediate connector 214 can be connected to an added third channel to so that there are no fly leads between the inspiratory and expiratory circuits. A heater wire driver control circuit can be added to the controller 122 to accommodate such embodiments.

Figure 4B:
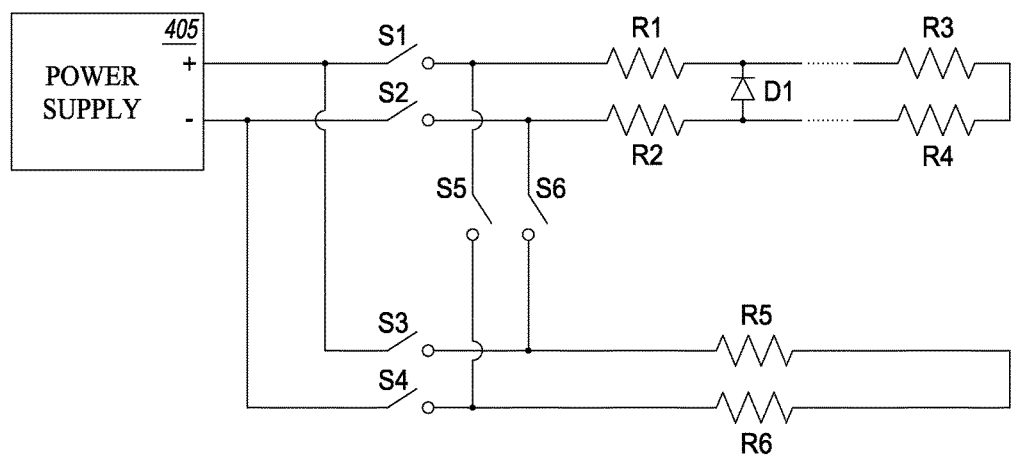

FIG. 4B illustrates an example embodiment of a humidification system incorporating a power supply 405 to provide power to both the inspiratory heater wires R1 to R4 and the expiratory heater wires R5 and R6 through a combination of switches or relays S1 to S6 and diode D1. In the illustrated embodiment, the humidification system is configured to provide power to the expiratory heater wires when only the inspiratory heater wires R1, R2 in the first segment of the inspiratory limb are receiving power (e.g., in a first operation mode) or when the inspiratory heater wires R1 to R4 in both segments are receiving power (e.g., in a second operation mode). The power supply 405 can be any suitable power supply including, for example, a power supply which provides alternating current in a sine wave, sawtooth, square wave, or other form. In some embodiments, the power supply 405 is a transformer which provides an alternating current signal with a voltage of at least about 22 VAC, at least about 5 VAC or less than or equal to about 30 VAC, at least about 10 VAC or less than or equal to about 25 VAC, at least about 12 VAC or less than or equal to about 22 VAC.

With continued reference to FIG. 4B, the humidification system can be configured to provide power to the expiratory heater wires R5, R6 in the first operation mode while the power supply 405 is providing power in a negative cycle. To do so, switches S1, S2, S5, S6 close and switches S3, S4 open. The current flows from the negative terminal of the power supply 405 through switch S2 and branches to provide power to the heater wires in both the inspiratory limb and the expiratory limb. In the inspiratory limb, the current flows to inspiratory heater wire R2, then through diode D1 to inspiratory heater wire R1, and then returns to the positive terminal on the power supply 405 through switch S1. In the expiratory limb, the current flows through switch S6 to expiratory heater wire R5, then to expiratory heater wire R6, and then returns to the positive terminal on the power supply 405 through switches S5 and S1.

Similarly, with continued reference to FIG. 4B, the humidification system can be configured to provide power to the expiratory heater wires R5, R6 in the first operation mode while the power supply 405 is providing power in a positive cycle. To do so, switches S3, S4, S5, S6 close and switches S1, S2 open. The current flows from the positive terminal of the power supply 405 through switch S3 and branches to provide power to the heater wires in both the inspiratory limb and the expiratory limb. In the inspiratory limb, the current flows through switch S6 to inspiratory heater wire R2, then through diode D1 to inspiratory heater wire R1, and then returns to the negative terminal on the power supply 405 through switches S5 and S4. In the expiratory limb, the current flows to expiratory heater wire R5, then to expiratory heater wire R6, and then returns to the negative terminal on the power supply 405 through switch S4.

With continued reference to FIG. 4B, the humidification system can be configured to provide power to the expiratory heater wires R5, R6 in the second operation mode while the power supply 405 is providing power in a positive cycle. To do so, switches S1, S2, S5, S6 close and switches S3, S4 open. The current flows from the positive terminal of the power supply 405 through switch S1 and branches to provide power to the heater wires in both the inspiratory limb and the expiratory limb. In the inspiratory limb, the current flows to inspiratory heater wire R1, then bypasses diode D1 to flow to inspiratory heater wire R3, then to inspiratory heater wire R4, then to inspiratory heater wire R2, and then returns to the negative terminal on the power supply 405 through switch S2. In the expiratory limb, the current flows through switch S5 to expiratory heater wire R6, then to expiratory heater wire R5, and then returns to the negative terminal on the power supply 405 through switches S6 and S2.

Similarly, with continued reference to FIG. 4B, the humidification system can be configured to provide power to the expiratory heater wires R5, R6 in the second operation mode while the power supply 405 is providing power in a negative cycle. To do so, switches S3, S4, S5, S6 close and switches S1, S2 open. The current flows from the negative terminal of the power supply 405 through switch S4 and branches to provide power to the heater wires in both the inspiratory limb and the expiratory limb. In the inspiratory limb, the current flows through switch S5 to inspiratory heater wire R1, then bypasses diode D1 to flow to inspiratory heater wire R3, then to inspiratory heater wire R4, then to inspiratory heater wire R2, and then returns to the positive terminal on the power supply 405 through switches S6 and S3. In the expiratory limb, the current flows to expiratory heater wire R6, then to expiratory heater wire R5, and then returns to the positive terminal on the power supply 405 through switch S3.

Figure 4C:
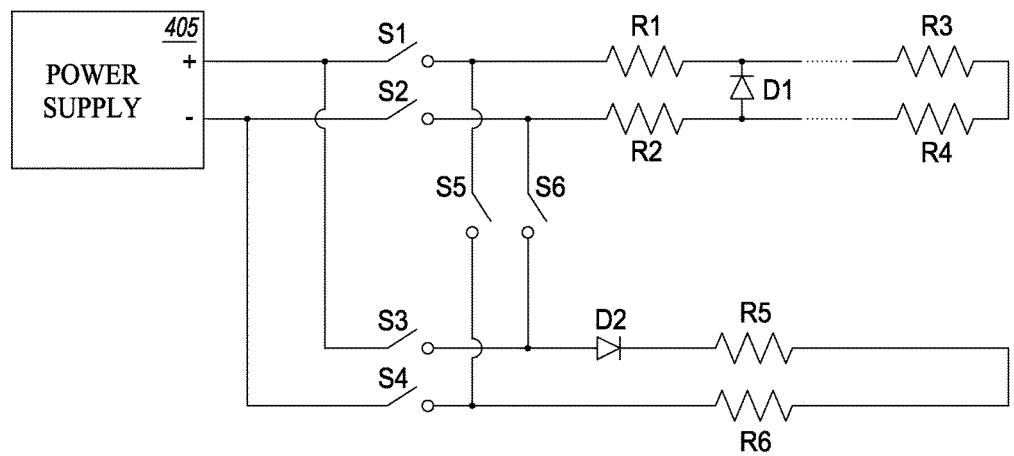

FIG. 4C illustrates an example embodiment of a humidification system incorporating a power supply 405 to provide power to both the inspiratory heater wires R1 to R4 and the expiratory heater wires R5 and R6 through a combination of switches or relays S1 to S6 and diodes D1, D2. In the illustrated embodiment, the humidification system is configured to provide power to the expiratory heater wires only when the inspiratory heater wires R1, R2 in the first segment of the inspiratory limb are receiving power (e.g., only in the first operation mode).

With continued reference to FIG. 4C, the humidification system can be configured to provide power to the expiratory heater wires R5, R6 in the first operation mode while the power supply 405 is providing power in a negative cycle. To do so, switches S1, S2, S5, S6 close and switches S3, S4 open. The current flows from the negative terminal of the power supply 405 through switch S2 and branches to provide power to the heater wires in both the inspiratory limb and the expiratory limb. In the inspiratory limb, the current flows to inspiratory heater wire R2, then through diode D1 to inspiratory heater wire R1, and then returns to the positive terminal on the power supply 405 through switch S1. In the expiratory limb, the current flows through switch S6 and through diode D2 to expiratory heater wire R5, then to expiratory heater wire R6 and then returns to the positive terminal on the power supply 405 through switches S5 and S1.

Similarly, with continued reference to FIG. 4C, the humidification system can be configured to provide power to the expiratory heater wires R5, R6 in the first operation mode while the power supply 405 is providing power in a positive cycle. To do so, switches S3, S4, S5, S6 close and switches S1, S2 open. The current flows from the positive terminal of the power supply 405 through switch S3 and branches to provide power to the heater wires in both the inspiratory limb and the expiratory limb. In the inspiratory limb, the current flows through switch S6 to inspiratory heater wire R2, then through diode D1 to inspiratory heater wire R1, and then returns to the negative terminal on the power supply 405 through switches S5 and S4. In the expiratory limb, the current flows through diode D2 to expiratory heater wire R5, then to expiratory heater wire R6, and then returns to the negative terminal on the power supply 405 through switch S4.

With continued reference to FIG. 4C, the humidification system can be configured to provide power only to the inspiratory heater wires R1 to R4 (and not to provide power to the expiratory heater wires R5, R6) in the second operation mode while the power supply 405 is providing power in a positive cycle. To do so, switches S1, S2, S5, S6 close and switches S3, S4 open. The current flows from the positive terminal of the power supply 405 through switch S1 to inspiratory heater wire R1, the current then bypasses diode D1 and flows to inspiratory heater wire R3, to inspiratory heater wire R4, to inspiratory heater wire R2 and back to the negative terminal on the power supply 405 through switch S2. The current does not flow through the expiratory heater wires because of diode D2 which blocks the flow of current through that circuit on a positive cycle with the switches configured as described.

Similarly, with continued reference to FIG. 4C, the humidification system can be configured to provide power only to the inspiratory heater wires R1 to R4 (and not to provide power to the expiratory heater wires R5, R6) in the second operation mode while the power supply 405 is providing power in a negative cycle. To do so, switches S3, S4, S5, S6 close and switches S1, S2 open. The current flows from the positive terminal of the power supply 405 through switches S4 and S5 to inspiratory heater wire R1, the current then bypasses diode D1 and flows to inspiratory heater wire R3, to inspiratory heater wire R4, to inspiratory heater wire R2 and back to the negative terminal on the power supply 405 through switches S6 and S3. The current does not flow through the expiratory heater wires because of diode D2 which blocks the flow of current through that circuit on a negative cycle with the switches configured as described.

Figure 4D:
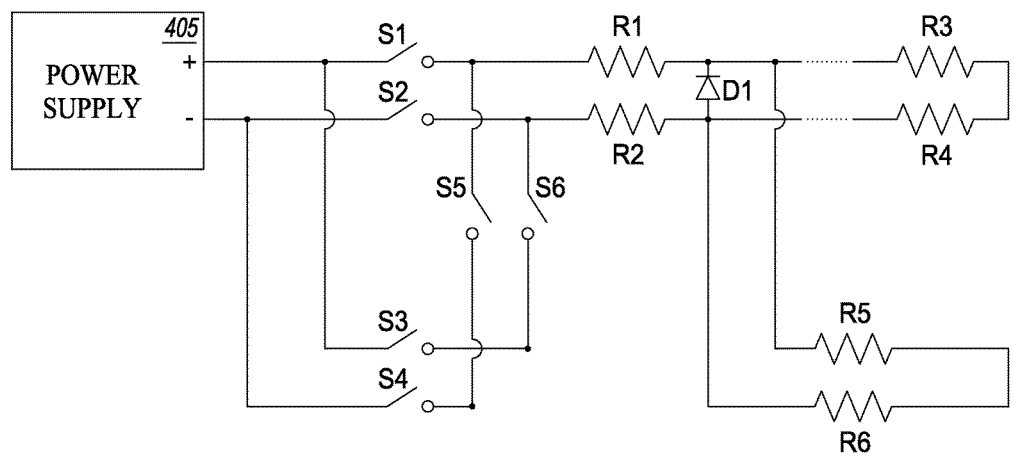

FIG. 4D illustrates an example embodiment of a humidification system incorporating a power supply 405 to provide power to both the inspiratory heater wires R1 to R4 and the expiratory heater wires R5 and R6 through a combination of switches or relays S1 to S6 and diode D1 with the expiratory heater wires R5, R6 being electrically coupled to the inspiratory heater wires R1 to R4 on a patient-side of the heater wires in the first segment of the inspiratory limb, which can occur an intermediate connector, such as any of the intermediate connectors described herein. As described with reference to FIG. 4D, the expiratory heater wires R5, R6 are coupled to the inspiratory heater wires R1 to R4 at the intermediate connector, but any suitable location after the inspiratory heater wires in the first segment can be used for coupling the heater wires in the inspiratory and expiratory limb. In the illustrated embodiment, the humidification system is configured to provide power to the expiratory heater wires only when the inspiratory heater wires R1 to R4 in both segments of the inspiratory limb are receiving power (e.g., only in the second operation mode).

With continued reference to FIG. 4D, the humidification system can be configured to provide power to the inspiratory heater wires R1 to R4 and to the expiratory heater wires R5, R6 in the second operation mode while the power supply 405 is providing power in a positive cycle. To do so, switches S1, S2, S5, S6 close and switches S3, S4 open. The current flows from the positive terminal of the power supply 405 through switch S1 to inspiratory heater wire R1, then bypasses diode D1 and branches to provide power to the heater wires in both the second segment of the inspiratory limb and the expiratory limb. In the second segment of the inspiratory limb, the current flows to inspiratory heater wire R3, then to inspiratory heater wire R4, returning to the intermediate connector. In the expiratory limb, current flows to R5 and then to R6, returning back to the intermediate connector. The current then flows through inspiratory heater wire R2 and then returns to the negative terminal on the power supply 405 through switch S2.

Similarly, with continued reference to FIG. 4D, the humidification system can be configured to provide power to the expiratory heater wires R5, R6 in the second operation mode while the power supply 405 is providing power in a negative cycle. To do so, switches S3, S4, S5, S6 close and switches S1, S2 open. The current flows from the negative terminal of the power supply 405 through switches S4 and S5 to inspiratory heater wire R1, then bypasses diode D1 and branches to provide power to the heater wires in both the second segment of the inspiratory limb and the expiratory limb. In the second segment of the inspiratory limb, the current flows to inspiratory heater wire R3, then to inspiratory heater wire R4, returning to the intermediate connector. In the expiratory limb, current flows to R5 and then to R6, returning back to the intermediate connector. The current then flows through inspiratory heater wire R2 and then returns to the positive terminal on the power supply 405 through switches S6 and S3.

With continued reference to FIG. 4D, the humidification system can be configured to provide power only to the inspiratory heater wires R1 and R2 in the first segment of the inspiratory limb (and not to provide power to the expiratory heater wires R5, R6) in the first operation mode while the power supply 405 is providing power in a negative cycle. To do so, switches S1, S2, S5, S6 close and switches S3, S4 open. The current flows from the negative terminal of the power supply 405 through switch S2 to inspiratory heater wire R2, the current then flows through diode D1 to inspiratory heater wire R1, and then returns to the positive terminal on the power supply 405 through switch S1.

Similarly, with continued reference to FIG. 4D, the humidification system can be configured to provide power only to the inspiratory heater wires R1 and R2 in the first segment of the inspiratory limb (and not to provide power to the expiratory heater wires R5, R6) in the first operation mode while the power supply 405 is providing power in a positive cycle. To do so, switches S3, S4, S5, S6 close and switches S1, S2 open. The current flows from the positive terminal of the power supply 405 through switches S3 and S6 to inspiratory heater wire R2, the current then flows through diode D1 to inspiratory heater wire R1, and returns back to the negative terminal on the power supply 405 through switches S5 and S4.

Detecting a Connected Extension of an Inspiratory Limb

Figure 5:
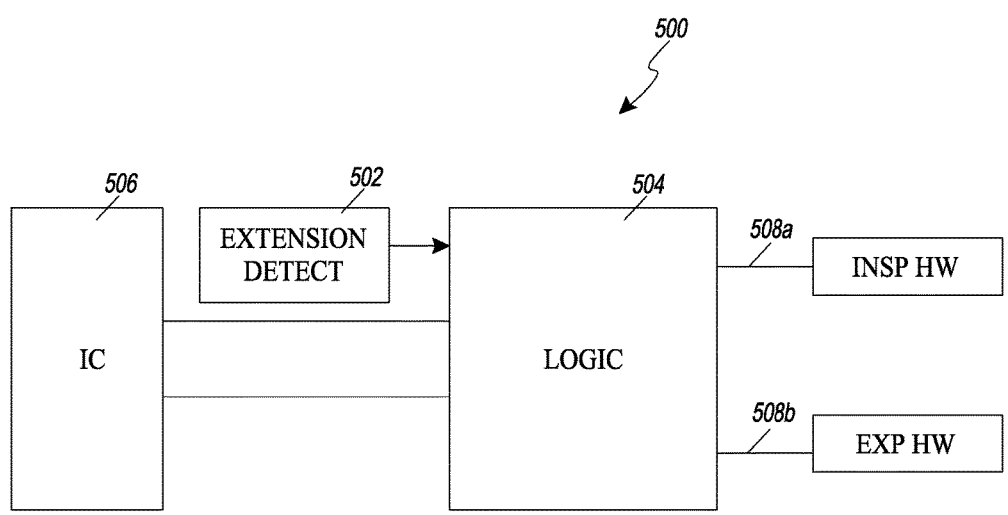
FIG. 5 illustrates a block diagram of an example system configured to detect a presence of an extension of an inspiratory limb and to provide power to heater wires in the inspiratory limb, the extension of the inspiratory limb, and an expiratory limb.

FIG. 5 illustrates a block diagram of an example system 500 configured to detect a presence of an extension of an inspiratory limb using extension detect module 502 and to provide power to heater wires in the inspiratory limb (e.g., a first segment of the inspiratory limb), the extension of the inspiratory limb (e.g., a second segment of the inspiratory limb), and/or an expiratory limb. The logic module 504, which can comprise hardware, software, or some combination of both, can be configured to provide the logic that enables the switching described for the different control modes, as described with reference to, for example, FIGS. 3A, 3B, 4, 8A, and 8B. The logic module 504 can receive signals from an integrated circuit 506 that is part of the respiratory humidification system 100. In some embodiments, the logic module 504 is software embedded wholly or partially within the integrated circuit 506 which converts signals from the integrated circuit 506. The combination of the logic module 504 and the integrated circuit 506 can be configured to detect a zero-level crossing, or where voltage or current transitions from positive to negative or vice versa, and to change states of switches according to a control mode. The logic module 504 can output PWM signals 508a, 508b according to a desired, selected, or defined power output where the PWM signal is delivered to the inspiratory heater wires (INSP HW), the expiratory heater wires (EXP HW), or both.

In some embodiments, the system 500 can include an extension detect module 502 configured to detect whether the second segment 202b is connected to the breathing circuit 200. The extension detect module 502 can produce an "enable signal" if the second segment 202b is connected. The logic module 504 can receive the "enable signal" and adjust switching accordingly. In some embodiments, the "enable signal" indicates to the logic module 504 that the system 500 will not control the inspiratory and expiratory circuits independently and simultaneously.

In some embodiments, the extension detect module 502 can be configured to detect the presence of the second segment 202b by switching on both the inspiratory and expiratory circuits and detecting whether a hardware overcurrent event is detected. If the overcurrent event is not detected when either are switched on individually but it is detected with they are both switched on together, the extension detect module 502 can produce an "enable signal" indicating that the second segment 202b is connected. In some embodiments, the extension detect module 502 can detect the presence of the second segment 202b by detecting a resistance of an identification resistor or of heater wires in each section using current measurements. Based at least in part on the current measurements of the various sections, the extension detect module 502 can produce an "enable signal" if current measurements for different cycles differ where different control modes are being implemented as described above with reference to FIGS. 3A, 3B, 4, 8A, and 8B.

Sensor Circuits

Figure 6A:
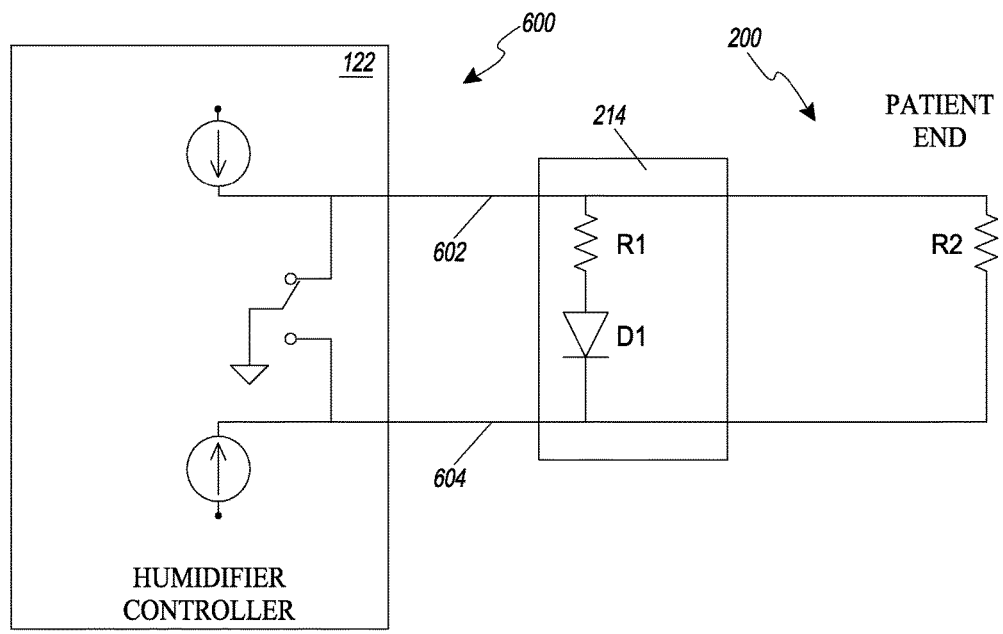
FIGS. 6A and 6B illustrate example circuit diagrams in a humidification system, wherein the circuits are configured to read data from two sensors.
Figure 6B:
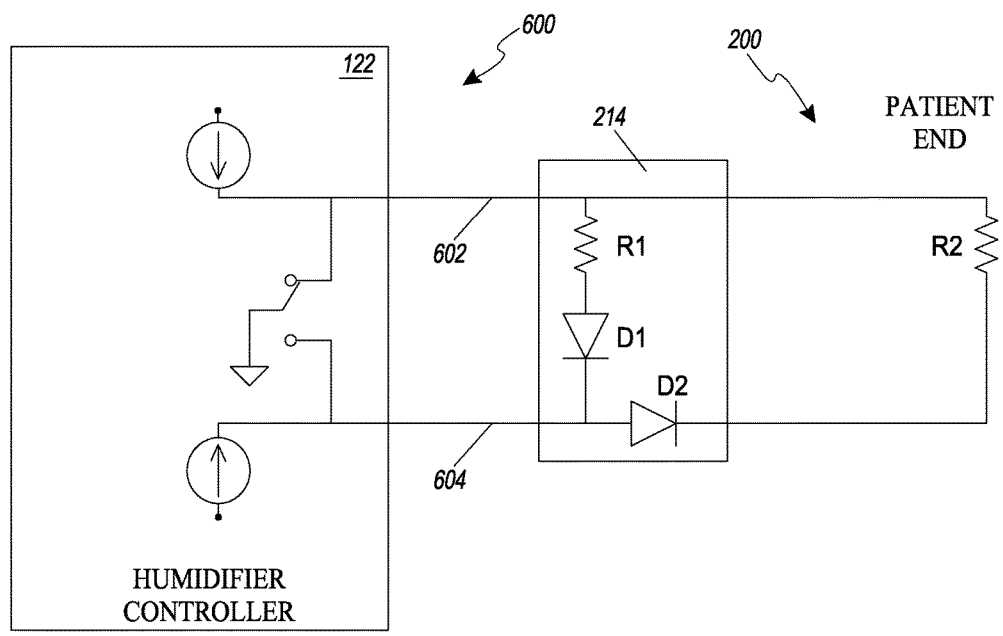

FIGS. 6A and 6B illustrate example circuit diagrams in a respiratory humidification system 100, wherein the circuit 600 is configured to read data from two sensors R1 and R2. With reference to FIGS. 6A and 6B, the sensors R1 and R2 are represented using resistors, but any suitable type of sensor can be used such as, for example and without limitation, temperature sensors, humidity sensors, flow sensors, oxygen sensors, and the like. In some embodiments, the sensors can be temperature sensors such as thermistors. In such embodiments, the sensors R1 and R2 respectively represent a first thermistor at the intermediate connector 214 and a second thermistor at a patient-end of the breathing circuit 200 (e.g., on a patient-end connector). The two thermistors R1 and R2 can be measured using two wires in the breathing circuit 200 using the circuit 600 in conjunction with a current or voltage source and switches in the humidifier controller 122. While the description with reference to FIGS. 6A and 6B involves thermistors, it is applicable to other suitable sensors which affect voltages and/or currents provided to circuits with which they are associated.

To selectively read the sensors R1 and R2, current is supplied in either polarity through lines 602 and 604. To measure the patient-end sensor R2, the humidifier controller 122 sets the switch to connect the top current supply to ground. Current then flows from the bottom current supply through R2 and to ground through the switch. Current is blocked from going through R1 by diode D1. The humidifier controller 122 can be configured to measure the voltage drop from the bottom current supply to ground, and to derive the resistance of sensor R2 based at least in part on the supplied current and measured voltage. To measure the sensor R1 positioned at the intermediate connector 214, the humidifier controller 122 can read the patient-end sensor R2 and record the result. The humidifier controller 122 can then set the switch to connect the bottom current supply to ground. Current then flows from the top current supply through R1 and R2 to ground through the switch. The humidifier controller 122 can be configured to measure the voltage drop from the top current supply to ground, and to derive the resistance of sensor R1 based at least in part on the supplied current, the measured voltage, and the recorded result from measuring the resistance of R2. In some embodiments, a voltage drop across D1 is accounted for in the derivation of the resistance of R1. In the embodiment illustrated in FIG. 6A, by placing D1 near R1, the temperature of the diode D1 can be calculated which can be used in the calculation of the voltage drop across D1. One potential advantage of the configuration illustrated in FIG. 6A is that the measurements of the sensor R2 at the patient end may be more accurate because the measurements are made without passing through a diode, as illustrated in the embodiment of FIG. 6B, which can introduce uncertainties or errors.

In some embodiments, as illustrated in FIG. 6B, an additional diode D2 can be added to the intermediate connector 214. In such embodiments, the humidifier controller 122 can be configured to measure sensors R1 and R2 in a fashion similar to the embodiment illustrated in FIG. 6A and described above. A difference is that when measuring sensor R1, current flows through R1 and D1 and not through R2 because the diode D2 blocks current flow through R2. In this way, the measurement of sensor R1 can be substantially isolated or separated from the measurement of sensor R2. Similar to the derivation of the resistance of sensor R1, the voltage drop across the diode D2 can be accounted for in deriving the resistance of sensor R2. By placing D1 and D2 near R1, the temperature of the diodes can be calculated which can be used in the calculation of the voltage drops across D1 and D2, respectively.

In certain embodiments, the measurement of sensors R1, R2 is performed in software running in a controller connected to the circuits of FIG. 6A or 6B. The direction and amount of current supplied to the circuit can be controlled by such software. An accurate measurement of the resistance of sensors R1, R2 can be obtained by measuring the voltages using, for example, an analog to digital converter. To minimize or eliminate the effects of variances caused by the diodes D1 and/or D2, the software can supply two different currents (I1 and I2) in the same direction. This will result in two different voltage readings (V1 and V2) corresponding to the two different currents (I1 and I2). Using these two voltages and currents, the software can solve for the voltage drop of the diodes D1, D2 and resistances for sensors R1, R2. For sensor R1, for example, the voltage drop can be solved with the following equation: $Vdrop=((V1*I2-V2*I1)/((V1-V2)/R2+I2-I1))$. The resistance of sensor R1 can be calculated using the following equation: $R1=(V2-Vdrop)/(I2-V2/R2)$. In an embodiment, the calculated Vdrop has a constant error from a measured Vdrop that is corrected in software. In an embodiment, the Vdrop is increased by approximately 15% as an error compensation.

Figure 7:
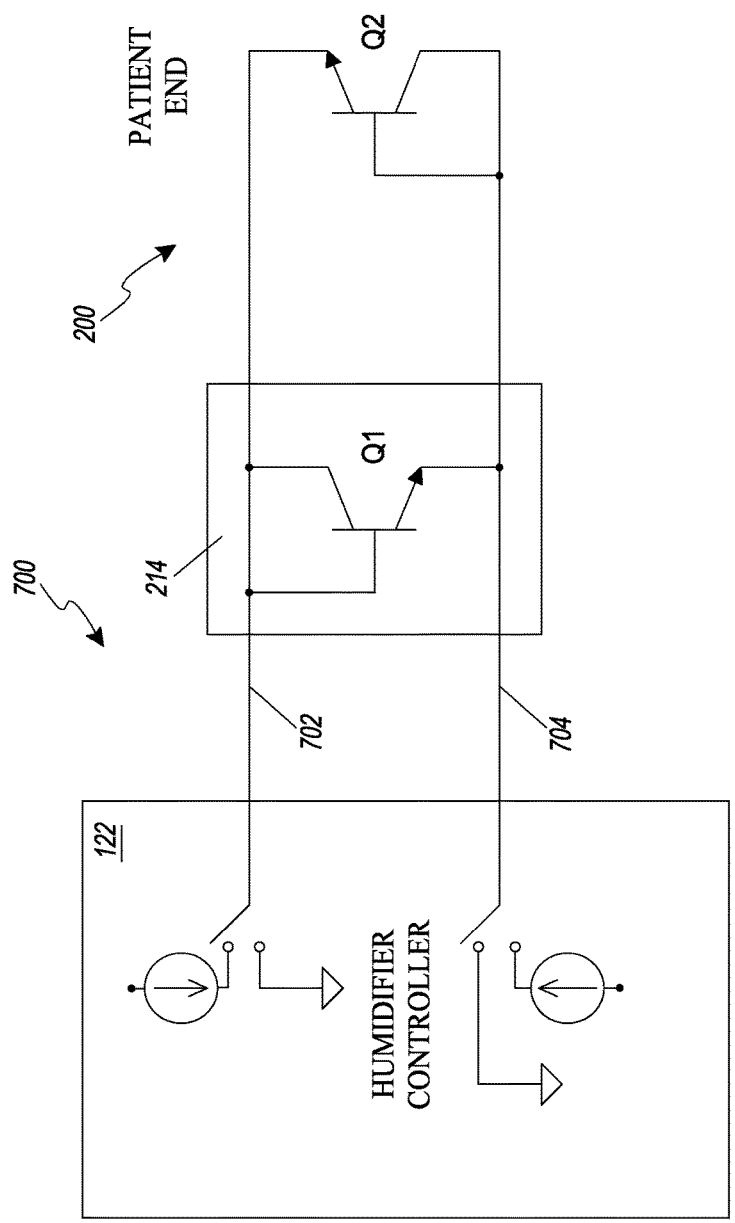
FIG. 7 illustrates an example circuit diagram in a humidification system, wherein the circuit is configured to read temperature data using two transistors.

FIG. 7 illustrates an example circuit diagram in the respiratory humidification system 100, wherein the circuit 700 is configured to read temperature data using two transistors Q1 and Q2 acting as temperature sensors. The temperature measurement can be based at least in part on a temperature effect of the pn-junction of the base and emitter terminals of the transistors. The switching of the current in the humidifier controller 122 can be the same as for the circuit described with reference to FIGS. 6A and 6B or it can be an alternate configuration, as shown. For example, the illustrated switching configuration uses two switches with two power sources and two grounds to selectively provide electrical power to the wires. In a first configuration, the top switch electrically connects a top power source to wire 702 and the bottom switch electrically connects the ground to wire 704. In a second configuration, the top switch electrically connects the ground to wire 702 and the bottom switch electrically connects the bottom power source to wire 704. By using transistors Q1 and Q2 as temperature sensors, the diodes can be removed as the transistors provide the functionality of the temperature sensors and the diodes.

Breathing Circuit Hardware Configurations

Figure 8A:
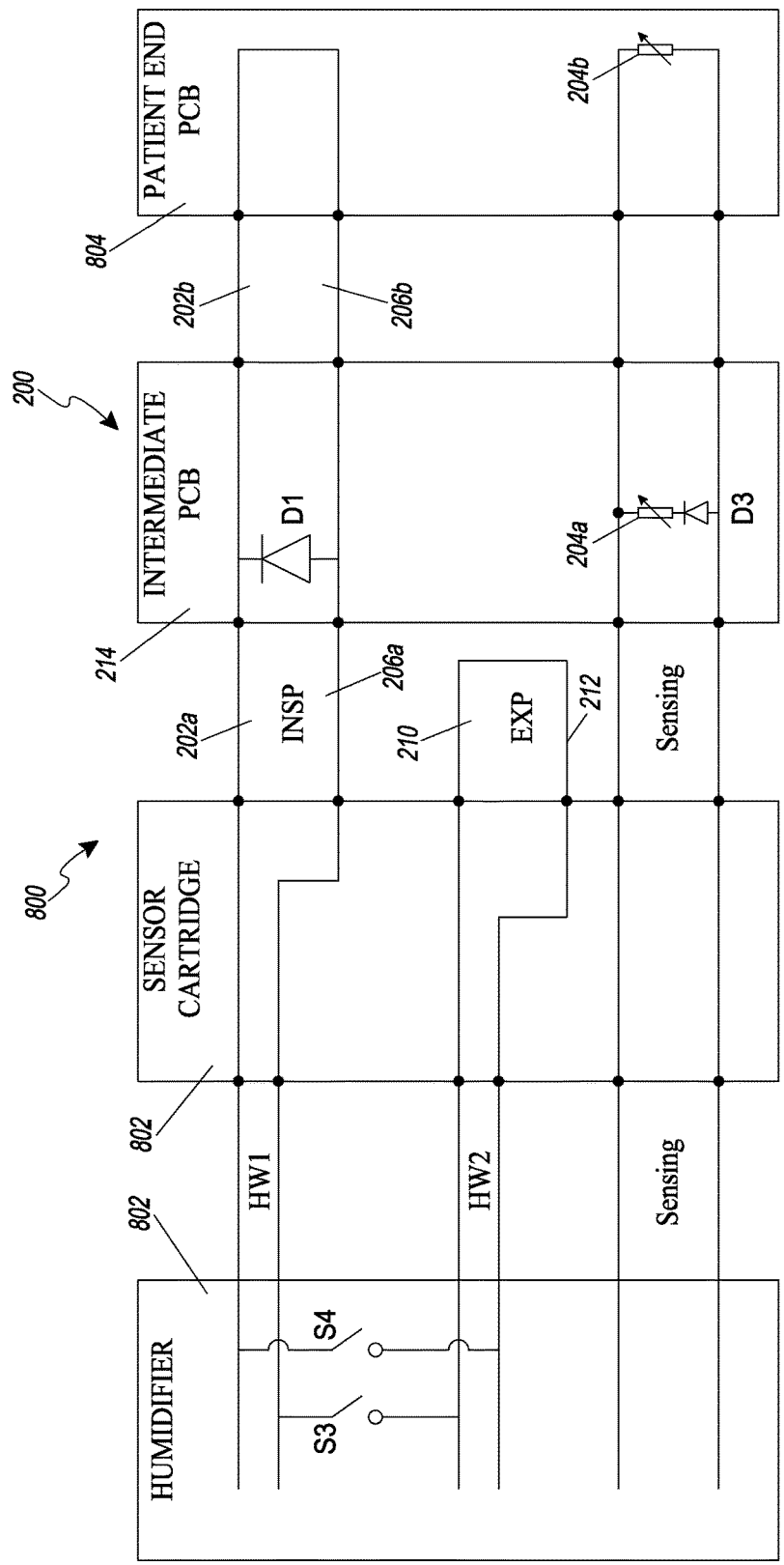
FIGS. 8A and 8B illustrate example diagrams of hardware configurations for a breathing circuit with an inspiratory limb and an expiratory limb, the inspiratory limb having a first and a second segment.

FIG. 8A illustrates an example diagram of a hardware configuration 800 for a breathing circuit 200 having a first segment of an inspiratory limb 202a, a second segment of the inspiratory limb 202b, and an expiratory limb 210. The hardware configuration 800 can include a humidifier 108 configured to couple the wiring of the heater wires HW1 and HW2 through switches or relays S3 and S4, and the wiring for sensors 204a, 204b. In some embodiments, the sensor cartridge 802 can be configured to couple the wiring of the heater wires HW1, HW2 and the wiring for sensors 204a, 204b. The switches S3, S4 can be used to selectively control power to the heater wires HW2 of the expiratory limb 210, as described with reference to FIG. 4A with similar functionality described with reference to FIGS. 4B-4D. In some embodiments, the switches S3 and S4 both default to an open position, and are closed when an appropriate tube is connected to the humidifier 108 (e.g., an inspiratory limb or expiratory limb with an appropriate identification resistor). In this way, the hardware configuration 800 can be used to provide power to heater wires HW1 and/or to heater wires HW2. Independent of whether the heater wires HW2 are receiving electrical power, the heater wires HW1 can be controlled in two modes. In a first mode, the first heater wires 206a receive electrical power while the second heater wires 206b do not. In a second mode, the first and second heater wires 206a, 206b receive electrical power. In the illustrated embodiment, heater wires HW2 are able to be powered when the heater wires HW1 are being controlled in either of the first or second modes. It is to be understood that the heater wires HW2 of the expiratory limb can be selectively controlled while the heater wires HW1 of the inspiratory limb remain in a single mode. For example, when the heater wires HW1 of the inspiratory limb are being controlled in a first mode (or a second mode), the heater wires HW2 of the expiratory limb can alternately receive or not receive power based at least in part on the operation of switches S3 and S4 without any change in control mode of the heater wires HW1. Similarly, the heater wires HW2 of the expiratory limb can remain receiving power while the heater wires HW1 of the inspiratory limb are changed between the first and second modes.

The hardware configuration 800 can include an intermediate printed circuit board (PCB) 214 that includes two diodes, with one diode being a power diode D1 and another diode being a signal diode D3. The intermediate PCB 214 can include heat pads to dissipate heat generated by the diodes D1, D3 to reduce the effects on the sensor 204a. The hardware configuration 800 can include a patient-end PCB 804 having two heater wires and a sensor 204b, wherein the heater wires 206b are directly electrically coupled. In the first mode of operation, electrical power can be provided to HW1 such that current flows through heater wires 206a and through diode D1 while substantially no current flows through heater wires 206b (e.g., less than 1% of the current through heater wires 206a flows through heater wires 206b). In the second mode of operation, electrical power can be provided to HW1 such that current flows through heater wires 206a and 206b. The first and second modes of operation can be controlled at least in part by the direction of the current flow through the heater wires HW1.

Figure 8B:
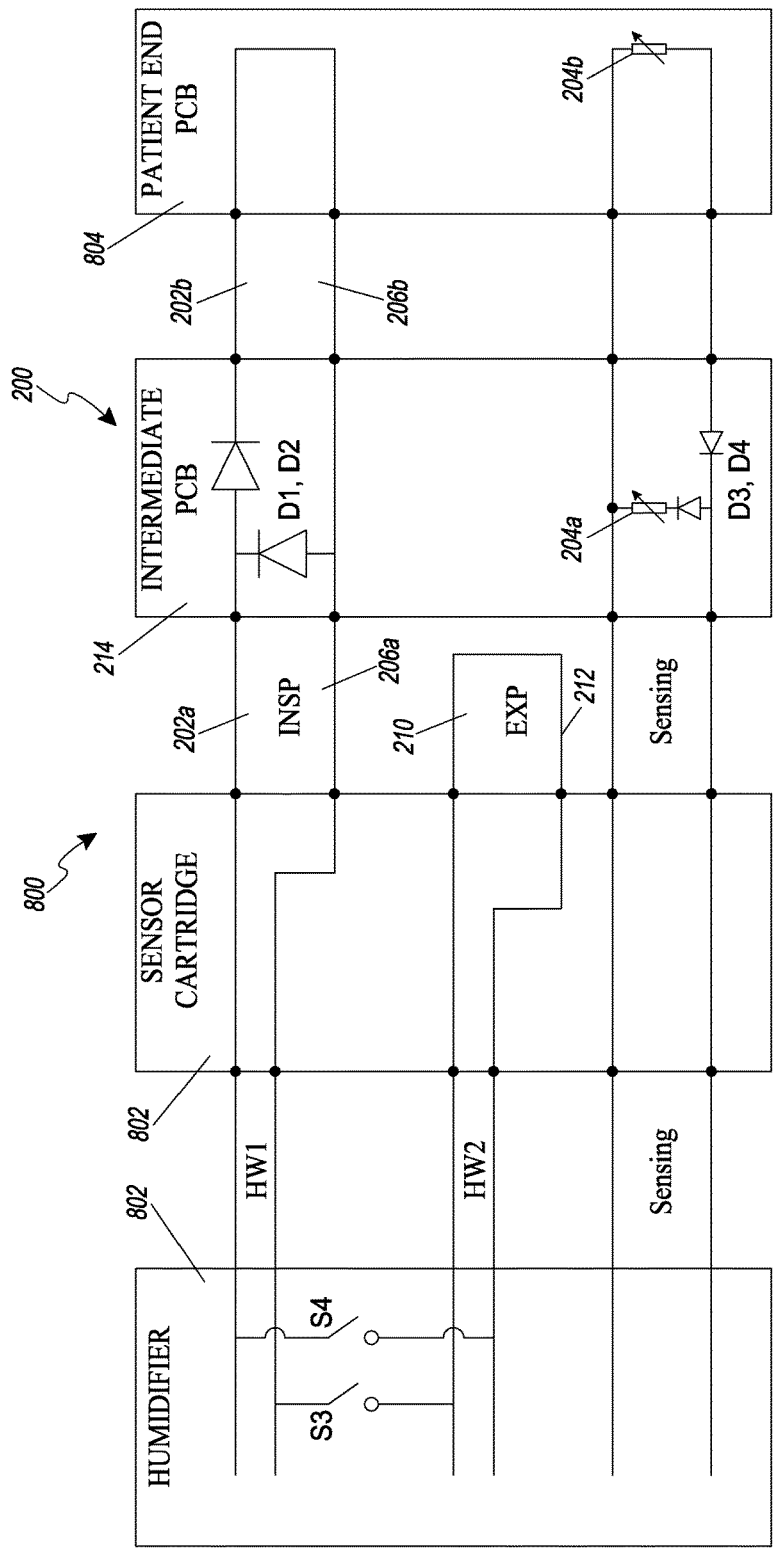

In certain embodiments, diodes D2 and D4 can be added to hardware configuration 800, as shown in FIG. 8B. In such an embodiment, the software for the sensing circuit can be altered to account for increased heat. In some embodiments, the signal diodes D3, D4 are positioned close to one another so they experience the same or similar ambient conditions to reduce differential effects caused by differing ambient temperatures. The circuit 200 otherwise operates in a manner similar to the circuit shown in FIG. 8A.

In some embodiments, comparing FIG. 8A to FIG. 8B, removing diode D4 improves patient end sensing reliability. For example, diodes can fail in an open position. If diode D4 fails open, reading the patient end temperature may not be possible. In the circuit shown in FIG. 8A, if diode D3 fails, the patient-end sensor 204b can still be read. The removal of diode D2 can have similar advantages.

In some embodiments, the sensor cartridge 802 can be located within the humidification system 100 or external to the system.

Example Segmented Inspiratory Limb with a Connector Having a Micro-controller

Figure 9:
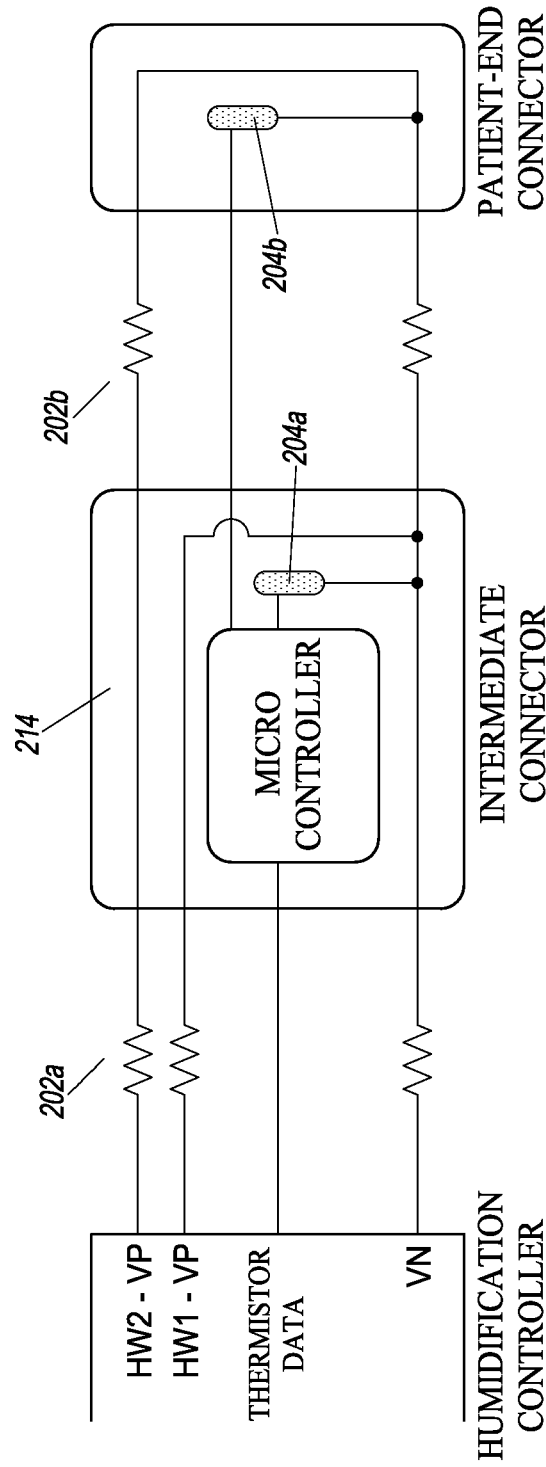
FIG. 9 illustrates an example embodiment of a humidification system that utilizes a micro-controller in an intermediate connector to measure data for controlling heating and to read sensor values in an inspiratory limb.

FIG. 9 illustrates an example embodiment of a respiratory humidification system 100 that utilizes a micro-controller in an intermediate connector 214 to measure data for controlling heating and to read sensor values in an inspiratory limb 202. In some embodiments, one or more micro-controllers can be incorporated in a sensor cartridge, in the humidifier, in the intermediate connector 214, or in any combination of these. The micro-controller provides similar functionality as described herein when incorporated on the sensor cartridge, for example. The illustrated example embodiment uses one heater wire as a common reference, the wire connected to VN, and connects the two heater wires HW1, HW2 and the sensor wires to the common reference. The example embodiment also converts both sensors' 204a, 204b readings into a digital signal in the intermediate connector 214 to send to the humidifier controller 122. This can reduce or eliminate isolation issues by referencing the sensors 204a, 204b to a common reference point and by sending a digital parameter reading which can be passed through an optocoupler on the controller 122 which will isolate the signal, as described herein with reference to FIG. 12. Using this example embodiment can allow for two independent channels of control to heat just the first section 202a or the first and second sections of the inspiratory limb 202a, 202b to provide a desired, selected, or defined heating control.

Figure 10:
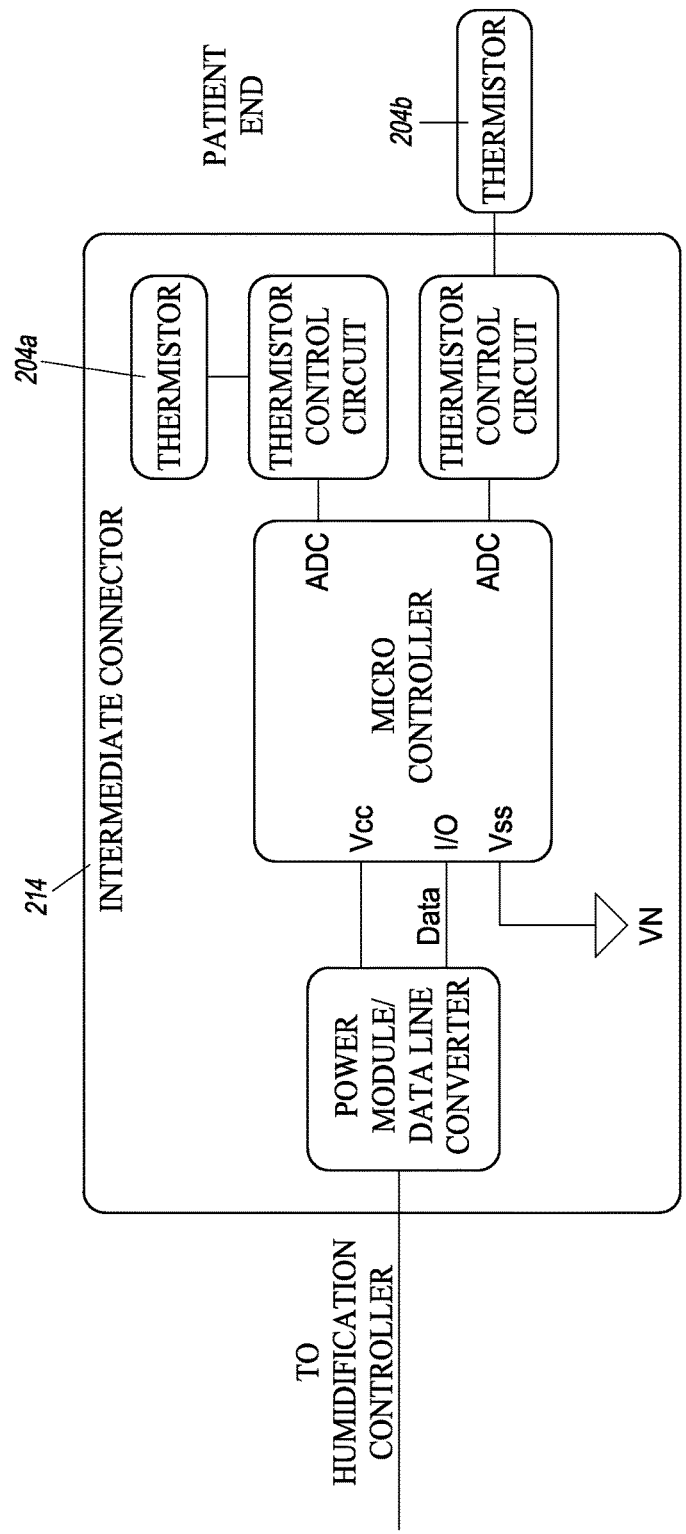
FIG. 10 illustrates a block diagram of an example intermediate connector for an inspiratory limb, wherein the intermediate connector uses a micro-controller.
Figure 11:
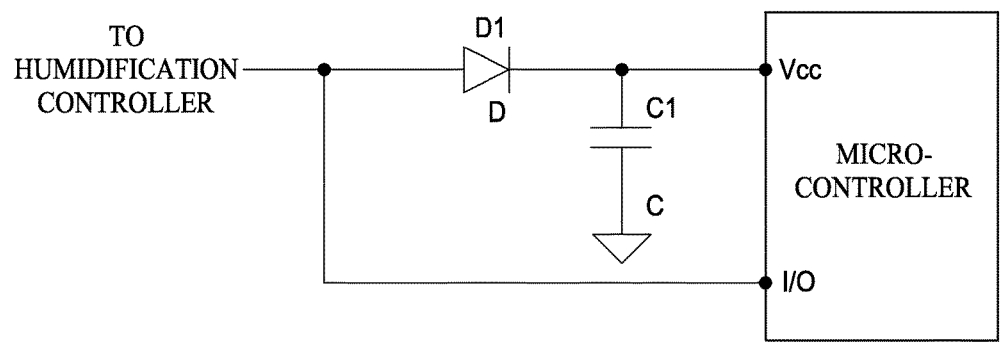
FIG. 11 illustrates a circuit diagram for an example power module and data line converter included in the intermediate connector illustrated in FIG. 10.

FIG. 10 illustrates a block diagram of an intermediate connector 214 for an inspiratory limb 202, wherein the intermediate connector 214 uses a micro-controller. The micro-controller can be used to measure an analog signal from the thermistors 204a and 204b and convert the analog signal into a digital signal using analog-to-digital converters (ADCs). The converted digital signal can be sent to the humidifier controller 122 on a single data line. The data line can be used to allow communication between the micro-controller and the humidifier controller 122 to provide temperature data. The data line can be used to provide power to the micro-controller by pulling the data line high on the humidifier controller 122 when data is not being sent. The power module and data line converter can include a capacitor and a diode so that the capacitor is charged when the data line is high. The charged capacitor can be used to power the micro-controller when the data line is being used for communication. The circuit diagram for an example power module and data line converter is illustrated in FIG. 11.

Temperature sensing using this configuration can be accomplished using a current source or a voltage source on the intermediate connector 214 to drive the thermistors so they can be read by the micro-controller. This can be done using, for example, transistors or an op-amp. Data line communication can be accomplished using a time-slot based approach where each logic level can be sent and read in a predefined time slot. In this way, one wire can be used to allow two-way communication between the humidifier controller 122 and the micro-controller.

Figure 12:
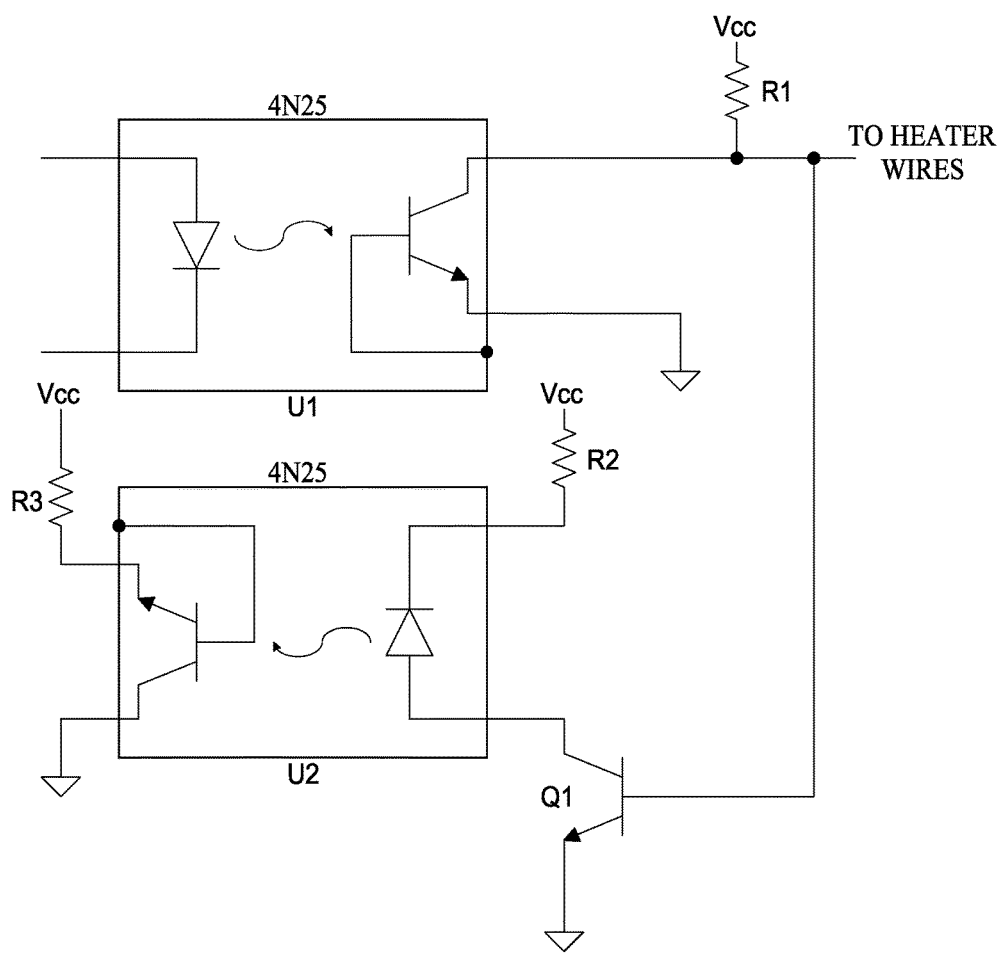
FIG. 12 illustrates a circuit diagram of an example dual optocoupler circuit used in conjunction with the intermediate connector illustrated in FIG. 10 to provide two-way data communication between a control side and an AC side on a power board.

The humidifier controller 122 can include a DC power supply that is referenced to VN. A capacitor can be included which can be charged when the heater wires are on and can provide power to the micro-controller while the heater wires are turned off. The humidifier controller 122 can include a dual optocoupler circuit 1200, as illustrated in FIG. 12. The dual optocoupler circuit can be used to isolate signals and for two-way data communication between the controller 122 and a power supply.

In some embodiments, calibration data can be stored on the micro-controller which can be read when a breathing circuit is connected. In some embodiments, part identification numbers or serial numbers can be stored to determine an origin of a connected circuit.

Segmented Inspiratory Limbs with Digital Temperature Sensors

Figure 13:
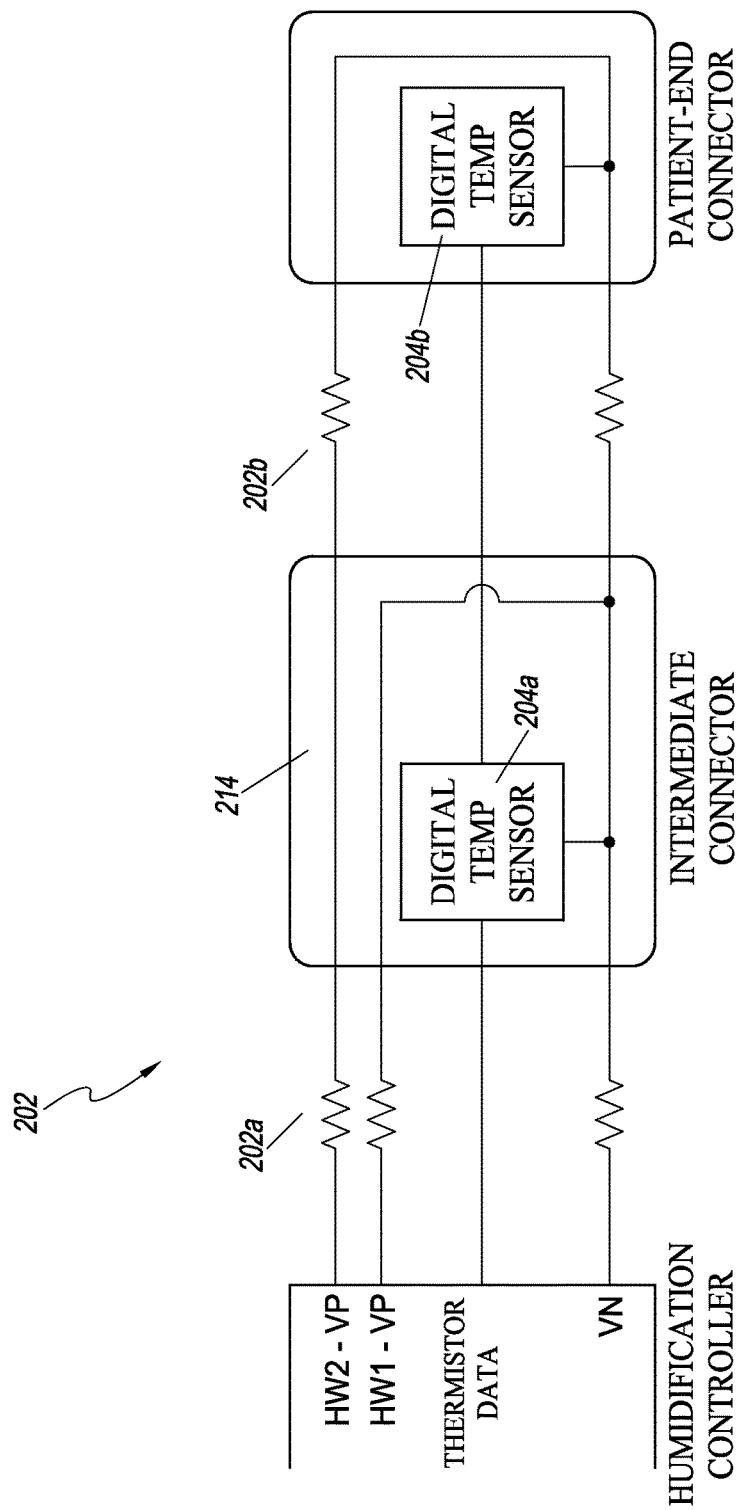
FIG. 13 illustrates a circuit diagram of an example humidification system incorporating digital temperature sensors for use with a breathing circuit having an inspiratory limb with at least two segments.

FIG. 13 illustrates a circuit diagram of an example respiratory humidification system 100 incorporating digital temperature sensors 204a, 204b for use with a breathing circuit 200 having an first segment 202a and an intermediate connector 214 coupling a second segment 202b to form the inspiratory limb 202. The digital temperature sensors 204a, 204b can utilize a single line for communication and power, simplifying circuit design and reducing an amount of wires used in the system 100, similar to the design described with reference to FIG. 9. The design illustrated in FIG. 13, can implement the temperature sensors and data communication as a single chip rather than a combination of circuit elements which may be desirable.

Intermediate Connector Board

FIGS. 14A and 14B illustrate an example intermediate PCB 250 of the intermediate connector 214, the respective figures illustrating two sides of the intermediate PCB 250. The intermediate PCB 250 includes connection pads 252, 254 for the heater wires and sensor connections. The connection pads 252, 254 are configured to be on opposite sides of the intermediate PCB 250 to facilitate connections with heater wires wound spirally around an inspiratory limb.

The intermediate PCB 250 includes sensor connection pads 256 for the sensor, such as a thermistor or other temperature measurement component, or humidity sensor, or a flow sensor, or the like. The sensor can be coupled to a diode (e.g., diode D3 described with reference to FIG. 8B) through signal connection pads 258 on the intermediate PCB

250. As illustrated, the intermediate PCB 250 includes a gap 262 configured to thermally insulate the sensor from the other electrical components and tracks. In some embodiments, the gap 262 can be filled with an insulating material to further thermally isolate the sensor connected to sensor connection pads 256. In addition, the intermediate PCB 250 can be configured to position the sensor apart from the other active and/or passive electrical components, such as with the protruding feature 257.

The intermediate PCB 250 includes power connection pad 260 for a diode electrically coupled to the heater wires through electrical tracks on the intermediate PCB 250. The diode can be the diode D1 described with reference to FIG. 3B, 6B, or 8B. The power connection pad 260 can be electrically and thermally coupled to heat sink 264 to aid in dissipating heat, to reduce or minimize effects on the accuracy of the parameter reading of the sensor coupled to the sensor connection pads 256.

FIGS. 14C and 14D illustrate example embodiments of intermediate connectors 214 comprising an intermediate PCB 250 and an intermediate connection element 263. The intermediate connection element 263 can be configured to direct a portion of the humidified gas flowing through an inspiratory limb through a conduit formed by the intermediate connection element 263. A sensor on the intermediate PCB 250 can then provide a signal corresponding to a parameter of the gas flowing through the intermediate connection element 263, the parameter being representative of at least one property (e.g., temperature, humidity, flow rate, oxygen percentage, etc.) of the humidified gas at that point in the inspiratory limb. In some embodiments, the intermediate connection element 263 is configured to provide mechanical support for the intermediate PCB 250, to position it within the inspiratory limb. In some embodiments, the intermediate connection element 263 is configured to provide mechanical support for joining two segments of an inspiratory limb together at or near the intermediate connector 214.

The intermediate connector 214 includes first connection pads 252 on a first side of the intermediate PCB 250 and second connection pads 254 on a second side of the intermediate PCB 250, the second side being on an opposite side of the intermediate PCB 250. The first and second connection pads 252, 254 can be configured to provide electrical contacts for heater wires in respective first and second segments of a segmented inspiratory limb, as described herein. In some embodiments, heater wires in a segment of an inspiratory limb are spirally wound. The intermediate PCB 250 is configured to electrically couple spirally-wound heater wires and/or signal wires (e.g., temperature sensor wires) in a first segment to spirally-wound heater wires and/or signal wires in a second segment.

In some embodiments, the intermediate PCB 250 includes a first portion extending across a lumen formed by the intermediate connection element 263 along a diameter or chord line, such that a portion of the intermediate PCB 250 generally bisects at least part of the flow path of the gas. The first portion of the intermediate PCB 250 can be overmolded by an overmolding composition. The intermediate PCB 250 can include a second portion 251 adjacent the first portion projecting outward from an exterior of the intermediate connection element 263 in a direction away from the lumen. The second portion 251 of the intermediate PCB 250 includes one or more connection pads 252 configured to receive one or more wires from a first segment of the inspiratory limb. The intermediate PCB 250 can include a third portion 253 adjacent the first portion projecting outward from the exterior of the intermediate connection element 263 in a direction away from the lumen and in a direction opposite the second portion 251. The third portion 253 can include one or more connection pads 254 on the intermediate PCB 250 configured to receive one or more wires from a second segment of the inspiratory limb. The intermediate PCB 250 can include one or more conductive tracks configured to electrically couple the one or more connection pads 252 of the second portion 251 to the one or more connection pads 254 of the third portion 253 and configured to provide an electrical connection between the wires in the first segment and the wires in the second segment of the inspiratory limb.

Patient-End Connector Board

Figure 15A:
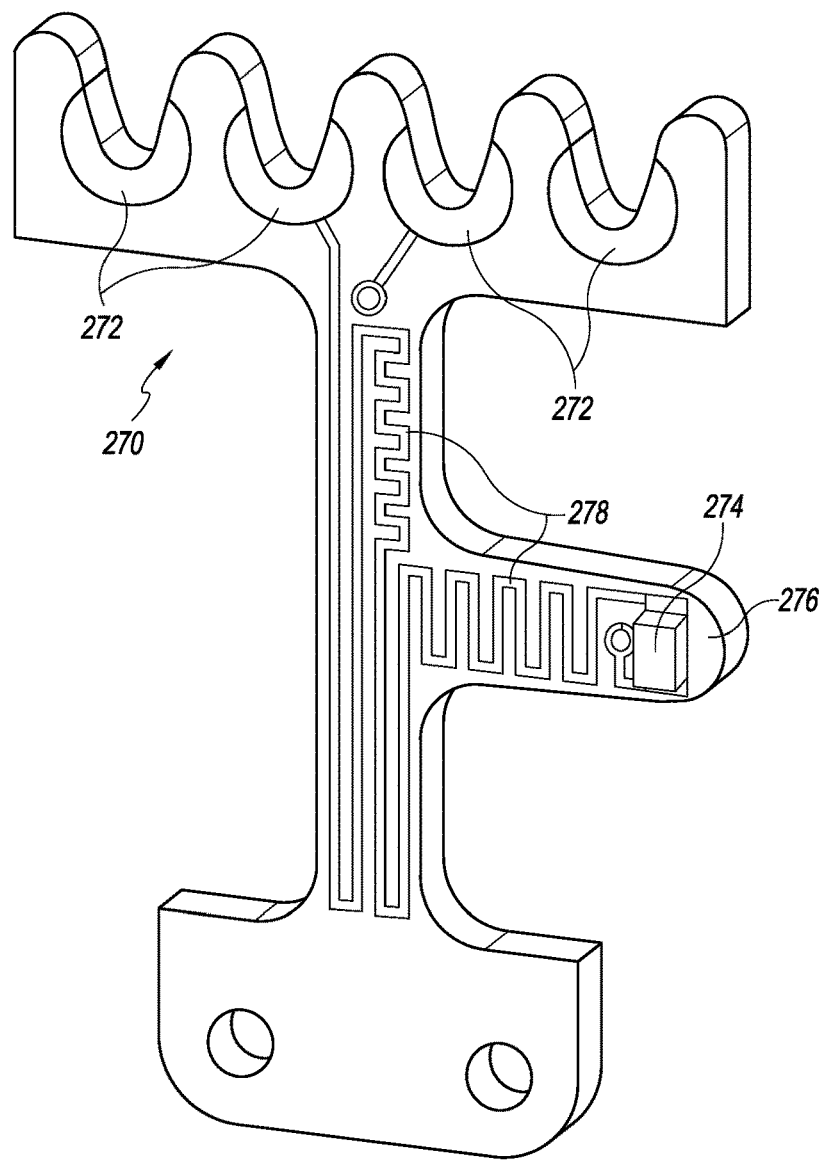
FIG. 15A illustrates an example PCB for a patient-end connector.

FIG. 15A illustrates an example patient-end PCB 270 of the patient-end connector 804. The patient-end PCB 270 includes connection pads 272 for the heater wires and sensor connections. The connection pads 272 are configured to be on only one side of the patient-end PCB 270 to connect to spirally wound heater and signal wires from the inspiratory limb. Two of the connection pads 272 can be directly electrically coupled to one another as an electrical pass-through. The heater wires can be coupled to the connection pads 272 which are directly electrically coupled. The remaining two connection pads 272 can be electrically coupled to the sensor connection pads 274. The electrical tracks 278 to and from the sensor connection pads 274 can be configured to reduce or minimize the width of the trace and increase or maximize the length of the track to thermally isolate the sensor connected to the sensor connection pads 274. The patient-end PCB 270 can include a similar protruding feature 276 as was described with reference to the PCB 250 illustrated in FIGS. 14A and 14B. The protruding feature 276 can be configured to further thermally isolate the sensor from the effects of the electrical current and components on the patient-end PCB 270.

Figure 15B:
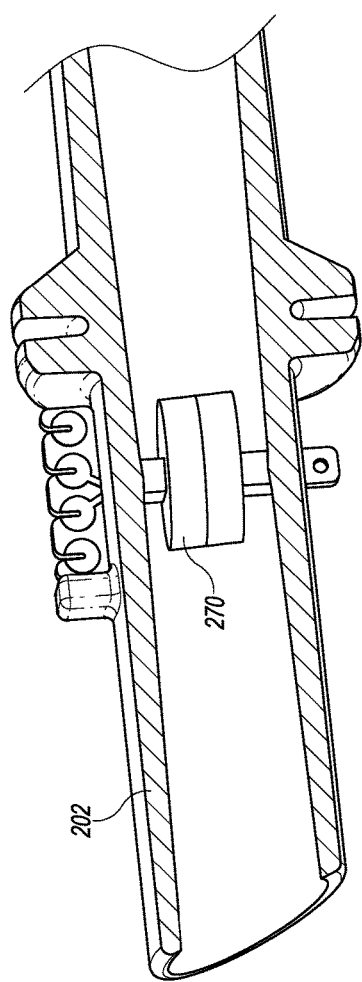
Figure 15C:
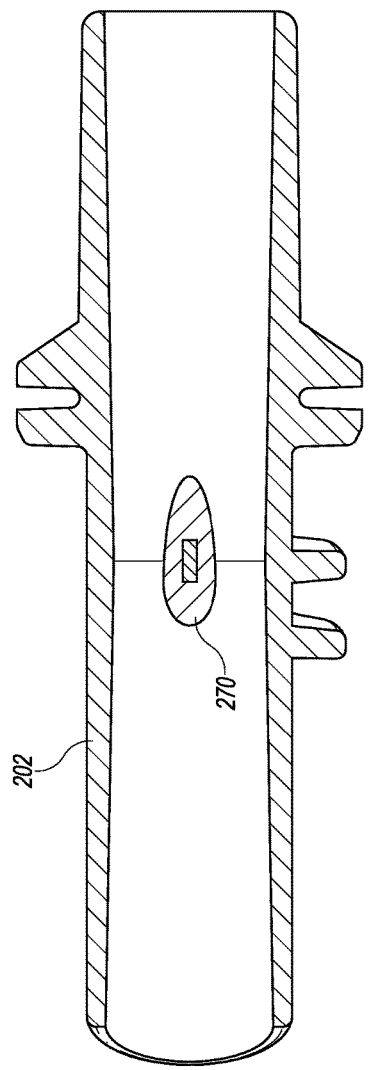

FIGS. 15B-15E illustrate example embodiments of the patient-end connectors 804. FIGS. 15B and 15D illustrate example embodiments of the patient-end PCB 270 over-molded as part of the inspiratory limb 202. The cross-section of the patient-end PCB 270, illustrated respectively in FIGS. 15C and 15E, can be configured to be aerodynamic to reduce or minimize turbulence in the gasses being delivered to the patient.

Segmented Inspiratory Limb Placement Limiters

Figure 16A:
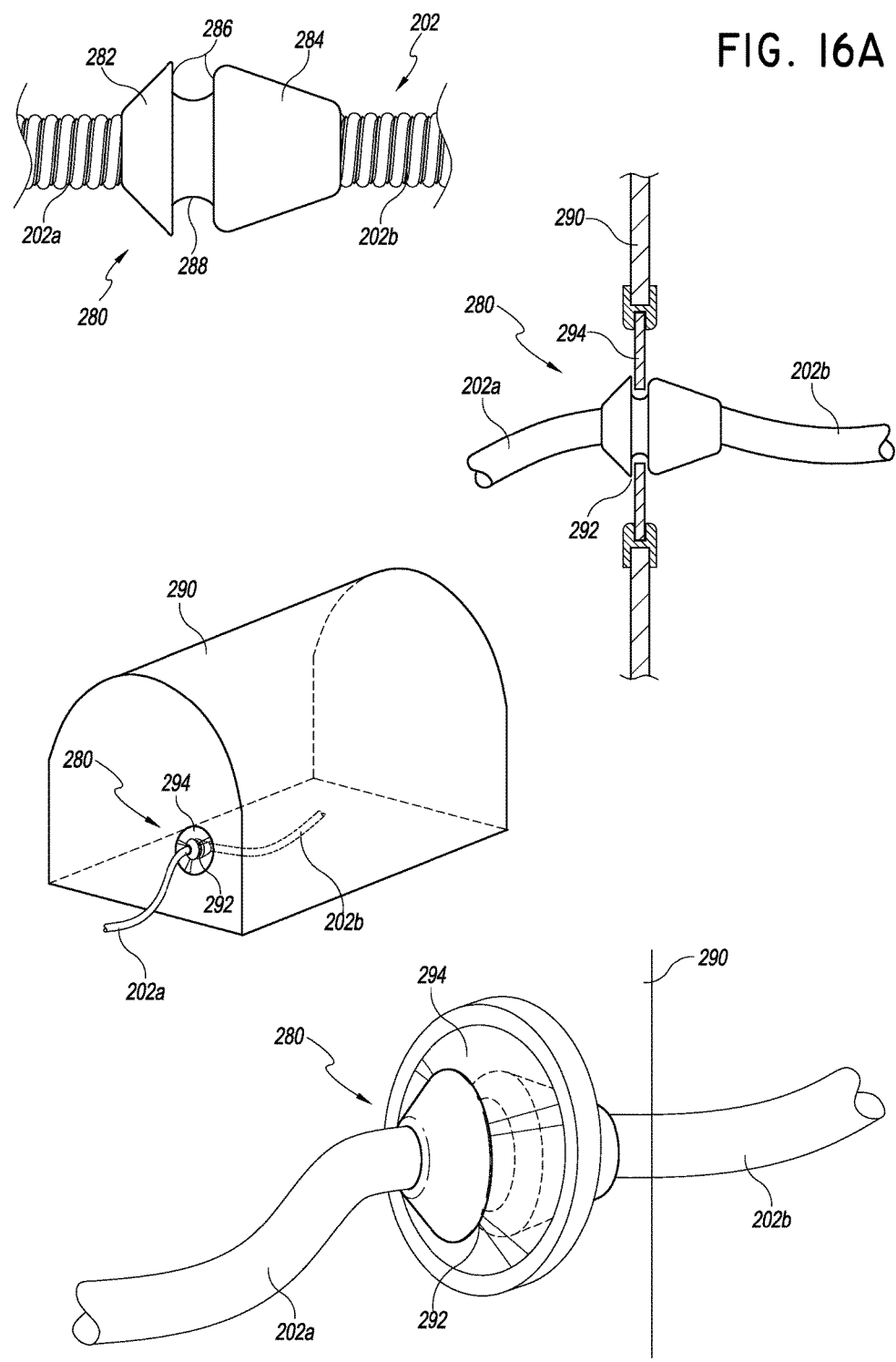
FIGS. 16A-16E illustrate example embodiments of placement limiters for a segmented inspiratory limb.
Figure 16B:
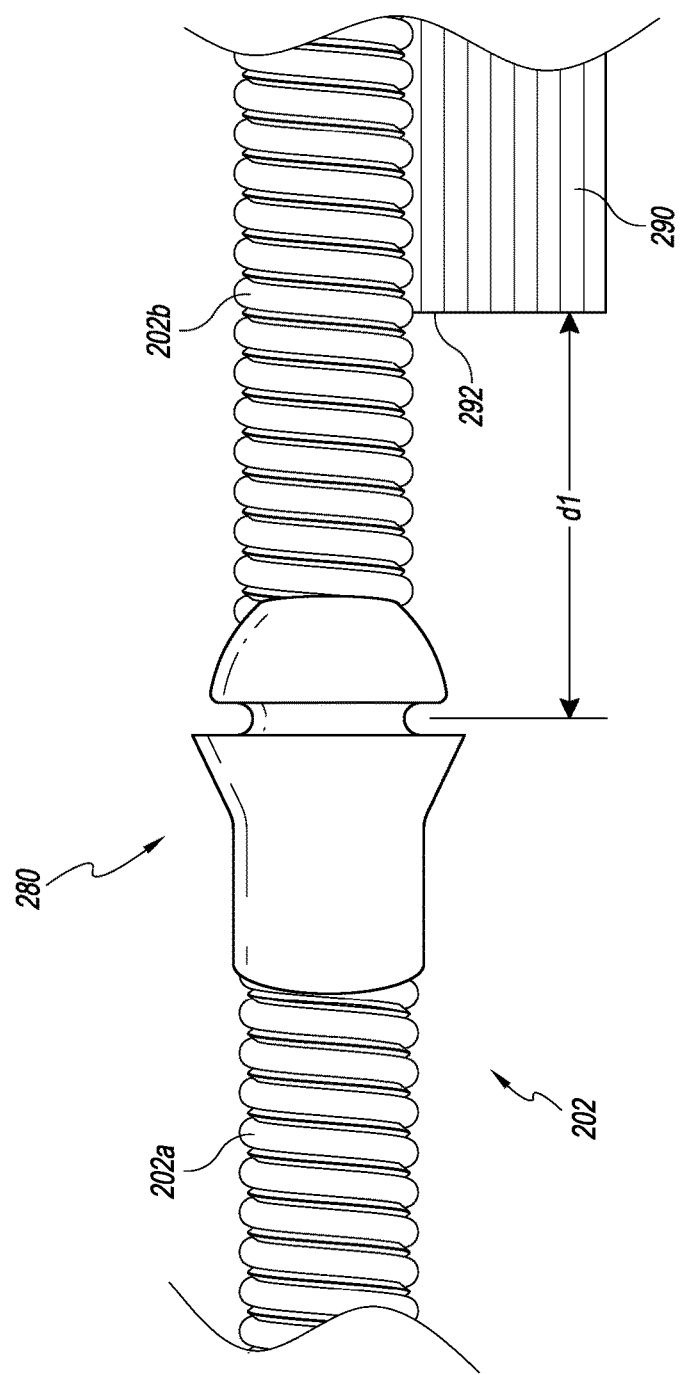

FIGS. 16A-16E illustrate example embodiments of placement limiters 280 for a segmented inspiratory limb 202. FIG. 16A illustrates an example placement limiter 280 configured with a larger chamber end 282 (e.g., an end nearer a gas supply), a smaller patient end 284, and sharp corners 286 with a groove 288 into which a grommet 294 can be placed. The placement limiter 280 can be configured to prevent or reduce the probability that the intermediate connector or the segment connection point of the inspiratory limb 202 (e.g., where the intermediate PCB 250 is located), enters the incubator 290 through the opening 292. The smaller end 284 can be configured to enter the incubator 290 while the larger end 282 can be configured to prevent or resist entry through the incubator opening 292 through contact with the grommet 294. In some embodiments, the placement limiter 280 is configured to substantially secure the location of the intermediate PCB 250 within a targeted or desired distance from the incubator or other such point defining a different temperature environment. The targeted or desired distance can be less than or equal to about 20 cm, less than or equal to about 10 cm, less than or equal to about 5 cm, or about 0 cm. FIG. 16B shows the example placement limiter 280 used with a bubble tube 202 where the placement limiter is located a distance d1 from the entrance 292 to the incubator 290.

Figure 16C:
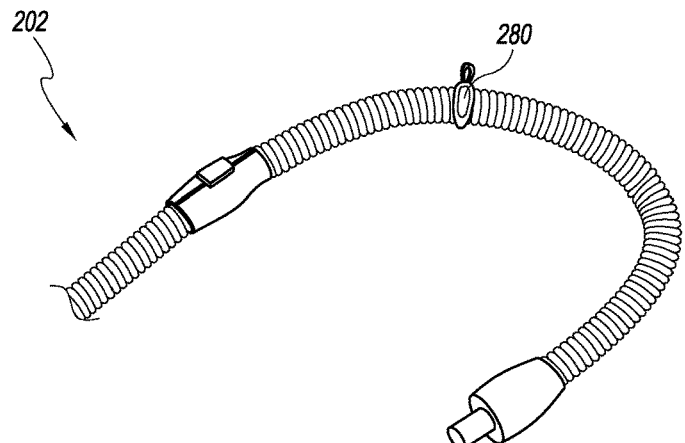
Figure 16D:
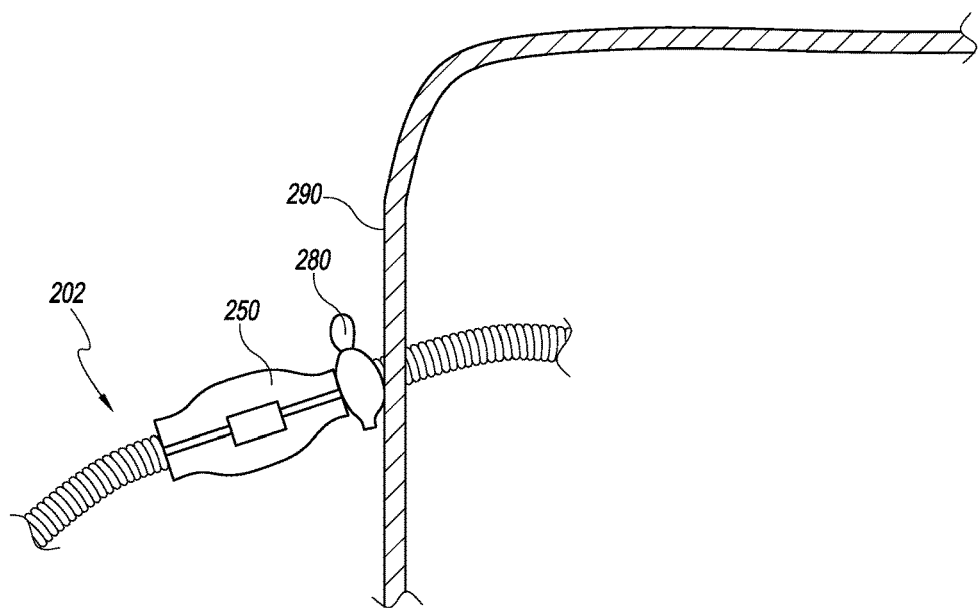
Figure 16E:
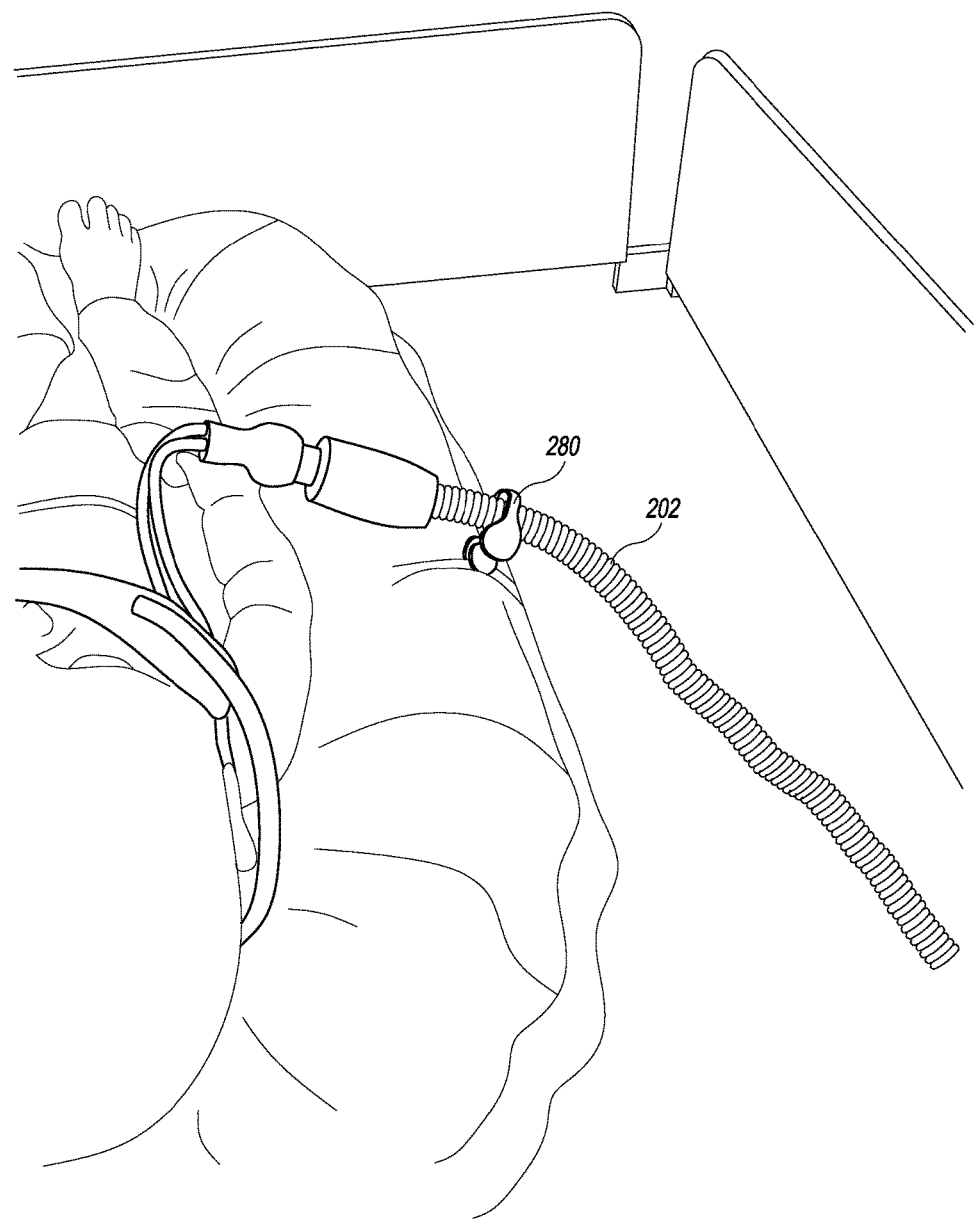

FIG. 16C illustrates an example embodiment of a placement limiter 280 configured to clip or be secured to an object, such as clothing, a blanket, or another object that is separate from the patient. The placement limiter 280 is secured to an inspiratory limb 202 and is configured to be able to be moved along the inspiratory limb 202 to adjust the placement of the inspiratory limb 202. FIG. 16D illustrates the inspiratory limb 202 with the placement limiter 280 in use with an incubator 290 to resist or prevent entry of the intermediate PCB connector 250 into the incubator 290. FIG. 16E illustrates the inspiratory limb 202 with the placement limiter 280 in use with a patient where the placement limiter 280 is secured to a blanket of the patient to resist or prevent movement inspiratory limb 202 relative to the patient and/or the blanket. The placement limiter 280 can also be used with an expiratory limb or other medical tube used in conjunction with gas delivery systems.

Segmented Medical Tubing for Use with Respiratory Humidification Systems

Figure 17A:
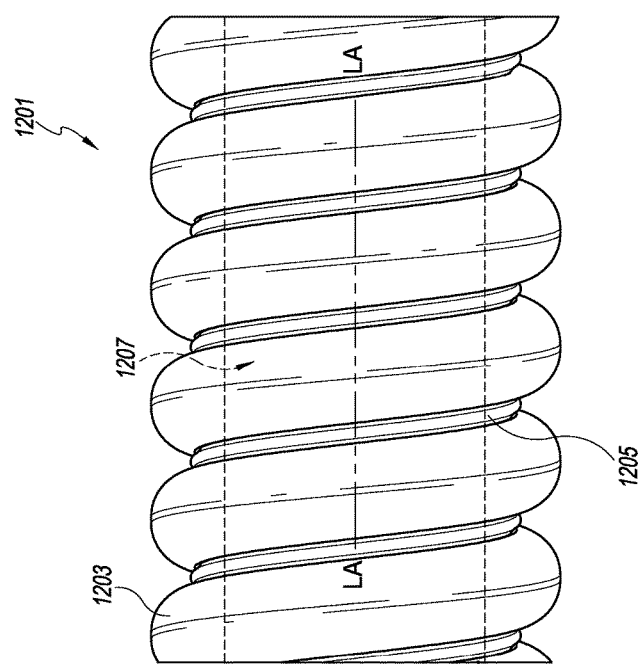
FIG. 17A shows a side-plan view of a section of an example composite tube.

FIG. 17A shows a side-plan view of a section of example composite tube 1201 which can be used in conjunction with the respiratory humidification system 100 described with reference to FIG. 1. The composite tube 1201 can be used as the inspiratory limb 202 and can be configured, as described herein, to provide thermally beneficial properties that assist in the prevention of condensation of gases along the tube. The composite tube 1201 includes a plurality of elongate members wrapped and joined to form a passageway, where the plurality of elongate members can include one or more of the heater wires described herein. Based at least in part on the heater wires being embedded in the walls of the composite tube 1201, the use of the composite tube 1201 as the inspiratory limb 202 can reduce condensation and rain out and maintain a more desirable or targeted temperature profile along the length of the inspiratory limb 202. The composite tube's walls can provide a greater thermal mass which resists temperature changes and increases the insulating effects of the walls in relation to the ambient temperature outside the limb 202. As a result, the temperature along the length of the limb 202, including through any number of differing temperature environments, can be more accurately controlled and less power or energy can be expended in controlling the temperature of the gases delivered to the patient. In some embodiments, the composite tube 1201 can be used as the expiratory limb 210.

In general, the composite tube 1201 comprises a first elongate member 1203 and a second elongate member 1205. Member is a broad term and is to be given its ordinary and customary meaning to a person of ordinary skill in the art (i.e., it is not to be limited to a special or customized meaning) and includes, without limitation, integral portions, integral components, and distinct components. Thus, although FIG. 17A illustrates an embodiment made of two distinct components, it will be appreciated that in other embodiments, the first elongate member 1203 and second elongate member 1205 can also represent regions in a tube formed from a single material. Thus, the first elongate member 1203 can represent a hollow portion of a tube, while the second elongate member 1205 represents a structural supporting or reinforcement portion of the tube which adds structural support to the hollow portion. The hollow portion and the structural supporting portion can have a spiral configuration, as described herein. The composite tube 1201 may be used to form the inspiratory limb 202 and/or the expiratory limb 210 as described herein, a coaxial tube as described below, or any other tubes as described elsewhere in this disclosure.

In this example, the first elongate member 1203 comprises a hollow body spirally wound to form, at least in part, an elongate tube having a longitudinal axis LA-LA and a lumen 1207 extending along the longitudinal axis LA-LA. In at least one embodiment, the first elongate member 1203 is a tube. Preferably, the first elongate member 1203 is flexible. Furthermore, the first elongate member 1203 is preferably transparent or, at least, semi-transparent or semi-opaque. A degree of optical transparency allows a caregiver or user to inspect the lumen 1207 for blockage or contaminants or to confirm the presence of moisture. A variety of plastics, including medical grade plastics, are suitable for the body of the first elongate member 1203. Examples of suitable materials include Polyolefin elastomers, Polyether block amides, Thermoplastic co-polyester elastomers, EPDM-Polypropylene mixtures, and Thermoplastic polyurethanes.

The hollow body structure of the first elongate member 1203 contributes to the insulating properties to the composite tube 1201. An insulating tube 1201 is desirable because, as explained herein, it prevents or reduces heat loss. This can allow the tube 1201 to deliver gas from a heater-humidifier to a patient while substantially maintaining the gas's conditioned state with reduced or minimal energy consumption.

In at least one embodiment, the hollow portion of the first elongate member 1203 is filled with a gas. The gas can be air, which is desirable because of its low thermal conductivity ($2.62 \times 10^{-2}$ W/m·K at 300K) and very low cost. A gas that is more viscous than air may also advantageously be used, as higher viscosity reduces convective heat transfer. Thus, gases such as argon ($17.72 \times 10^{-3}$ W/m·K at 300K), krypton ($9.43 \times 10^{-3}$ W/m·K at 300K), and xenon ($5.65 \times 10^{-3}$ W/m·K at 300K) can increase insulating performance. Each of these gases is non-toxic, chemically inert, fire-inhibiting, and commercially available. The hollow portion of the first elongated member 1203 can be sealed at both ends of the tube, causing the gas within to be substantially stagnant. Alternatively, the hollow portion can be a secondary pneumatic connection, such as a pressure sample line for conveying pressure feedback from the patient-end of the tube to a controller. The first elongate member 1203 can be optionally perforated. For instance, the surface of the first elongate member 1203 can be perforated on an outward-facing surface, opposite the lumen 1207. In another embodiment, the hollow portion of the first elongate member 1203 is filled with a liquid. Examples of liquids can include water or other biocompatible liquids with a high thermal capacity. For instance, nanofluids can be used. An example nanofluid with suitable thermal capacity comprises water and nanoparticles of substances such as aluminum.

The second elongate member 1205 is also spirally wound and joined to the first elongate member 1203 between adjacent turns of the first elongate member 1203. The second elongate member 1205 forms at least a portion of the lumen 1207 of the elongate tube. The second elongate member 1205 acts as structural support for the first elongate member 1203.

In at least one embodiment, the second elongate member 1205 is wider at the base (proximal the lumen 1207) and narrower at the top. For example, the second elongate member can be generally triangular in shape, generally T-shaped, or generally Y-shaped. However, any shape that meets the contours of the corresponding first elongate member 1203 is suitable.

Preferably, the second elongate member 1205 is flexible, to facilitate bending of the tube. Desirably; the second elongate member 1205 is less flexible than the first elongate member 1203. This improves the ability of the second elongate member 1205 to structurally support the first elongate member 1203. For example, the modulus of the second elongate member 1205 is preferably 30-50 MPa (or about 30-50 MPa). The modulus of the first elongate member 1203 is less than the modulus of the second elongate member 1205. The second elongate member 1205 can be solid or mostly solid. In addition, the second elongate member 1205 can encapsulate or house conductive material, such as filaments, and specifically heating filaments or sensors (not shown). Heating filaments can minimize the cold surfaces onto which condensate from moisture-laden air can form. Heating filaments can also be used to alter the temperature profile of gases in the lumen 1207 of composite tube 1201. A variety of polymers and plastics, including medical grade plastics, are suitable for the body of the second elongate member 1205. Examples of suitable materials include Poly-olefin elastomers, Polyether block amides, Thermoplastic co-polyester elastomers, EPDM-Polypropylene mixtures and Thermoplastic polyurethanes. In certain embodiments, the first elongate member 1203 and the second elongate member 1205 may be made from the same material. The second elongate member 1205 may also be made of a different color material from the first elongate member 1203, and may be transparent, translucent or opaque. For example, in one embodiment the first elongate member 1203 may be made from a clear plastic, and the second elongate member 1205 may be made from an opaque blue (or other color) plastic.

This spirally-wound structure comprising a flexible, hollow body and an integral support can provide crush resistance, while leaving the tube wall flexible enough to permit short-radius bends without kinking, occluding or collapsing. Preferably, the tube can be bent around a 25 mm diameter metal cylinder without kinking, occluding, or collapsing, as defined in the test for increase in flow resistance with bending according to ISO 5367:2000(E). This structure also can provide a smooth lumen 1207 surface (tube bore), which helps keep the tube free from deposits and improves gas flow. The hollow body has been found to improve the insulating properties of a tube, while allowing the tube to remain light weight.

As explained above, the composite tube 1201 can be used as an expiratory tube and/or an inspiratory tube in a breathing circuit, or a portion of a breathing circuit. Preferably, the composite tube 1201 is used at least as an inspiratory tube.

Figure 17B:
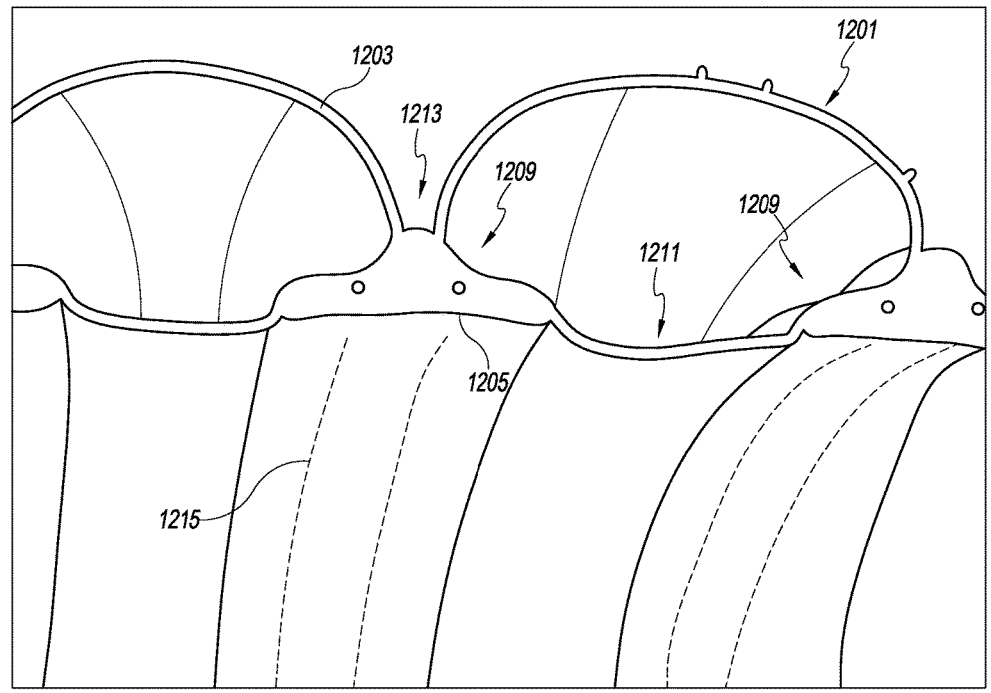
FIG. 17B shows a longitudinal cross-section of a top portion a tube similar to the example composite tube of FIG. 17A.

FIG. 17B shows a longitudinal cross-section of a top portion of the example composite tube 1201 of FIG. 17A. FIG. 17B has the same orientation as FIG. 17A. This example further illustrates the hollow-body shape of the first elongate member 1203. As seen in this example, the first elongate member 1203 forms in longitudinal cross-section a plurality of hollow bubbles. Portions 1209 of the first elongate member 1203 overlap adjacent wraps of the second elongate member 1205. A portion 1211 of the first elongate member 1203 forms the wall of the lumen (tube bore).

It was discovered that having a gap 1213 between adjacent turns of the first elongate member 1203, that is, between adjacent bubbles, unexpectedly improved the overall insulating properties of the composite tube 1201. Thus, in certain embodiments, adjacent bubbles are separated by a gap 1213. Furthermore, certain embodiments include the realization that providing a gap 1213 between adjacent bubbles increases the heat transfer resistivity (the R value) and, accordingly, decreases the heat transfer conductivity of the composite tube 1201. This gap configuration was also found to improve the flexibility of the composite tube 1201 by permitting shorter-radius bends. A T-shaped second elongate member 1205, as shown in FIG. 17B, can help maintain a gap 1213 between adjacent bubbles. Nevertheless, in certain embodiments, adjacent bubbles are touching. For example, adjacent bubbles can be bonded together.

One or more conductive materials can be disposed in the second elongate member 1205 for heating or sensing the gas flow. In this example, two heating filaments 1215 are encapsulated in the second elongate member 1205, one on either side of the vertical portion of the "T." The heating filaments 1215 comprise conductive material, such as alloys of Aluminum (Al) and/or Copper (Cu), or conductive polymer. Preferably, the material forming the second elongate member 1205 is selected to be non-reactive with the metal in the heating filaments 1215 when the heating filaments 1215 reach their operating temperature. The filaments 1215 may be spaced away from lumen 1207 so that the filaments are not exposed to the lumen 1207. At one end of the composite tube, pairs of filaments can be formed into a connecting loop.

In at least one embodiment, a plurality of filaments are disposed in the second elongate member 1205. The filaments can be electrically connected together to share a common rail. For example, a first filament, such as a heating filament, can be disposed on a first side of the second elongate member 1205. A second filament, such as a sensing filament, can be disposed on a second side of the second elongate member 1205. A third filament, such as a ground filament, can be disposed between the first and second filaments. The first, second, and/or third filaments can be connected together at one end of the second elongate member 1205.

Figure 17C:
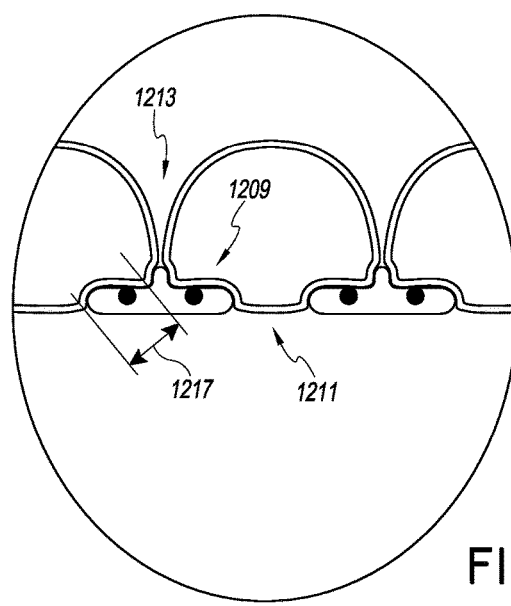
FIG. 17C shows another longitudinal cross-section illustrating a first elongate member in the composite tube.
Figure 17D:
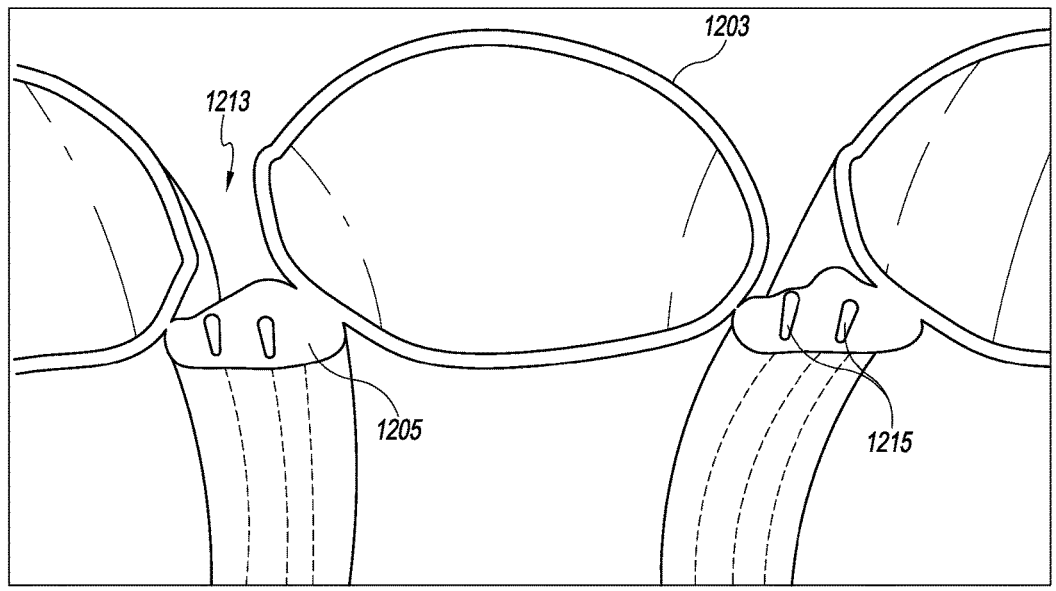
FIG. 17D shows another longitudinal cross-section of a top portion of a tube.
Figure 19A:
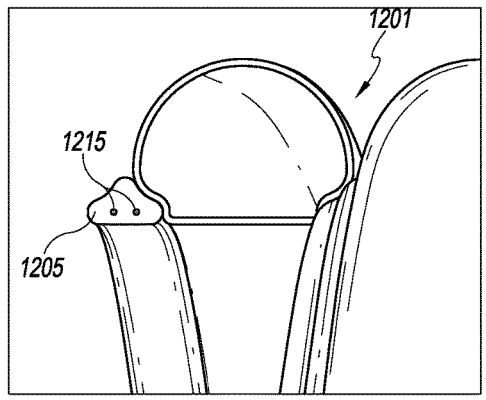
FIGS. 19A-C show examples of first elongate member shapes configured to improve thermal efficiency.
Figure 19B:
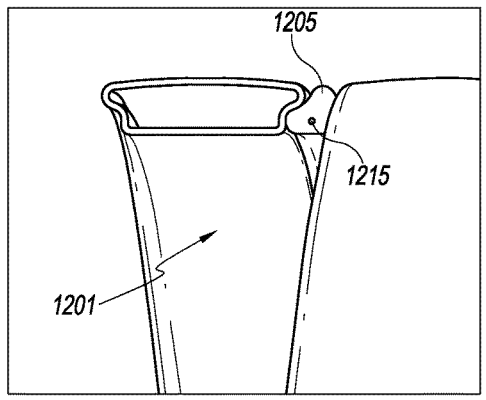
Figure 19C:
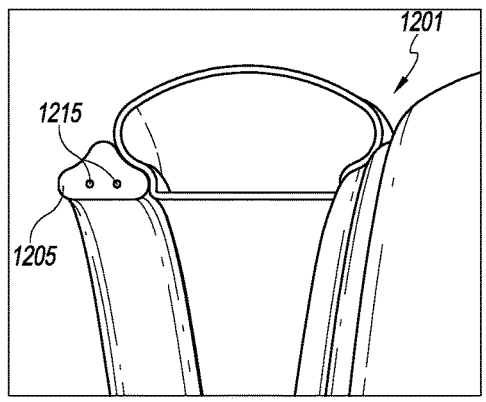

FIG. 17C shows a longitudinal cross-section of the bubbles in FIG. 17B. As shown, the portions 1209 of the first elongate member 1203 overlapping adjacent wraps of the second elongate member 1205 are characterized by a degree of bond region 1217. A larger bond region improves the tubes resistance to delamination at the interface of the first and second elongate members. Additionally or alternatively, the shape of the bead and/or the bubble can be adapted to increase the bond region 1217. For example, FIG. 17D shows a relatively small bonding area on the left-hand side. FIG. 19B also demonstrates a smaller bonding region. In contrast, FIG. 17E has a much larger bonding region than that shown in FIG. 17D, because of the size and shape of the bead. FIGS. 19A and 19C also illustrate a larger bonding region. Each of these figures is discussed in more detail below. It should be appreciated that although the configurations in FIGS. 17E, 19A, and 19C may be preferred in certain embodiments, other configurations, including those of FIGS. 17D, 19B, and other variations, may be utilized in other embodiments as may be desired.

FIG. 17D shows a longitudinal cross-section of a top portion of another composite tube. FIG. 17D has the same orientation as FIG. 17B. This example further illustrates the hollow-body shape of the first elongate member 1203 and demonstrates how the first elongate member 1203 forms in longitudinal cross-section a plurality of hollow bubbles. In this example, the bubbles are completely separated from each other by a gap 1213. A generally triangular second elongate member 1205 supports the first elongate member 1203.

Figure 17E:
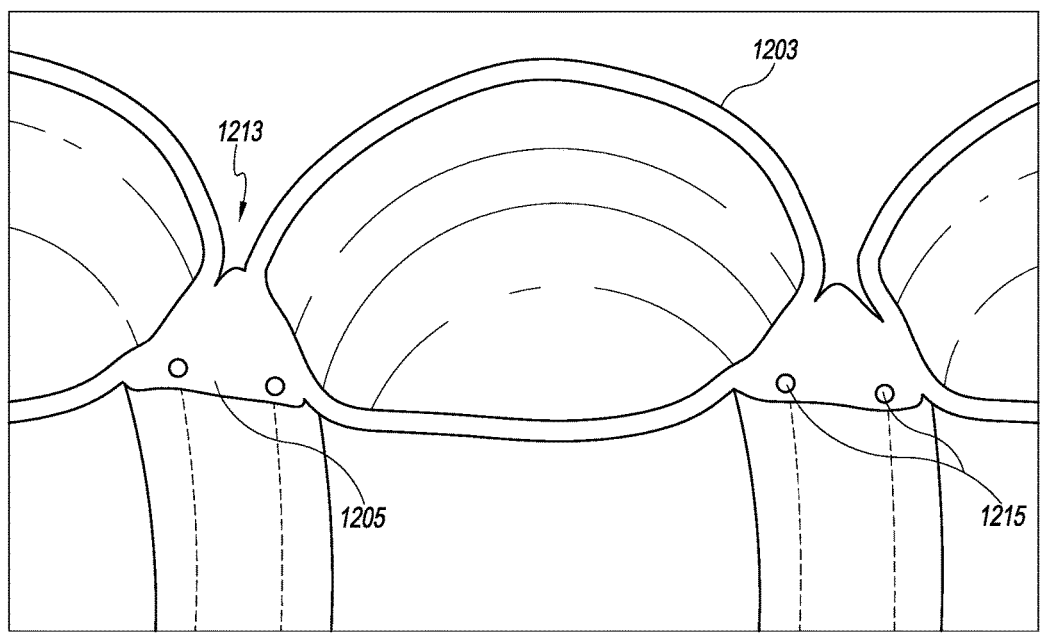
FIG. 17E shows another longitudinal cross-section of a top portion of a tube.

FIG. 17E shows a longitudinal cross-section of a top portion of another composite tube. FIG. 17E has the same orientation as FIG. 17B. In the example of FIG. 17E, the heating filaments 1215 are spaced farther apart from each other than the filaments 1215 in FIG. 17B. It was discovered that increasing the space between heating filaments can improve heating efficiency, and certain embodiments include this realization. Heating efficiency refers to the ratio of the amount of heat input to the tube to the amount of energy output or recoverable from the tube. Generally speaking, the greater the energy (or heat) that is dissipated from the tube, the lower the heating efficiency. For improved heating performance, the heating filaments 1215 can be equally (or about equally) spaced along the bore of the tube. Alternatively, the filaments 1215 can be positioned at extremities of the second elongate member 1205, which may provide simpler manufacturing.

Figure 18A:
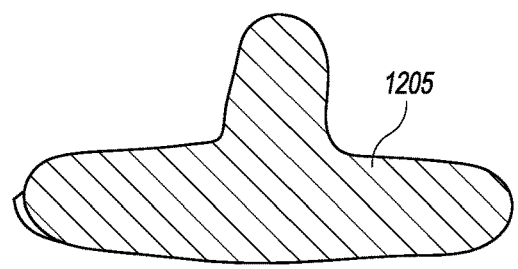
FIG. 18A shows a transverse cross-section of a second elongate member in the composite tube.

Reference is next made to FIGS. 18A through 18G which demonstrate example configurations for the second elongate member 1205. FIG. 18A shows a cross-section of a second elongate member 1205 having a shape similar to the T-shape shown in FIG. 17B. In this example embodiment, the second elongate member 1205 does not have heating filaments. Other shapes for the second elongate member 1205 may also be utilized, including variations of the T-shape as described below and triangular shapes.

Figure 18B:
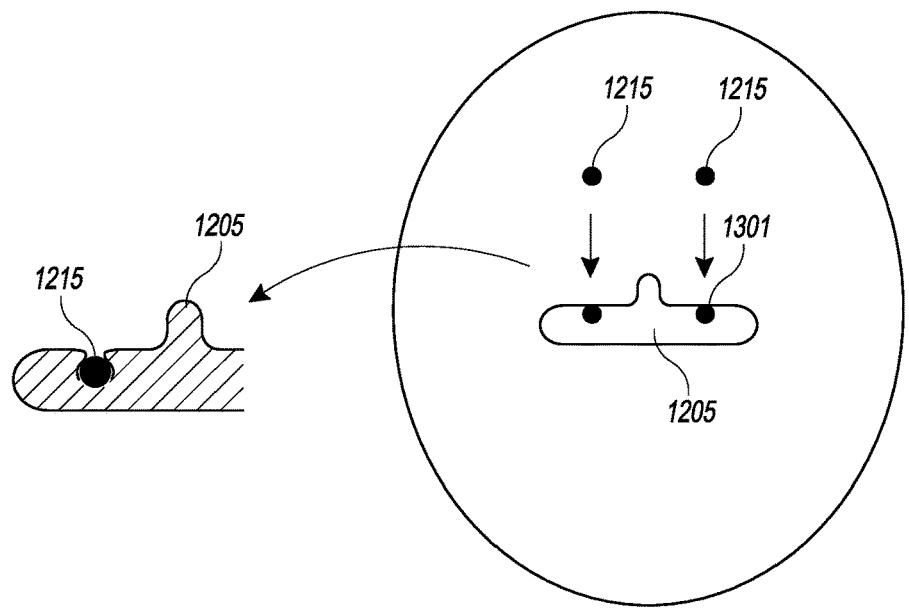
FIG. 18B shows another transverse cross-section of a second elongate member.

FIG. 18B shows another example second elongate member 1205 having a T-shape cross-section. In this example, heating filaments 1215 are embedded in cuts 1301 in the second elongate member 1205 on either side of the vertical portion of the "T." In some embodiments, the cuts 1301 can be formed in the second elongate member 1205 during extrusion. The cuts 1301 can alternatively be formed in the second elongate member 1205 after extrusion. For example, a cutting tool can form the cuts in the second elongate member 1205. Preferably, the cuts are formed by the heating filaments 1215 as they are pressed or pulled (mechanically fixed) into the second elongate member 1205 shortly after extrusion, while the second elongate member 1205 is relatively soft. Alternatively, one or more heating filaments can be mounted (e.g., adhered, bonded, or partially embedded) on the base of the elongate member, such that the filament(s) are exposed to the tube lumen. In such embodiments, it can be desirable to contain the filament(s) in insulation to reduce the risk of fire when a flammable gas such as oxygen is passed through the tube lumen.

Figure 18C:
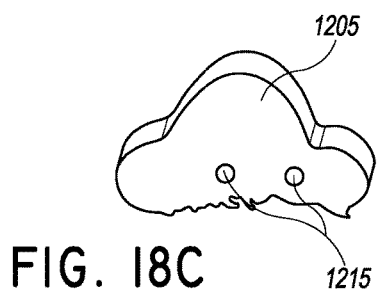
FIG. 18C shows another example second elongate member.

FIG. 18C shows yet another example second elongate member 1205 in cross-section. The second elongate member 1205 has a generally triangular shape. In this example, heating filaments 1215 are embedded on opposite sides of the triangle.

Figure 18D:
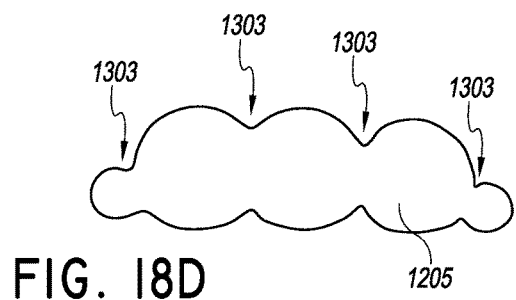
FIG. 18D shows another example second elongate member.

FIG. 18D shows yet another example second elongate member 1205 in cross-section. The second elongate member 1205 comprises four grooves 1303. The grooves 1303 are indentations or furrows in the cross-sectional profile. In some embodiments, the grooves 1303 can facilitate the formation of cuts (not shown) for embedding filaments (not shown). In some embodiments, the grooves 1303 facilitate the positioning of filaments (not shown), which are pressed or pulled into, and thereby embedded in, the second elongate member 1205. In this example, the four initiation grooves 1303 facilitate placement of up to four filaments, e.g., four heating filaments, four sensing filaments, two heating filaments and two sensing filaments, three heating filaments and one sensing filament, or one heating filament and three sensing filaments. In some embodiments, heating filaments can be located on the outside of the second elongate member 1205. Sensing filaments can be located on the inside.

Figure 18E:
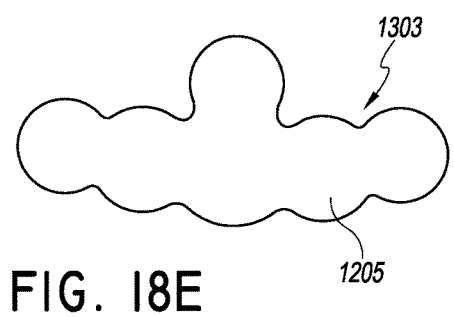
FIG. 18E shows another example second elongate member.

FIG. 18E shows still another example second elongate member 1205 in cross-section. The second elongate member 1205 has a T-shape profile and a plurality of grooves 1303 for placing heating filaments.

Figure 18F:
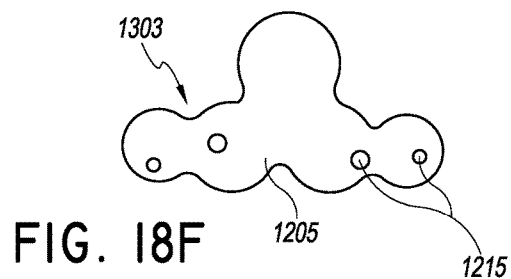
FIG. 18F shows another example second elongate member.

FIG. 18F shows yet another example second elongate member 1205 in cross-section. Four filaments 1215 are encapsulated in the second elongate member 1205, two on either side of the vertical portion of the "T." As explained in more detail below, the filaments are encapsulated in the second elongate member 1205 because the second elongate member 1205 was extruded around the filaments. No cuts were formed to embed the heating filaments 1215. In this example, the second elongate member 1205 also comprises a plurality of grooves 1303. Because the heating filaments 1215 are encapsulated in the second elongate member 1205, the grooves 1303 are not used to facilitate formation of cuts for embedding heating filaments. In this example, the grooves 1303 can facilitate separation of the embedded heating filaments, which makes stripping of individual cores easier when, for example, terminating the heating filaments.

FIG. 18G shows yet another example second elongate member 1205 in cross-section. The second elongate member 1205 has a generally triangular shape. In this example, the shape of the second elongate member 1205 is similar to that of FIG. 18C, but four filaments 1215 are encapsulated in the second elongate member 1205, all of which are central in the bottom third of the second elongate member 1205 and disposed along a generally horizontal axis.

As explained above, it can be desirable to increase the distance between filaments to improve heating efficiency. In some embodiments, however, when heating filaments 1215 are incorporated into the composite tube 1201, the filaments 1215 can be positioned relatively central in the second elongate member 1205. A centralized position promotes robustness of the composite tubing for reuse, due in part to the position reducing the likelihood of the filament breaking upon repeating flexing of the composite tube 1201. Centralizing the filaments 1215 can also reduce the risk of an ignition hazard because the filaments 1215 are coated in layers of insulation and removed from the gas path.

As explained above, some of the examples illustrate suitable placements of filaments 1215 in the second elongate member 1205. In the foregoing examples comprising more than one filament 1215, the filaments 1215 are generally aligned along a horizontal axis. Alternative configurations are also suitable. For example, two filaments can be aligned along a vertical axis or along a diagonal axis. Four filaments can be aligned along a vertical axis or a diagonal axis. Four filaments can be aligned in a cross-shaped configuration, with one filament disposed at the top of the second elongate member, one filament disposed at the bottom of the second elongate member (near the tube lumen), and two filaments disposed on opposite arms of a "T," "Y," or triangle base.

TABLES 1A and 1B show some preferred dimensions of medical tubes described herein, as well as some preferred ranges for these dimensions. The dimensions refer to a transverse cross-section of a tube. In these tables, lumen diameter represents the inner diameter of a tube. Pitch represents the distance between two repeating points measured axially along the tube, namely, the distance between the tip of the vertical portions of adjacent "T"s of the second elongate member. Bubble width represents the width (maximum outer diameter) of a bubble. Bubble height represents the height of a bubble from the tube lumen. Bead height represents the maximum height of the second elongate member from the tube lumen (e.g., the height of the vertical portion of the "T"). Bead width represents the maximum width of the second elongate member (e.g., the width of the horizontal portion of the "T"). Bubble thickness represents the thickness of the bubble wall.

TABLE 1A

| Feature | Infant Dimension (mm) | Range (±) | Adult Dimension (mm) | Range (±) |
|---|---|---|---|---|
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 2.4 | 1 |
| Bubble height | 2.8 | 1 | 3.5 | 0.5 |
| Bead height | 0.9 | 0.5 | 1.5 | 0.5 |
| Bubble thickness | 0.4 | 0.35 | 0.2 | 0.15 |

TABLE 1B

| Feature | Infant Dimension (mm) | Range (±) | Adult Dimension (mm) | Range (±) |
|---|---|---|---|---|
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 3.4 | 1 |
| Bubble height | 2.8 | 1 | 4.0 | 0.5 |
| Bead height | 0.9 | 0.5 | 1.7 | 0.5 |
| Bubble thickness | 0.4 | 0.35 | 0.2 | 0.15 |

TABLES 2A and 2B provide example ratios between the dimensions of tube features for the tubes described in TABLES 1A and 1B respectively.

TABLE 2A

| Ratios | Infant | Adult |
|---|---|---|
| Lumen diameter:Pitch | 2.3:1 | 2.4:1 |
| Pitch:Bubble width | 1.1:1 | 1.1:1 |
| Pitch:Bead width | 2.2:1 | 3.1:1 |
| Bubble width:Bead width | 2.0:1 | 2.9:1 |
| Lumen diameter:Bubble height | 3.9:1 | 5.1:1 |
| Lumen diameter:Bead height | 12.2:1 | 12.0:1 |
| Bubble height:Bead height | 3.1:1 | 2.3:1 |
| Lumen diameter:Bubble thickness | 27.5:1 | 90.0:1 |

TABLE 2B

| Ratios | Infant | Adult |
|---|---|---|
| Lumen diameter:Pitch | 2.3:1 | 2.4:1 |
| Pitch:Bubble width | 1.1:1 | 1.1:1 |
| Pitch:Bead width | 2.2:1 | 2.2:1 |
| Bubble width:Bead width | 2.0:1 | 2.1:1 |
| Lumen diameter:Bubble height | 3.9:1 | 4.5:1 |
| Lumen diameter:Bead height | 12.2:1 | 10.6:1 |
| Bubble height:Bead height | 3.1:1 | 2.4:1 |
| Lumen diameter:Bubble thickness | 27.5:1 | 90.0:1 |

The following tables show some example properties of a composite tube (labeled "A"), described herein, having a heating filament integrated inside the second elongate member. For comparison, properties of a Fisher & Paykel model RT100 disposable corrugated tube (labeled "B") having a heating filament helically wound inside the bore of the tube are also presented.

Measurement of resistance to flow (RTF) was carried out according to Annex A of ISO 5367:2000(E). The results are summarized in TABLE 3. As seen below, the RTF for the composite tube is lower than the RTF for the model RT100 tube.

TABLE 3

| | RTF (cm H$_2$O) Flow rate (L/min) | | | |
|---|---|---|---|---|
| | 3 | 20 | 40 | 60 |
| A | 0 | 0.05 | 0.18 | 0.38 |
| B | 0 | 0.28 | 0.93 | 1.99 |

Condensate or "rainout" within the tube refers to the weight of condensate collected per day at 20 L/min gas flow rate and room temperature of 18° C. Humidified air is flowed through the tube continuously from a chamber. The tube weights are recorded before and after each day of testing. Three consecutive tests are carried out with the tube being dried in between each test. The results are shown below in TABLE 4. The results showed that rainout is significantly lower in the composite tube than in the model RT100 tube.

TABLE 4

| | Tube | | | | | |
|---|---|---|---|---|---|---|
| | A (Day 1) | A (Day 2) | A (Day 3) | B (Day 1) | B (Day 2) | B (day 3) |
| Weight before (g) | 136.20 | 136.70 | 136.70 | 111.00 | 111.10 | 111.10 |
| Weight after (g) | 139.90 | 140.00 | 139.20 | 190.20 | 178.80 | 167.10 |
| Condensate weight (g) | 3.7 | 3.3 | 2.5 | 79.20 | 67.70 | 56.00 |

The power requirement refers to the power consumed during the condensate test. In this test, the ambient air was held at 18° C. Humidification chambers (see, e.g., the humidification chamber 114 in FIG. 1) were powered by MR850 heater bases. The heating filaments in the tubes were powered independently from a DC power supply. Different flow rates were set and the chamber was left to settle to 37° C. at the chamber output. Then, the DC voltage to the circuits was altered to produce a temperature of 40° C. at the circuit output. The voltage required to maintain the output temperature was recorded and the resulting power calculated. The results are shown in TABLE 5. The results show that composite Tube A uses significantly more power than Tube B. This is because Tube B uses a helical heating filament in the tube bore to heat the gas from 37° C. to 40° C. The composite tube does not tend to heat gas quickly because the heating filament is in the wall of the tube (embedded in the second elongate member). Instead, the composite tube is designed to maintain the gas temperature and prevent rainout by maintaining the tube bore at a temperature above the dew point of the humidified gas.

TABLE 5

| | Flow rate (L/min) | | |
|---|---|---|---|
| | 40 | 30 | 20 |
| Tube A, power required (W) | 46.8 | 38.5 | 37.8 |
| Tube B, power required (W) | 28.0 | 27.5 | 26.8 |

Tube flexibility was tested by using a three-point bend test. Tubes were placed in a three point bend test jig and used along with an Instron 5560 Test System instrument, to measure load and extension. Each tube sample was tested three times; measuring the extension of the tube against the applied load, to obtain average respective stiffness constants. The average stiffness constants for Tube A and Tube B are reproduced in TABLE 6.

TABLE 6

| Tube | Stiffness (N/mm) |
|------|------------------|
| A    | 0.028            |
| B    | 0.088            |

As described above, heating wires 206 can be placed within the inspiratory limb 202 and/or the expiratory limb 210 to reduce the risk of rain out in the tubes by maintaining the tube wall temperature above the dew point temperature.

Thermal Properties

In embodiments of a composite tube 1201 incorporating a heating filament 1215, heat can be lost through the walls of the first elongate member 1203, resulting in uneven heating. As explained above, one way to compensate for these heat losses is to apply an external heating source at the first elongate member 1203 walls, which helps to regulate the temperature and counter the heat loss. Other methods for optimizing thermal properties can also be used, however.

Reference is next made to FIGS. 19A through 19C, which demonstrate example configurations for bubble height (that is, the cross-sectional height of the first elongate member 1203 measured from the surface facing the inner lumen to the surface forming the maximum outer diameter) to improve thermal properties.

The dimensions of the bubble can be selected to reduce heat loss from the composite tube 1201. Generally, increasing the height of the bubble increases the effective thermal resistance of the tube 1201, because a larger bubble height permits the first elongate member 1203 to hold more insulating air. However, it was discovered that, at a certain bubble height, changes in air density cause convection inside the tube 1201, thereby increasing heat loss. Also, at a certain bubble height the surface area becomes so large that the heat lost through surface outweighs the benefits of the increased height of the bubble. Certain embodiments include these realizations.

The radius of curvature and the curvature of the bubble can be useful for determining a desirable bubble height. The curvature of an object is defined as the inverse of the radius of curvature of that object. Therefore, the larger a radius of curvature an object has, the less curved the object is. For example, a flat surface would have an infinite radius of curvature, and therefore a curvature of 0.

FIG. 19A shows a longitudinal cross-section of a top portion of a composite tube. FIG. 19A shows an embodiment of a composite tube 1201 where the bubble has a large height. In this example, the bubble has a relatively small radius of curvature and therefore a large curvature. Also, the bubble is approximately three to four times greater in height than the height of the second elongate member 1205.

FIG. 19B shows a longitudinal cross-section of a top portion of another composite tube. FIG. 19B shows an embodiment of a composite tube 1201 where the bubble is flattened on top. In this example, the bubble has a very large radius of curvature but a small curvature. Also, the bubble is approximately the same height as the second elongate member 1205.

FIG. 19C shows a longitudinal cross-section of a top portion of another composite tube. FIG. 19C shows an embodiment of a composite tube 1201 where the width of the bubble is greater than the height of the bubble. In this example, the bubble has radius of curvature and the curvature between that of FIG. 19A and FIG. 19B, and the center of the radius for the upper portion of the bubble is outside of the bubble (as compared to FIG. 19A). The inflection points on the left and right sides of the bubble are about at the middle (heightwise) of the bubble (as opposed to in the lower portion of the bubble, as in FIG. 19A). Also, the height of the bubble is approximately double that of the second elongate member 1205, resulting in a bubble height between that of FIG. 19A and FIG. 19B.

The configuration of FIG. 19A resulted in the lowest heat loss from the tube. The configuration of FIG. 19B resulted in the highest heat loss from the tube. The configuration of FIG. 19C had intermediate heat loss between the configurations of FIGS. 19A and 19B. However, the large external surface area and convective heat transfer in the configuration of FIG. 19A led to inefficient heating. Thus, of the three bubble arrangements of FIGS. 19A-19C, FIG. 19C was determined to have the best overall thermal properties. When the same thermal energy was input to the three tubes, the configuration of FIG. 19C allowed for the largest temperature rise along the length of the tube. The bubble of FIG. 19C is sufficiently large to increase the insulating air volume, but not large enough to cause a significant convective heat loss. The configuration of FIG. 19B was determined to have the poorest thermal properties, namely that the configuration of FIG. 19B allowed for the smallest temperature rise along the length of the tube. The configuration of FIG. 19A had intermediate thermal properties and allowed for a lower temperature rise than the configuration of FIG. 19C.

It should be appreciated that although the FIG. 19C configuration may be preferred in certain embodiments, other configurations, including those of FIGS. 19A, 19B and other variations, may be utilized in other embodiments as may be desired.

TABLE 7 shows the height of the bubble, the outer diameter of the tube, and the radius of curvature of the configurations shown in each of FIGS. 19A, 19B, and 19C.

TABLE 7

|  | Tube (FIG.) | | |
|---|---|---|---|
|  | 19A | 19B | 19C |
| Bubble height (mm) | 3.5 | 5.25 | 1.75 |
| Outer diameter (mm) | 21.5 | 23.25 | 19.75 |
| Radius of curvature (mm) | 5.4 | 3.3 | 24.3 |

Reference is next made to FIGS. 19C through 19F which demonstrate example positioning of heating element 1215 with similar bubble shapes to improve thermal properties. The location of the heating element 1215 can change the thermal properties within the composite tube 1201.

FIG. 19C shows a longitudinal cross-section of a top portion of another composite tube. FIG. 19C shows an embodiment of a composite tube 1201 where the heating elements 1215 are centrally located in the second elongate member 1205. This example shows the heating elements 1215 close to one another and not close to the bubble wall.

Figure 19D:
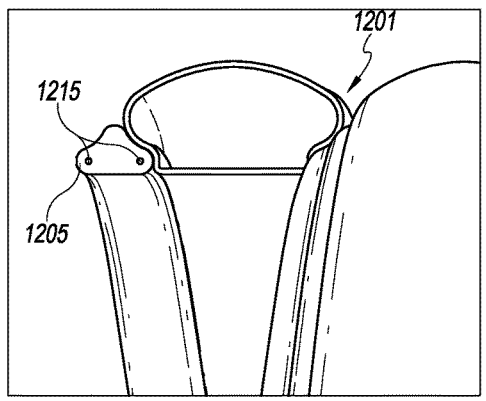
FIGS. 19D-F show examples of filament arrangements configured to improve thermal efficiency.

FIG. 19D shows a longitudinal cross-section of a top portion of another composite tube. FIG. 19D shows an embodiment of a composite tube 1201 in which the heating elements 1215 are spaced farther apart, as compared to FIG.

19C, in the second elongate member 1205. These heating elements are closer to the bubble wall and provide for better regulation of heat within the composite tube 1201.

Figure 19E:
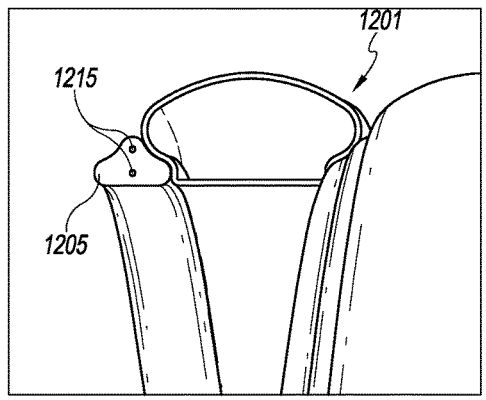

FIG. 19E shows a longitudinal cross-section of a top portion of another composite tube. FIG. 19E shows an embodiment of a composite tube 1201 wherein the heating elements 1215 are spaced on top of each other in the vertical axis of the second elongate member 1205. In this example, the heating elements 1215 are equally close to each bubble wall.

Figure 19F:
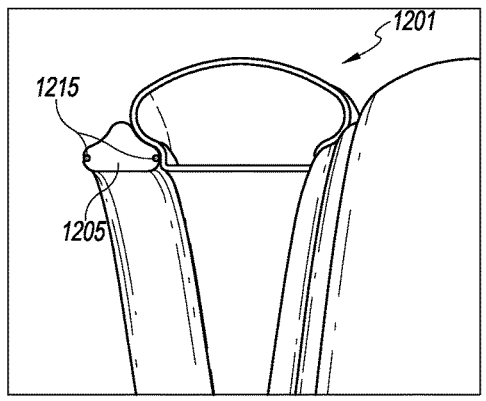

FIG. 19F shows a longitudinal cross-section of a top portion of another composite tube. FIG. 19F shows an embodiment of a composite tube 201 where the heating elements 1215 are spaced at opposite ends of the second elongate member 1205. The heating elements 1215 are close to the bubble wall, especially as compared to FIGS. 19C-19E.

Of the four filament arrangements of FIGS. 19C-19F, FIG. 19F was determined to have the best thermal properties. Because of their similar bubble shapes, all of the configurations experienced similar heat loss from the tube. However, when the same thermal energy was input to the tubes, the filament configuration of FIG. 19F allowed for the largest temperature rise along the length of the tube. The configuration of FIG. 19D was determined to have the next best thermal properties and allowed for the next largest temperature rise along the length of tube. The configuration of FIG. 19C performed next best. The configuration of FIG. 19E had the poorest performance and allowed for the smallest temperature rise along the length of the tube, when the same amount of heat was input.

It should be appreciated that although the FIG. 19F configuration may be preferred in certain embodiments, other configurations, including those of FIGS. 19C, 19D, 19E, and other variations, may be utilized in other embodiments as may be desired.

Figure 20A:
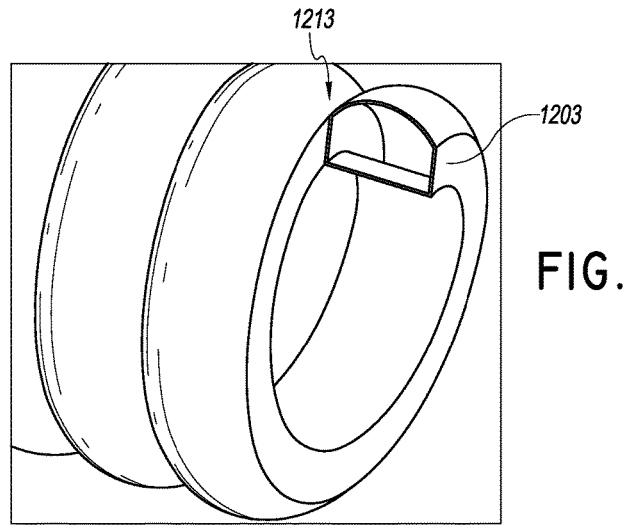
FIGS. 20A-C show examples of first elongate member stacking.
Figure 20B:
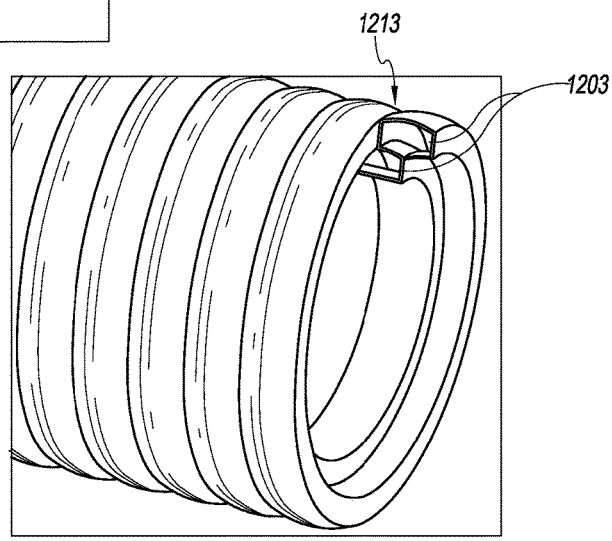
Figure 20C:
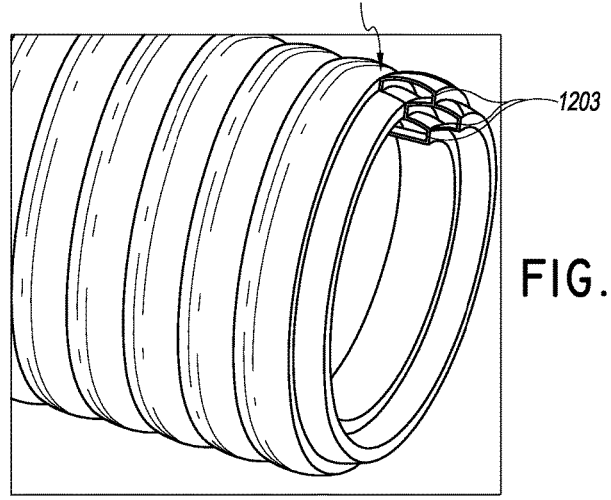

Reference is next made to FIGS. 20A through 20C, which demonstrate example configurations for stacking of the first elongate member 1203. It was discovered that heat distribution can be improved in certain embodiments by stacking multiple bubbles. These embodiments can be more beneficial when using an internal heating filament 1215. FIG. 20A shows a longitudinal cross-section of a top portion of another composite tube. FIG. 20A shows a cross section of a composite tube 1201 without any stacking.

FIG. 20B shows a longitudinal cross-section of a top portion of another composite tube. FIG. 20B shows another example composite tube 1201 with stacked bubbles. In this example, two bubbles are stacked on top of each other to form the first elongate member 1203. As compared to FIG. 20A, the total bubble height is maintained, but the bubble pitch is half of FIG. 20A. Also, the embodiment in FIG. 20B has only a slight reduction in air volume. The stacking of the bubbles reduces natural convection and heat transfer in the gap between bubbles 1213 and lowers the overall thermal resistance. The heat flow path increases in the stacked bubbles allowing heat to more easily distribute through the composite tube 1201.

FIG. 20C shows a longitudinal cross-section of a top portion of another composite tube. FIG. 20C shows another example of a composite tube 1201 with stacked bubbles. In this example, three bubbles are stacked on top of each other to form the first elongate member 1203. As compared to FIG. 20A, the total bubble height is maintained, but the bubble pitch is a third of FIG. 20A. Also, the embodiment in FIG. 20B has only a slight reduction in air volume. The stacking of the bubbles reduces natural convection and heat transfer in the gap between bubbles 1213.

Example Embodiments

The following is a numbered list of example embodiments that are within the scope of this disclosure. The example embodiments that are listed should in no way be interpreted as limiting the scope of the embodiments. Various features of the example embodiments that are listed can be removed, added, or combined to form additional embodiments, which are part of this disclosure:

1. A medical tube comprising:
    a first segment of the medical tube comprising:
        a first structure forming a conduit configured to transport a humidified gas; and
        a first heater wire circuit;
    a second segment of the medical tube comprising:
        a second structure forming a conduit configured to transport the humidified gas; and
        a second heater wire circuit; and
    an intermediate connector comprising a connection circuit that electrically couples the first heater wire circuit to the second heater wire circuit, the intermediate connector coupled to a patient-end of the first segment of the medical tube and a chamber-end of the second segment of the medical tube to form a single conduit for the humidified gas,
    wherein at least a portion of the intermediate connector is covered by a portion of the first segment of the medical tube and/or a portion of the second segment of the medical tube such that the intermediate connector is internal to the medical tube,
    wherein, in a first mode, electrical power passes through the connection circuit to provide power to the first heater wire circuit without providing power to the second heater wire circuit, and in a second mode, electrical power passes through the connection circuit to provide power to both the first heater wire circuit and the second heater wire circuit.
2. The medical tube of embodiment 1, wherein the connection circuit comprises a diode.
3. The medical tube of any of embodiments 1 to 2, further comprising a first sensor positioned at the patient-end of the first segment.
4. The medical tube of embodiment 3, wherein the first sensor is one of a temperature sensor or a humidity sensor.
5. The medical tube of any of embodiments 1 to 4, further comprising a second sensor positioned at a patient-end of the second segment of the medical tube.
6. The medical tube of embodiment 5, wherein the second sensor is one of a temperature sensor or a humidity sensor.
7. The medical tube of any of embodiments 1 to 6, wherein the first structure comprises an elongate tube comprising:
    a first elongate member comprising a hollow body spirally wound to form at least in part the conduit having a longitudinal axis, a lumen extending along the longitudinal axis, and a hollow wall surrounding the lumen;
    a second elongate member spirally wound and joined between adjacent turns of the first elongate member, the second elongate member forming at least a portion of the lumen of the elongate tube.

8. The medical tube of embodiment 7, wherein the first elongate member forms in longitudinal cross-section a plurality of bubbles with a flattened surface at the lumen.
9. The medical tube of embodiment 8, wherein adjacent bubbles are separated by a gap above the second elongate member.
10. The medical tube of embodiment 8, wherein adjacent bubbles are not directly connected to each other.
11. The medical tube of embodiment 8, wherein the plurality of bubbles have perforations.
12. A respiratory humidification system comprising:
   an inspiratory limb comprising a first segment of the inspiratory limb having a first heater wire circuit, a second segment of the inspiratory limb having a second heater wire circuit, an intermediate connector having a connector circuit configured to electrically couple the first heater wire circuit to the second heater wire circuit, a first sensor positioned at a patient-end of the first segment, and a second sensor positioned at a patient-end of the second segment; and
   a controller;
   wherein the controller is adapted to selectively switch between a first mode and a second mode wherein in the first mode the controller provides electrical power to the first heater wire circuit through the connector circuit and in a second mode the controller provides electrical power to the first and second heater wire circuits.
13. The system of embodiment 12, wherein the switching is done based on input from one or both sensors.
14. The system of embodiment 13, wherein the input from one or both sensors includes one or more of temperature, flow, humidity, and power.
15. The system of any of embodiments 12 to 14, wherein the first and second modes are defined by a direction of current provided by a power source.
16. The system of any of embodiments 12 to 15, wherein the controller is adapted to selectively switch between a first sensor reading mode and a second sensor reading mode wherein in the first sensor reading mode the controller reads a signal from the second sensor and in the second sensor reading mode the controller reads a signal from both the first sensor and the second sensor.
17. The system of any of embodiments 12 to 16, wherein the first sensor and the second sensor are temperature sensors.
18. A dual limb circuit comprising:
   an inspiratory limb comprising a first segment of the inspiratory limb having a first heater wire circuit, a second segment of the inspiratory limb having a second heater wire circuit, an intermediate connector having a connector circuit configured to electrically couple the first heater wire circuit to the second heater wire circuit, a first sensor positioned at a patient-end of the first segment, and a second sensor positioned at a patient-end of the second segment;
   an expiratory limb;
   an interface connected to the inspiratory limb and the expiratory limb; and
   a controller;
   wherein the controller is adapted to selectively switch between a first mode and a second mode wherein in the first mode the controller provides electrical power to the first heater wire circuit through the connector circuit and in a second mode the controller provides electrical power to the first and second heater wire circuits.
19. The dual limb circuit of embodiment 18, wherein the expiratory limb comprises an expiratory heater wire circuit.
20. The dual limb circuit of embodiment 19, wherein the expiratory limb is heated using the expiratory heater wire circuit.
21. The dual limb circuit of embodiment 19, wherein the expiratory heater wire circuit is powered in parallel with the first heater wire circuit in the first segment of the inspiratory limb.
22. The dual limb circuit of embodiment 21, wherein the expiratory heater wire circuit can be configured to be powered in only the first mode, in only the second mode, or in both the first mode and in the second mode.
23. The dual limb circuit of any of embodiments 18 to 22, wherein the interface is connected via a wye-piece.
24. A segmented inspiratory limb configured to be heated along at least two segments, each segment of the inspiratory limb comprising:
   a first elongate member comprising a hollow body spirally wound to form at least in part an elongate tube having a longitudinal axis, a lumen extending along the longitudinal axis, and a hollow wall surrounding the lumen;
   a second elongate member spirally wound and joined between adjacent turns of the first elongate member, the second elongate member forming at least a portion of the lumen of the elongate tube.
25. A medical tube comprising:
   two segments, each segment comprising:
      an elongate hollow body spirally wound to form an elongate tube having a longitudinal axis, a lumen extending along the longitudinal axis, and a hollow wall surrounding the lumen, wherein the elongate hollow body has in transverse cross-section a wall defining at least a portion of the hollow body;
      a reinforcement portion extending along a length of the elongate hollow body being spirally positioned between adjacent turns of the elongate hollow body, wherein the reinforcement portion forms a portion of the lumen of the elongate tube;
      one or more conductive filaments embedded or encapsulated within the reinforcement portion;
      wherein the reinforcement portion is relatively thicker or more rigid than the wall of the elongate hollow body;
   a segment connector attached to the first segment, the segment connector comprising:
      connection pads configured to electrically coupled the conductive filaments from the first segment to the conductive filaments from the second segment when the first segment is physically coupled to the second segment; and
      a power diode electrically coupled to the conductive filaments of the first segment,
   wherein the power diode allows electrical power to be delivered to the conductive filaments of the first segment and prevents electrical power from being delivered to the conductive filaments of the second segment when provided with an electrical signal of a first polarity, and
   wherein the power diode allows the conductive filaments of the first segment and the conductive filaments of the second segment to be provided with electrical power when provided with an electrical signal of a second polarity.

26. A connector comprising:
a first heater wire incoming connection configured to be electrically coupled to a first incoming heater wire;
a second heater wire incoming connection configured to be electrically coupled to a second incoming heater wire;
a first heater wire outgoing connection configured to be electrically coupled to a first outgoing heater wire and electrically coupled to the first heater wire incoming connection;
a second heater wire outgoing connection configured to be electrically coupled to a second outgoing heater wire and electrically coupled to the second heater wire incoming connection;
a first signal wire incoming connection configured to be electrically coupled to a first incoming signal wire;
a second signal wire incoming connection configured to be electrically coupled to a second incoming signal wire;
a first signal wire outgoing connection configured to be electrically coupled to a first outgoing signal wire and electrically coupled to the first signal wire incoming connection;
a second signal wire outgoing connection configured to be electrically coupled to a second incoming signal wire and electrically coupled to the second signal wire incoming connection;
a power diode electrically coupled to the first heater wire incoming connection and the second heater wire incoming connection, the power diode configured to allow current to flow from the second incoming heater wire to the first incoming heater wire and to prevent current to flow from the first incoming heater wire to the second incoming heater wire;
a sensor electrically coupled to the first signal wire incoming connection; and
a signal diode electrically coupled to the sensor and the second signal wire incoming connection, the signal diode configured to allow current to flow from the second incoming signal wire through the sensor to the first incoming signal wire and to prevent current to flow from the first incoming signal wire through the sensor to the second incoming signal wire.

CONCLUSION

Examples of respiratory humidification systems with dual zone heating control and associated components and methods have been described with reference to the figures. The figures show various systems and modules and connections between them. The various modules and systems can be combined in various configurations and connections between the various modules and systems can represent physical or logical links. The representations in the figures have been presented to clearly illustrate principles related to providing dual zone heating control, and details regarding divisions of modules or systems have been provided for ease of description rather than attempting to delineate separate physical embodiments. The examples and figures are intended to illustrate and not to limit the scope of the inventions described herein. For example, the principles herein may be applied to a respiratory humidifier as well as other types of humidification systems, including surgical humidifiers. The principles herein may be applied in respiratory applications as well as in other scenarios where a temperature of gases is to be controlled along multiple segments subject to varying ambient temperatures.

As used herein, the term "processor" refers broadly to any suitable device, logical block, module, circuit, or combination of elements for executing instructions. For example, the controller 122 can include any conventional general purpose single- or multi-chip microprocessor such as a Pentium® processor, a MIPS® processor, a Power PC® processor, AMD® processor, ARM® processor, or an ALPHA® processor. In addition, the controller 122 can include any conventional special purpose microprocessor such as a digital signal processor or a microcontroller. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein, or can be a pure software in the main processor. For example, logic module 504 can be a software-implemented function block which does not utilize any additional and/or specialized hardware elements. Controller 122 can be implemented as a combination of computing devices, e.g., a combination of a DSP and a microprocessor, a combination of a microcontroller and a microprocessor, a plurality of microprocessors, one or more microprocessors in conjunction with a DSP core, or any other such configuration.

Data storage can refer to electronic circuitry that allows data to be stored and retrieved by a processor. Data storage can refer to external devices or systems, for example, disk drives or solid state drives. Data storage can also refer to fast semiconductor storage (chips), for example, Random Access Memory (RAM) or various forms of Read Only Memory (ROM), which are directly connected to the communication bus or the controller 122. Other types of data storage include bubble memory and core memory. Data storage can be physical hardware configured to store data in a non-transitory medium.

Although certain embodiments and examples are disclosed herein, inventive subject matter extends beyond the specifically disclosed embodiments to other alternative embodiments and/or uses, and to modifications and equivalents thereof. Thus, the scope of the claims or embodiments appended hereto is not limited by any of the particular embodiments described herein. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z each to be present. As used herein, the words "about" or "approximately" can mean a value is within ±10%, within ±5%, or within ±1% of the stated value.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and/or processes described herein may include an interface configured to permit interaction with users, operators, other systems, components, programs, and so forth.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A medical tube comprising:
    a first segment and a second segment, each segment comprising:
        an elongate hollow body spirally wound to form an elongate tube having a longitudinal axis, a lumen extending along the longitudinal axis, and a hollow wall surrounding the lumen, wherein the elongate hollow body has in a transverse cross-section a wall defining at least a portion of the lumen of the elongate tube;
        a reinforcement portion extending along a length of the elongate hollow body being spirally wound between adjacent turns of the elongate hollow body, wherein the reinforcement portion defines at least a portion of the lumen of the elongate tube and is more rigid than the wall of the elongate hollow body; and
        one or more conductive filaments embedded or encapsulated within the reinforcement portion; and
    a segment connector adapted to connect the first segment to the second segment, the segment connector comprising:
        connection pads configured to couple the one or more conductive filaments from the first segment to the one or more conductive filaments from the second segment; and
        a power diode coupled to the connection pads,
    wherein the power diode prevents power of a first polarity that is delivered to the one or more conductive filaments of the first segment from being delivered to the one or more conductive filaments of the second segment, and
    wherein the power diode allows power of a second polarity that is delivered to the one or more conductive filaments of the first segment to be delivered to the one or more conductive filaments of the second segment,
    wherein a heater circuit comprising the one or more conductive filaments of the first and second segments is independent of another heater circuit that heats another tube.

2. The medical tube of claim 1, wherein the lumen is configured to convey gases in a breathing circuit.

3. The medical tube of claim 1, wherein one or more sensor wires are embedded within the reinforcement portion.

4. The medical tube of claim 3, wherein the one or more sensor wires are configured to be connected to a temperature sensor, a flow rate sensor, an oxygen concentration sensor, or a humidity sensor.

5. The medical tube of claim 1, wherein lengths of the first segment and the second segment are different.

6. The medical tube of claim 1, wherein the first segment and the second segment are mechanically and electrically coupled by the segment connector.

7. The medical tube of claim 1, wherein the medical tube is configured to be used in conjunction with an incubator, wherein a portion of the medical tube is inserted into the incubator.

8. The medical tube of claim 7, wherein the first segment is located outside the incubator and the second segment corresponds to the portion of the medical tube inserted into the incubator.

9. The medical tube of claim 1, wherein the elongate hollow body is filled with a gas.

10. The medical tube of claim 1, wherein the medical tube is flexible.

11. The medical tube of claim 1, wherein the elongate hollow body is perforated.

12. The medical tube of claim 1, wherein the reinforcement portion is joined between adjacent turns of the spirally wound elongate hollow body and forms in a longitudinal cross-section a plurality of bubbles.

13. The medical tube of claim 12, wherein a width of each of the plurality of bubbles is greater than a height of each of the plurality of bubbles.

14. The medical tube of claim 12, wherein the plurality of bubbles are each separated by a gap in the longitudinal cross-section between the adjacent turns of the elongate hollow body.

15. The medical tube of claim 1, wherein the one or more conductive filaments are spaced apart from each other in the reinforcement portion.

16. The medical tube of claim 1, wherein the elongate hollow body comprises two or more portions, such that two or more bubbles are formed in a longitudinal cross-section.

17. A medical tube comprising:
- a first segment comprising one or more heater wires;
- a second segment comprising one or more heater wires;
- a connection circuit adapted to connect the first and second segments, the connection circuit comprising a diode; and
- a controller,
- wherein each of the first and second segments further comprises a spirally wound elongate hollow body and a spirally wound elongate bead member, the spirally wound elongate hollow body forming at least in part an elongate tube comprising a longitudinal axis and a lumen extending along the longitudinal axis, the elongate bead member forming at least a portion of the lumen and providing support for the elongate hollow body, and
- wherein the controller is adapted to selectively switch between a first mode in which the controller provides power to the first segment, and a second mode in which the controller provides power to the first and second segments,
- wherein a heater circuit comprising the one or more heater wires of the first and second segments is independent of another heater circuit that heats another tube.

18. The medical tube of claim 17, wherein one or more sensor wires are embedded within the elongate bead member.

19. The medical tube of claim 17, wherein a patient-end sensor is positioned at a patient-end of the second segment, the first segment comprising a first sensor wire circuit and the second segment comprising a second sensor wire circuit, the connection circuit comprising a sensor connection circuit that couples the first sensor wire circuit to the second sensor wire circuit, and wherein the patient-end sensor is coupled to the second sensor wire circuit.

20. The medical tube of claim 19, wherein the patient-end sensor is a temperature sensor, a flow rate sensor, an oxygen concentration sensor, or a humidity sensor.

21. The medical tube of claim 17, wherein the elongate bead member comprises a hollow body and forms in a longitudinal cross-section a plurality of bubbles with a flattened surface at the lumen of the elongate tube.

22. The medical tube of claim 17, wherein the elongate hollow body comprises in a transverse cross-section a wall defining at least a portion of the lumen of the elongate tube.

23. The medical tube of claim 17, wherein the first mode and the second mode are defined by a direction of current provided by a power source.

* * * * *

UNITED STATES PATENT AND TRADEMARK OFFICE
CERTIFICATE OF CORRECTION

PATENT NO. : 10,589,050 B2
APPLICATION NO. : 14/442688
DATED : March 17, 2020
INVENTOR(S) : Matthew Liam Buswell Page 1 of 1

It is certified that error appears in the above-identified patent and that said Letters Patent is hereby corrected as shown below:

On the Title Page

On page 4 in Column 2, item (56), Other Publications, Line 3, delete "Ovierview" and insert --Overview--.

In the Specification

In Column 1 at Line 15, delete "HUMIDICATION" and insert --HUMIDIFICATION--.

In Column 5 at Line 33, delete "141)" and insert --141 D--.

In Column 10 at Line 62, delete "03 m" and insert --0.7m--.

Signed and Sealed this
Fourth Day of August, 2020

Andrei Iancu
*Director of the United States Patent and Trademark Office*